United States Patent
Alfonta et al.

(10) Patent No.: US 12,359,238 B2
(45) Date of Patent: Jul. 15, 2025

(54) RECOMBINANT FLAVIN-ADENINE DINUCLEOTIDE GLUCOSE DEHYDROGENASE AND USES THEREOF

(71) Applicant: B. G. NEGEV TECHNOLOGIES AND APPLICATIONS LTD., AT BEN-GURION UNIVERSITY, Beer Sheva (IL)

(72) Inventors: Lital Alfonta, Omer (IL); Raz Zarivach, Beer Sheva (IL); Jennifer Grushka, Tel Aviv (IL); Itay Algov, Kadima (IL)

(73) Assignee: B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 1085 days.

(21) Appl. No.: 17/332,718

(22) Filed: May 27, 2021

(65) Prior Publication Data

US 2021/0292804 A1    Sep. 23, 2021

Related U.S. Application Data

(63) Continuation-in-part of application No. 16/636,013, filed as application No. PCT/IL2018/050863 on Aug. 2, 2018, now Pat. No. 11,365,399.

(30) Foreign Application Priority Data

Aug. 2, 2017  (IL) .......................... 253801

(51) Int. Cl.
*C12Q 1/00*    (2006.01)
*C12N 9/04*    (2006.01)
*C12Q 1/32*    (2006.01)

(52) U.S. Cl.
CPC .......... *C12Q 1/006* (2013.01); *C12N 9/0006* (2013.01); *C12Q 1/32* (2013.01); *C12Y 101/05* (2013.01)

(58) Field of Classification Search
CPC .......... C12Q 1/006; C12Q 1/32; C12Q 1/004; C12N 9/0006; C12Y 101/05
See application file for complete search history.

(56) References Cited

U.S. PATENT DOCUMENTS 7,497,940 B2 *  3/2009  Sode ............... A61B 5/150977
                                               205/777.5
7,741,090 B2 *  6/2010  Sode ..................... C12N 1/205
                                               435/190

(Continued)

FOREIGN PATENT DOCUMENTS

EP          2589659 A1    5/2013
WO     2017013495 A2    1/2017

(Continued)

OTHER PUBLICATIONS

Schein et al. Formation of Soluble Recombinant Proteins in *Escherichia coli* is Favored by Lower Growth Temperature. Schein et al. (Biotechnology (1988), 6, 291-294. (Year: 1988).*

(Continued)

*Primary Examiner* — Sean C. Barron
(74) *Attorney, Agent, or Firm* — The Roy Gross Law Firm, LLC; Roy D. Gross

(57) ABSTRACT

A polypeptide comprising a residue substituted by a non-canonical amino acid (ncAA) is provided. Methods for: (a) transferring an electron to an electrode, by coupling the polypeptide to an electrode; and (b) quantifying the amount of an analyte e.g., glucose are also provided.

17 Claims, 32 Drawing Sheets

Specification includes a Sequence Listing.

(56) References Cited

U.S. PATENT DOCUMENTS

| | | | |
|---|---|---|---|
| 8,354,112 B2 | 1/2013 | Sode | |
| 8,716,442 B2* | 5/2014 | Takenaka | C12Q 1/004 530/350 |
| 2004/0023330 A1 | 2/2004 | Sode | |
| 2017/0121751 A1 | 5/2017 | Kojima et al. | |
| 2018/0355022 A1 | 12/2018 | Masakari et al. | |

FOREIGN PATENT DOCUMENTS

| | | |
|---|---|---|
| WO | 2017094776 A1 | 6/2017 |
| WO | 2019026082 A1 | 2/2019 |

OTHER PUBLICATIONS

Wan et al. Pyrrolysyl-tRNA synthetase: An ordinary enzyme but an outstanding genetic code expansion tool. Biochemica et Biophysica Acta (2014), 1844, 1059-1070. (Year: 2014).*

Inyoung Lee et al, "The electrochemical behavior of a FAD dependent glucose dehydrogenase with direct electron transfer subunit by immobilization on self-assembled monolayers", Bioelectrochemistry, vol. 121, Jun. 2018, pp. 1-6.

H Yoshida et al, "Engineering a chimeric pyrroloquinoline quinone glucose dehydrogenase: improvement of EDTA tolerance, thermal stability and substrate specificity", Protein engineering, Jan. 1999, vol. 12 No. 1, pp. 63-70.

Yamaoka, H., Yamashita, Y., Ferri, S., & Sode, K. (2008), "Site directed mutagenesis studies of FAD-dependent glucose dehydrogenase catalytic subunit of Burkholderia cepacia" Biotechnology letters, 30(11), 1967-1972.

Simone, A. D. "Engineering the genetic code of Escherichia coli with methionine analogues and bioorthogonal amino acids for protein immobilization", 2016.

Joseph Wang, "Electrochemical Glucose Biosensors", Chem. Rev. 2008, 108, 2, 814-825.

L. Gorton et al, "Direct electron transfer between heme-containing enzymes and electrodes as basis for third generation biosensors", Analytica Chimica Acta, vol. 400, Issues 1-3, Nov. 22, 1999, pp. 91-108.

Wolfgang Harreither et al, "Recombinantly produced cellobiose dehydrogenase from Corynascus thermophilus for glucose biosensors and biofuel cells", Biotechnol J. Nov. 2012;7(11):1359-66.

Idan Gal et al, "Yeast surface display of dehydrogenases in microbial fuel-cells", Bioelectrochemistry. Dec. 2016;112:53-60.

B M Hallberg et al, "A new scaffold for binding haem in the cytochrome domain of the extracellular flavocytochrome cellobiose dehydrogenase", Structure. Jan. 15, 2000;8(1):79-88.

B M Hallberg et al, "Crystal structure of the flavoprotein domain of the extracellular flavocytochrome cellobiose dehydrogenase", J Mol Biol. Jan. 18, 2002;315(3):421-34.

G Gilardi et al, "Manipulating redox systems: application to nanotechnology", Trends Biotechnol . Nov. 2001;19(11):468-76.

Junko Okuda et al, "PQQ glucose dehydrogenase with novel electron transfer ability", Biochem Biophys Res Commun. Feb. 13, 2004;314(3):793-7.

Gianfranco Gilardi et al, "Molecular Lego: design of molecular assemblies of P450 enzymes for nanobiotechnology", Biosens Bioelectron. Jan. 2002;17(1-2):133-45.

Tomohiko Yamazaki et al, "Construction and Characterization of Direct Electron Transfer-Type Continuous Glucose Monitoring System Employing Thermostable Glucose Dehydrogenase Complex", Oct. 2008, Analytical Letters 41(13):2363-2373.

I Willner I et al, "Integration of Layered Redox Proteins and Conductive Supports for Bioelectronic Applications", Angew Chem Int Ed Engl. Apr. 2000;39(7):1180-1218.

Hideaki Yamaoka et al, "SPCE Based Glucose Sensor Employing Novel Thermostable Glucose Dehydrogenase, FADGDH: Blood Glucose Measurement with 150nL Sample in One Second", J Diabetes Sci Technol. Jan. 2007; 1(1): 28-35.

Yuki Yamashita et al, "Direct electron transfer type disposable sensor strip for glucose sensing employing an engineered FAD glucose dehydrogenase", Enzyme Microb Technol. Feb. 5, 2013;52(2):123-8.

Marina I Siponen et al, "Structural insight into magnetochrome-mediated magnetite biomineralization", Nature. Oct. 31, 2013;502(7473):681-4.

Itay Algov et al, "Highly Efficient Flavin-Adenine Dinucleotide Glucose Dehydrogenase Fused to a Minimal Cytochrome C Domain", J Am Chem Soc. Dec. 6, 2017;139(48):17217-17220.

PCT Search Report for International Application No. PCT/IL2018/050863; mailed Oct. 28, 2018 ; 4 pp.

PCT Written Opinion for International Application No. PCT/IL2018/050863; mailed Oct. 28, 2018 ; 6 pp.

PCT Preliminary Report for International Application No. PCT/IL2018/050863; dated Feb. 4, 2020 ; 7 pp.

Inose et al. 2003; Cloning and expression of the gene encoding catalytic subunit of the thermostable glucose dehydrogenase from Bukholderia cepacia in Escherichia col. Biochimicet Biophysica Acta 1645: 133-138.

Algov, Itay, Feiertag, Aviv, & Alfonta, Lital, Site-specifically wired and oriented glucose dehydrogenase fused to a minimal cytochrome with high glucose sensing sensitivity. Biosensors and Bioelectronics, 2021, 180: 113117, Feb. 27, 2021. doi: 10.1016/j.bios.2021.113117. Epub Feb. 27, 2021. PMID: 33677358.

Algov, Itay, et al. Highly efficient flavin-adenine dinucleotide glucose dehydrogenase fused to a minimal cytochrome C domain. Journal of the American Chemical Society, 2017, 139.48: 17217-17220, Sep. 15, 2017. doi: 10.1021/jacs.7b07011. Epub Sep. 21, 2017. PMID: 28915057.

Amir, Liron, et al. Surface display of a redox enzyme and its site-specific wiring to gold electrodes. Journal of the American Chemical Society, 2013, 135.1: 70-73, Dec. 8, 2012. doi: 10.1021/ja310556n. Epub Dec. 18, 2012. PMID: 23231821.

* cited by examiner

RECOMBINANT FLAVIN-ADENINE DINUCLEOTIDE GLUCOSE DEHYDROGENASE AND USES THEREOF

CROSS-REFERENCE TO RELATED APPLICATIONS

This application is a continuation-in-part of U.S. patent application Ser. No. 16/636,013, titled "A RECOMBINANT FLAVIN-ADENINE DINUCLEOTIDE GLUCOSE DEHYDROGENASE AND USES THEREOF", filed on Feb. 2, 2020, which claims priority to International Patent Application No. PCT/IL2018/050863, titled "A RECOMBINANT FLAVIN-ADENINE DINUCLEOTIDE GLUCOSE DEHYDROGENASE AND USES THEREOF", filed on Aug. 2, 2018, which claims priority to Israel Patent Application No. 253801, titled "A RECOMBINANT FLAVIN-ADENINE DINUCLEOTIDE GLUCOSE DEHYDROGENASE AND USES THEREOF", filed on Aug. 2, 2017. The contents of all the above applications are incorporated herein by reference in their entirety.

FIELD OF INVENTION

The present invention relates to recombinant proteins, methods of using the same such as for direct electron transfer in bio-electrochemical applications.

BACKGROUND OF THE INVENTION

Redox enzymes are proteins that participate in biocatalytic processes which involve electron transfer (ET). Depending on their redox potential, enzyme mediated redox reactions may be used in anodes and cathodes of biofuel cells as well as in biosensing applications. For the utilization of most redox enzymes in such devices, a mediator molecule should be used to mediate the ET between the enzyme and the electrode. The use of an external redox mediator results in a potential loss as well as in low power outputs.

Redox mediator molecules introduce two major challenges to the system: the first is having a middle point potential value that affords an efficient electron transfer from an enzyme to the electrode, which results in insufficient energy production. The other, is the need for diffusion of the mediator molecule through solution towards the electrode which might cause an additional loss of energy.

SUMMARY OF THE INVENTION

The present invention relates to a recombinant protein having superior FAD-GDH (flavin-adenine dinucleotide glucose dehydrogenase) activity and methods of using the same.

According to a first aspect, there is provided a recombinant protein, comprising (a) alpha subunit of an FAD-GDH; and (b) a minimal c-type cytochrome peptide, wherein the alpha subunit of an FAD-GDH comprises an amino acid sequence comprising a non-canonical amino acid (ncAA), and wherein said sequence is set forth in SEQ ID NO: 20 or SEQ ID NO: 22.

According to another aspect, there is provided a polynucleotide comprising a nucleic acid sequence encoding the herein disclosed polypeptide.

According to another aspect, there is provided an expression vector or a plasmid comprising the herein disclosed polynucleotide.

According to another aspect, there is provided a transgenic or a transfected cell comprising: (a) the polypeptide of the invention; (b) the herein disclosed polynucleotide; (c) the herein disclosed expression vector or the plasmid; or (d) any combination of (a) to (c).

According to another aspect, there is provided a composition comprising: (a) the polypeptide of the invention; (b) the herein disclosed polynucleotide; (c) the herein disclosed expression vector or the plasmid; (d) the herein disclosed transgenic or a transfected cell; (e) the herein disclosed extract; (f) any combination of (a) to (c), and an acceptable carrier.

According to another aspect, there is provided an electrode coupled to the polypeptide of the invention, wherein the coupled is by non-covalent interactions.

According to another aspect, there is provided a device comprising the herein disclosed electrode.

According to another aspect, there is provided a method for determining an analyte in a liquid medium, the analyte being capable to undergo a biocatalytic oxidation or reduction reaction in the presence of an oxidizer or a reducer, respectively, the method comprising: (i) providing the herein disclosed device; (ii) contacting the device with the liquid medium; (iii) measuring the electric signal generated between the cathode and the anode, the electric signal being indicative of the presence and/or the concentration of the analyte; and (iv) determining the analyte based on the electric signal.

According to another aspect, there is provided an extract obtained or derived from the herein disclosed transgenic or transfected cell.

In some embodiments, the ncAA comprises Propargyl-lysine (PrK).

In some embodiments, the ncAA is covalently bound to a mediator molecule, wherein the mediator molecule is represented by Formula I:

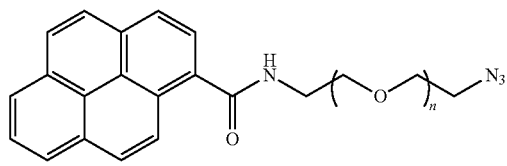

(I), wherein n is an integer in a range from 1 to 5.

In some embodiments, n equals 2.

In some embodiments, the polynucleotide comprises a nucleic acid sequence set forth in SEQ ID NO: 15 or SEQ ID NO: 17.

In some embodiments, the expression vector or plasmid further comprises a nucleic acid sequence encoding a gamma subunit of an FAD-GDH, and optionally wherein each of the polynucleotide encoding the polypeptide of the invention and the nucleic acid sequence encoding the gamma subunit of an FAD-GDH are operably linked to a separate regulatory element.

In some embodiments, the regulatory element is a T7 promoter.

In some embodiments, the cell is a prokaryotic cell.

In some embodiments, the extract comprises: (a) the polypeptide of the invention; (b) the herein disclosed polynucleotide; (c) the herein disclosed expression vector or the plasmid; or (d) any combination of (a) to (c).

In some embodiments, the analyte comprises glucose.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

Figures 12A, 12B:
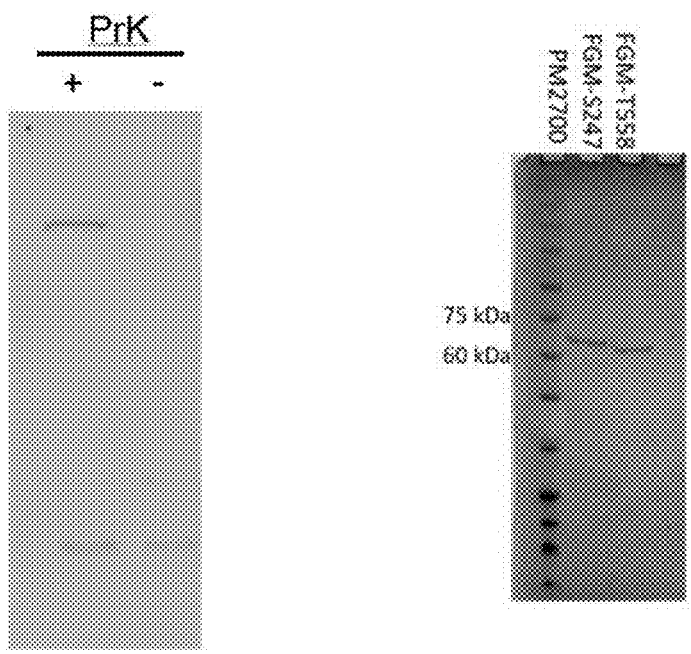
FIGS. 12A-12C present protein expression verification gel micrographs: anti his-tag Western blot of crude lysates from bacterial expression system with the supplementation (+) and without (−) of 2 mM PrK (FIG. 12A); in-gel heme staining of FGM-S247PrK and FGM-T558PrK (FIG. 12B)
Figure 12C:
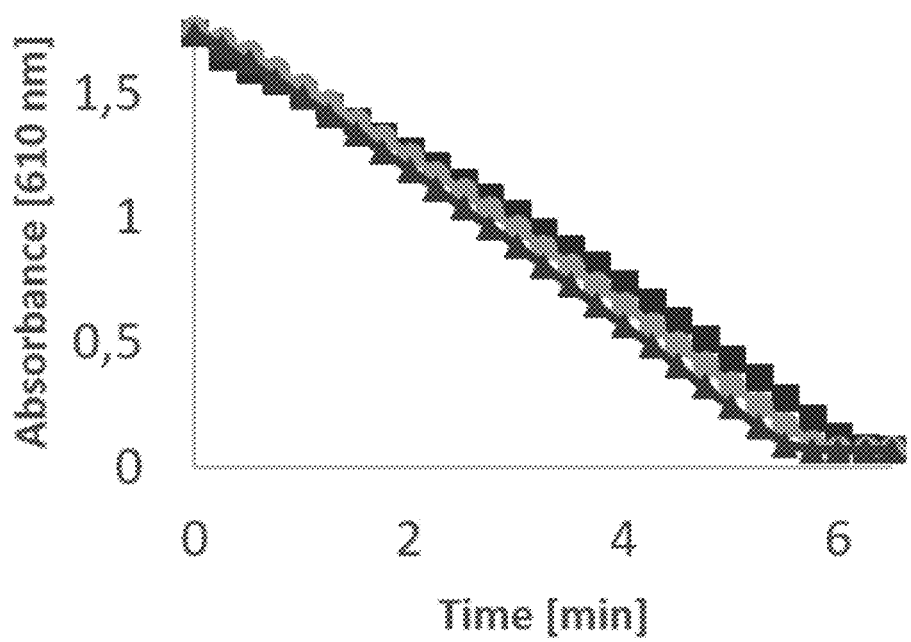

and a graph of DCIP FAD-GDH activity assay for glucose oxidation (FIG. 12C). Curves showing the reduction of DCIP by FGM-S247PrK (square), GDH-S247PrK (triangle) and FGM-T558PrK (circle).

Figure 13:
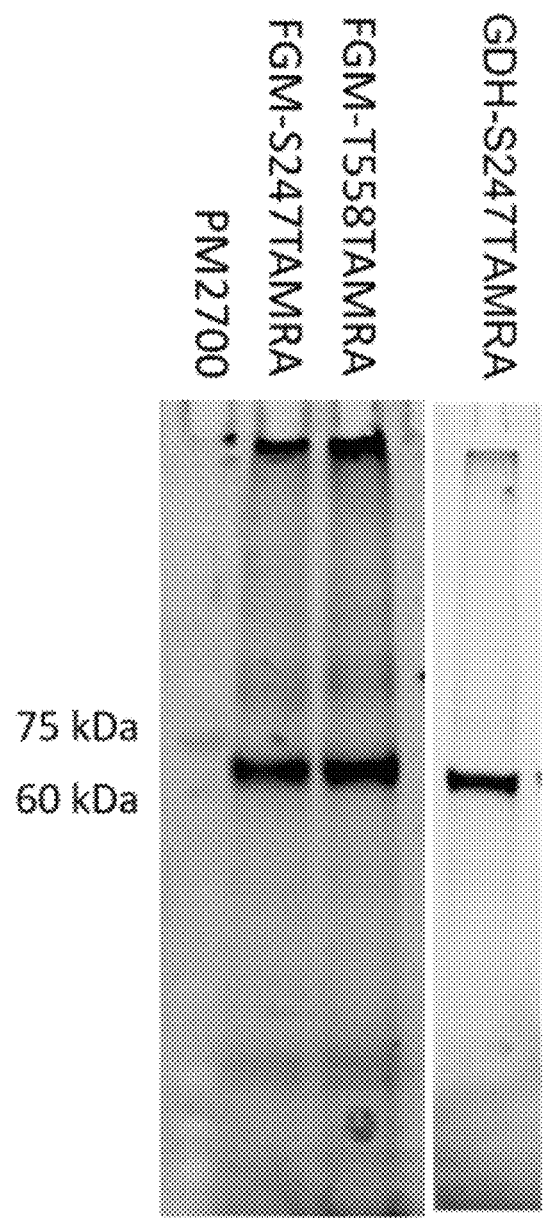
Figure 14:
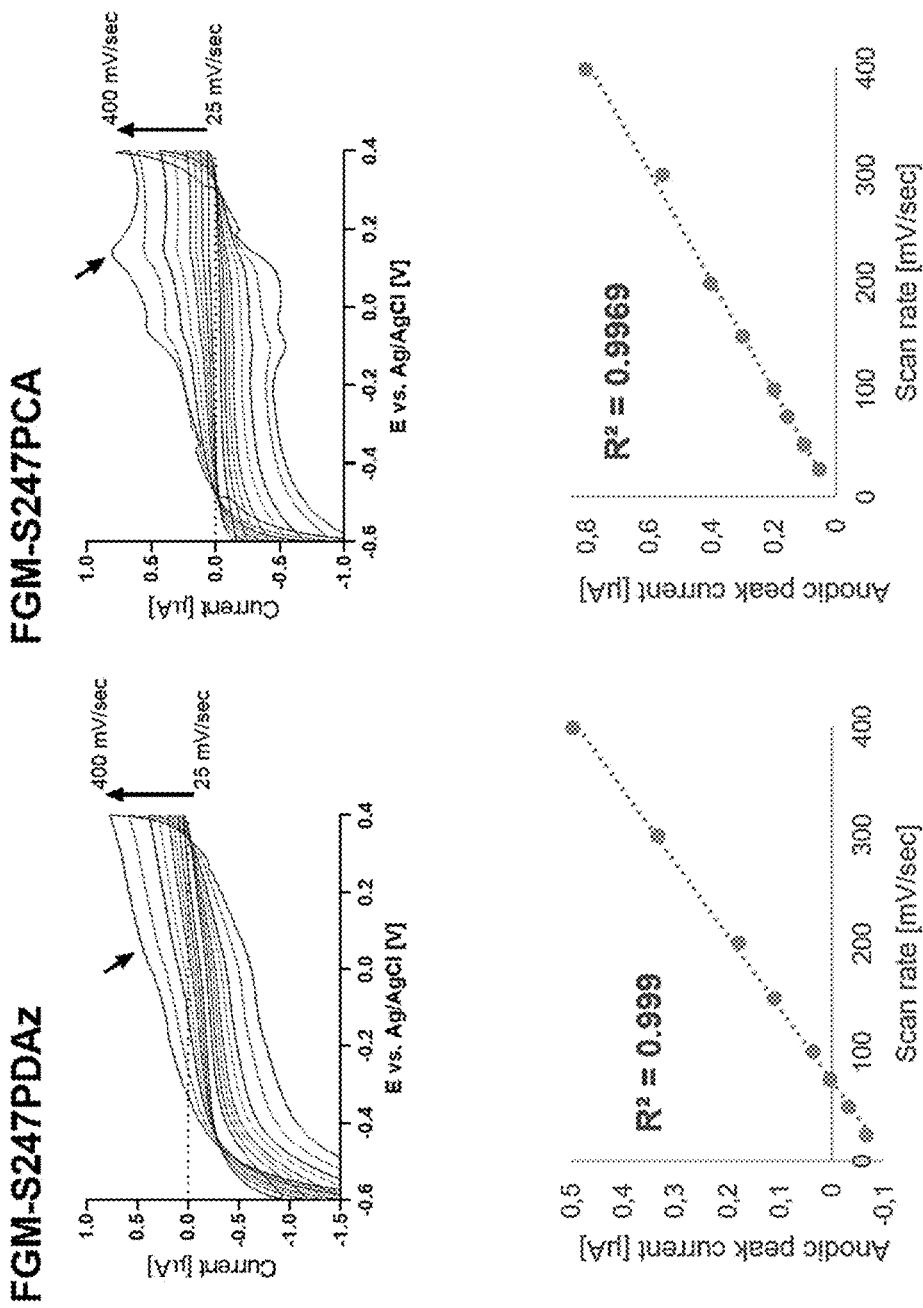
Figure 15A:
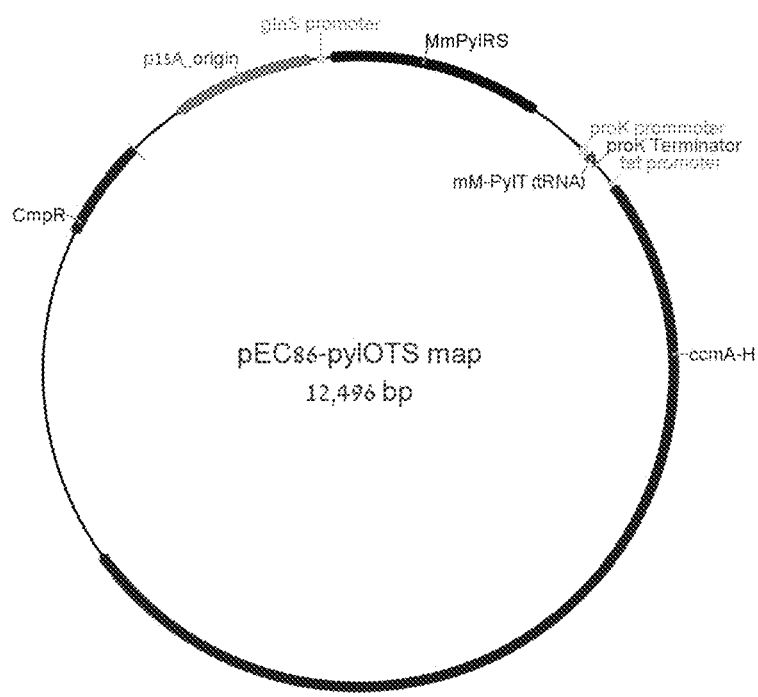
Figure 15B:
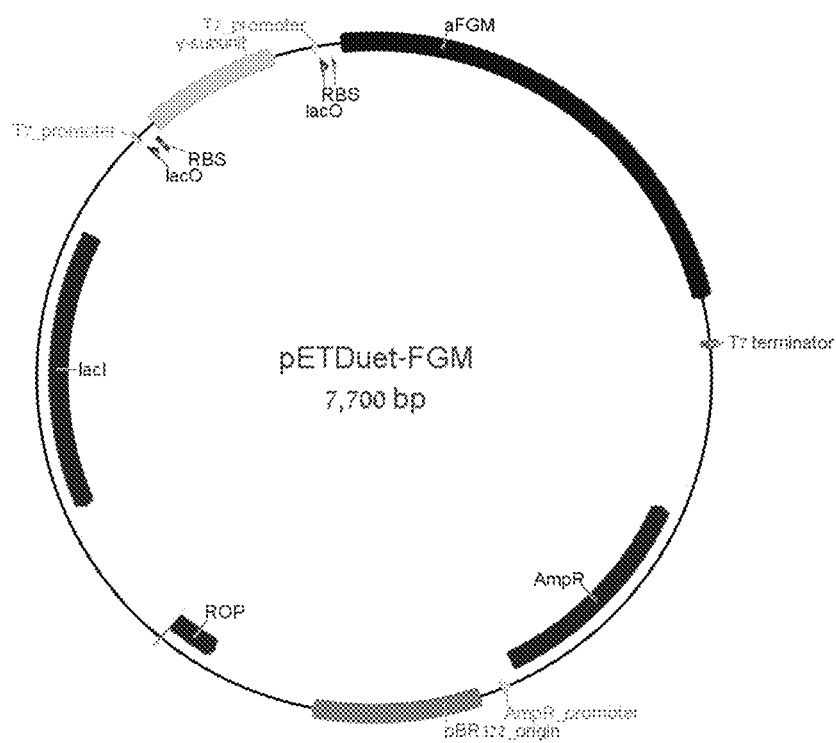
Figure 16:
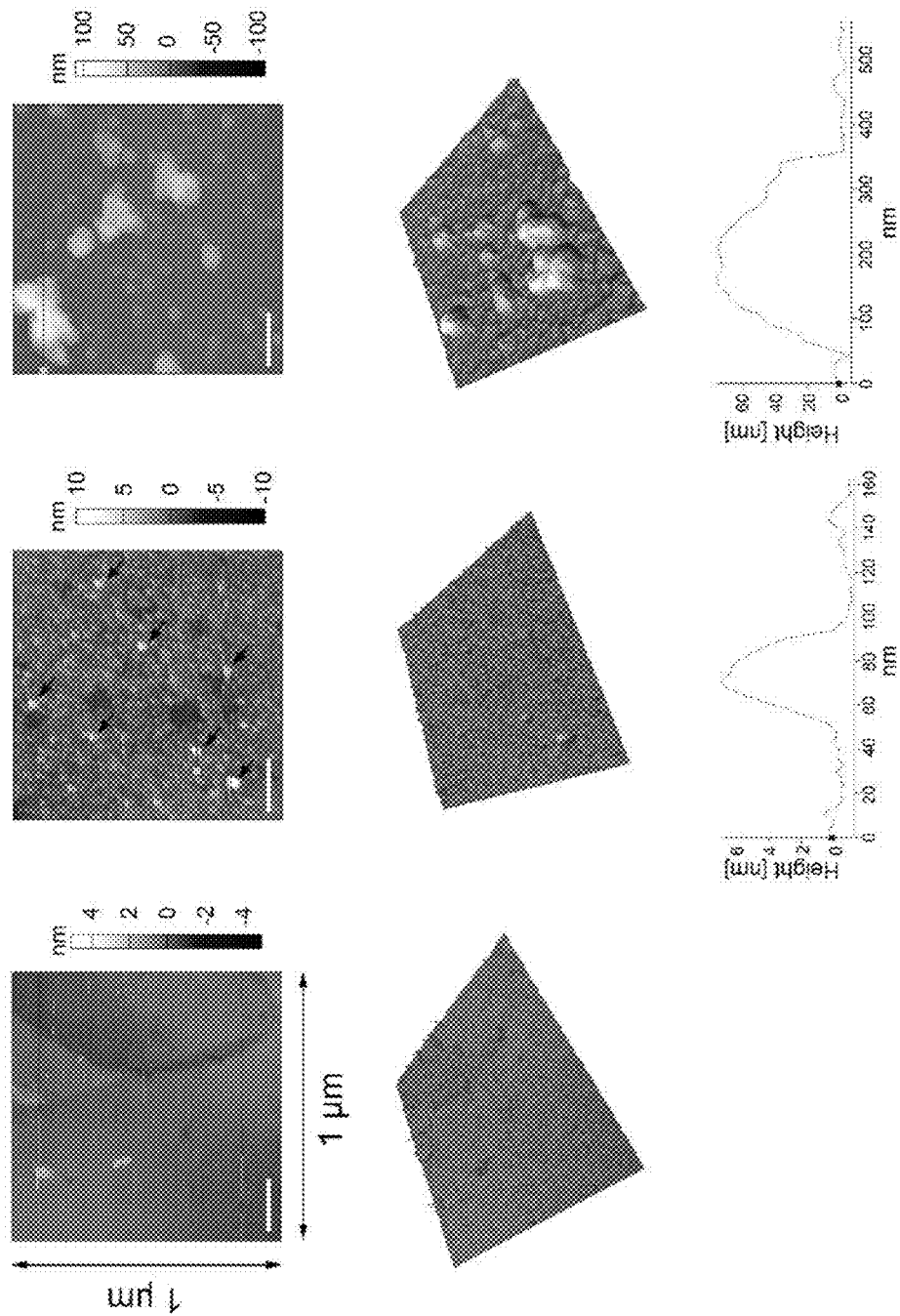
Figure 17:
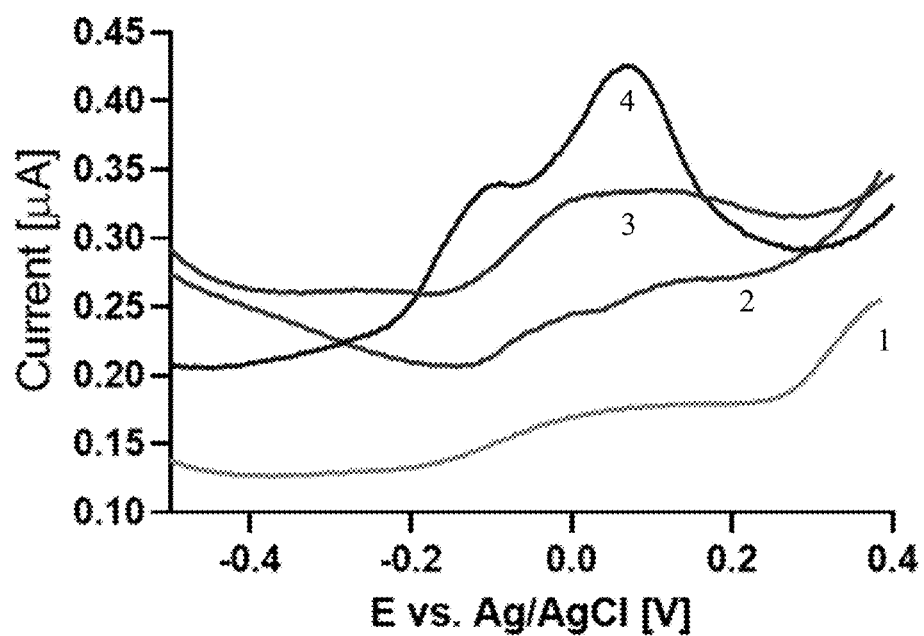
Figure 18A:
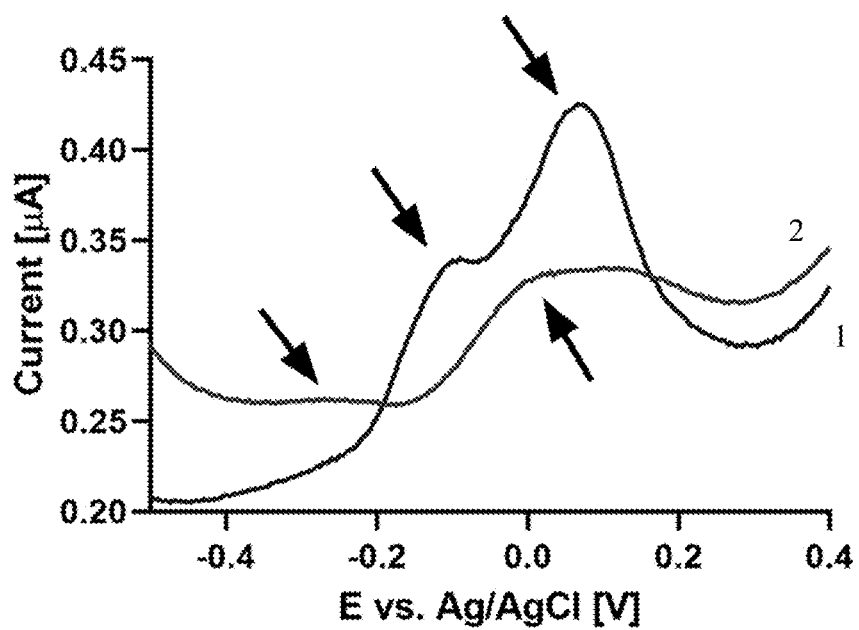
Figure 18B:
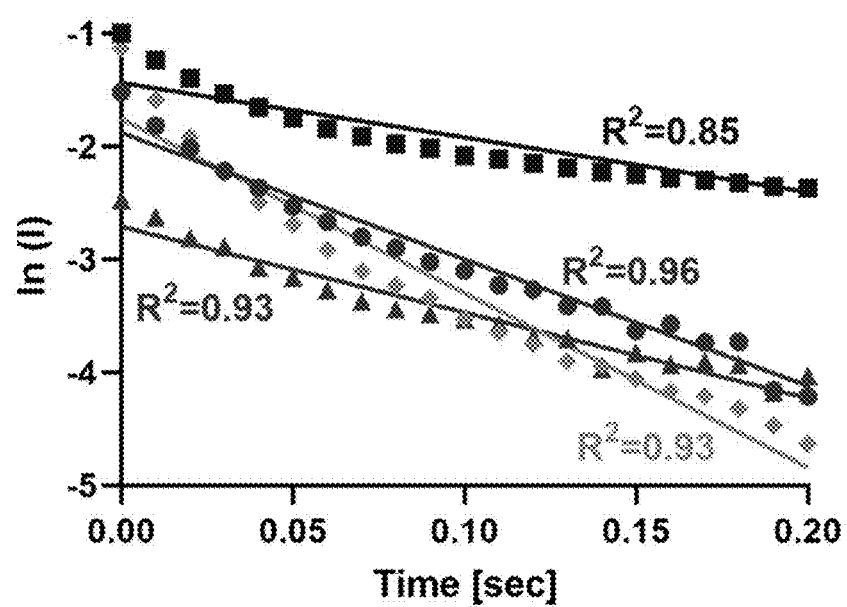
Figure 18C:
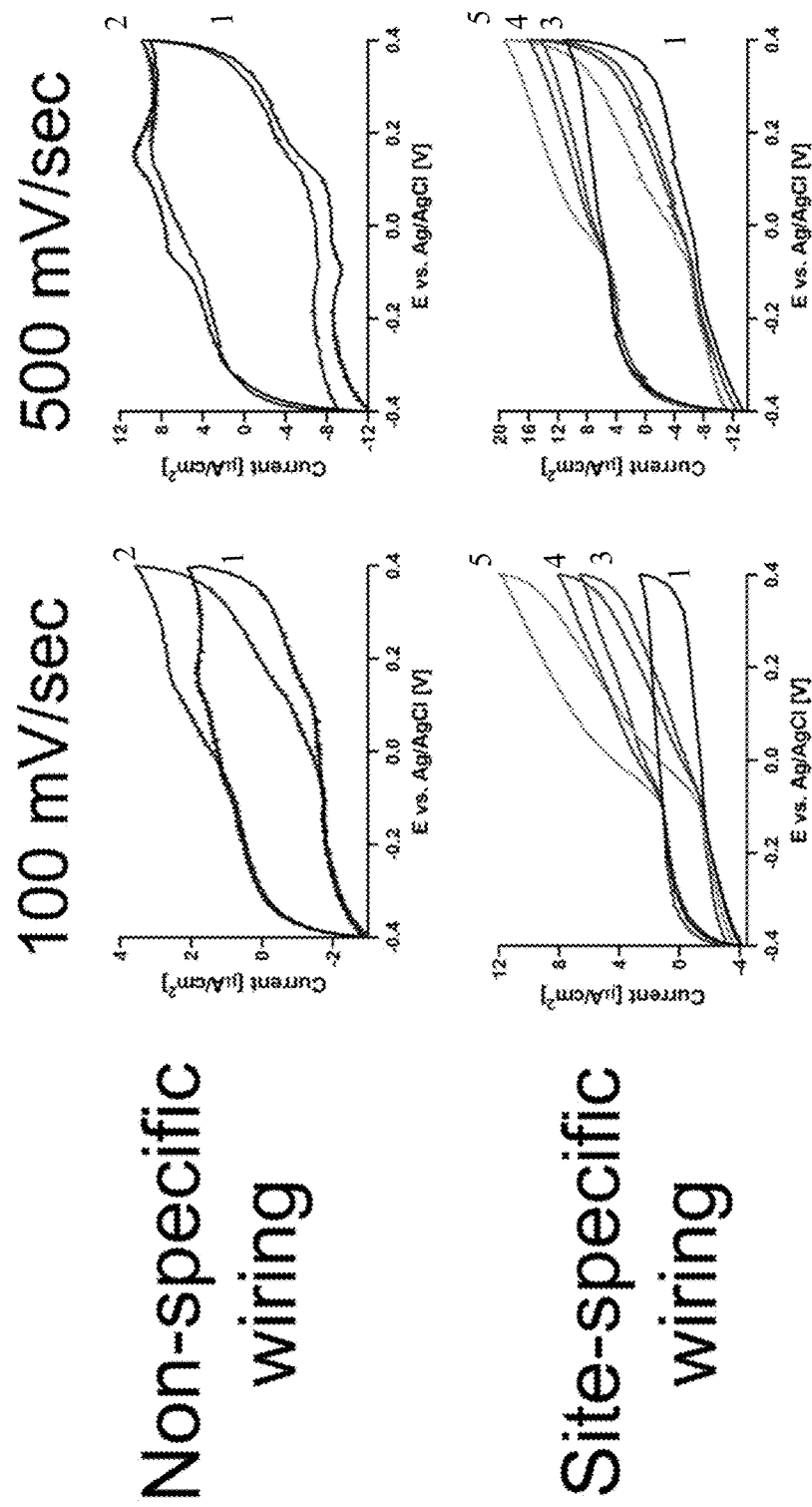
Figure 18D:
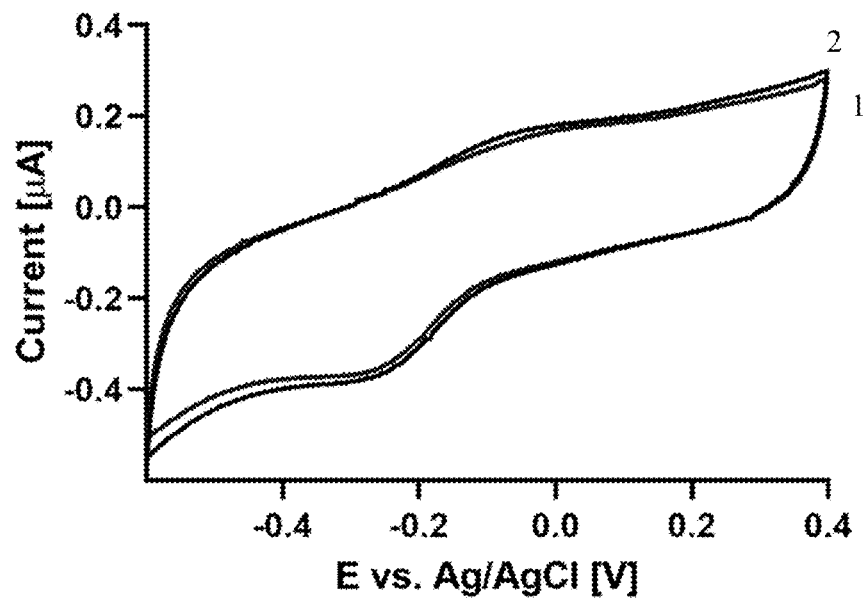
Figure 18E:
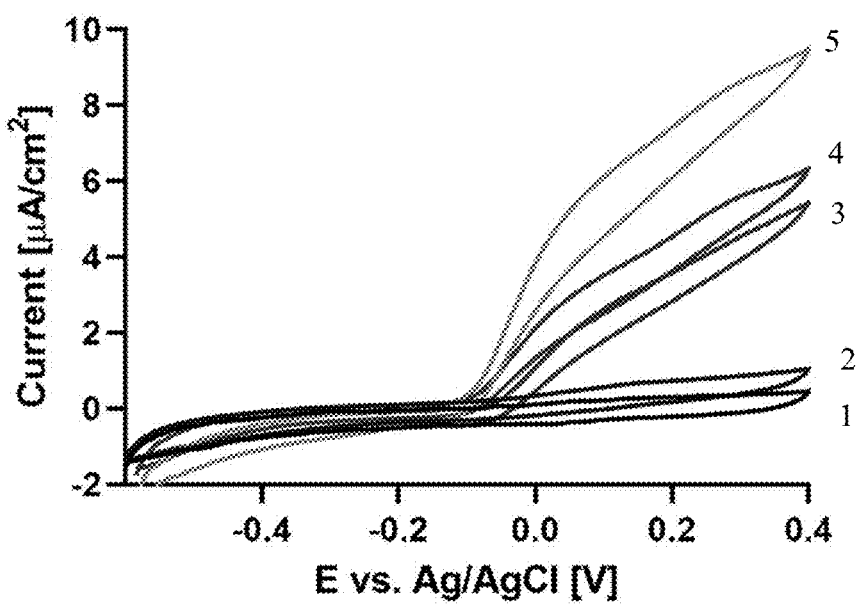
Figure 18F:
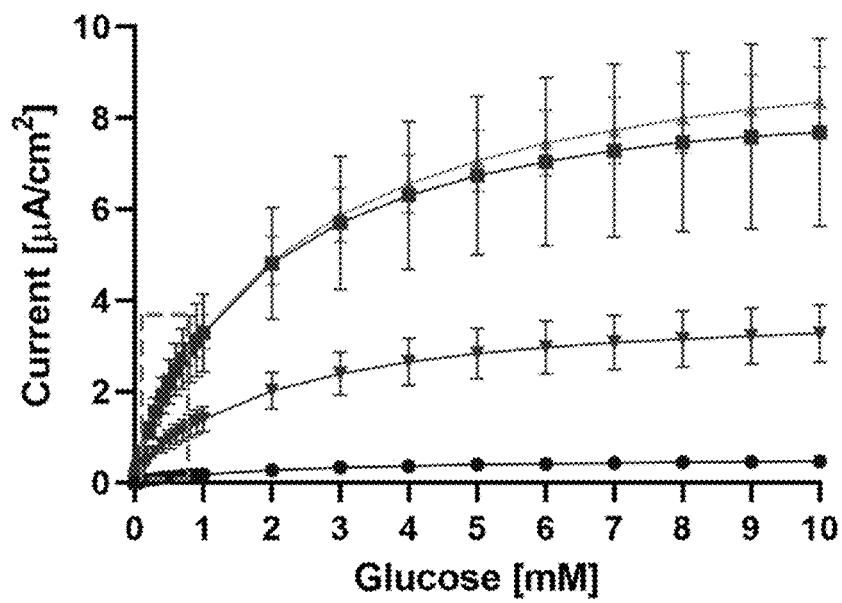
Figure 18G:
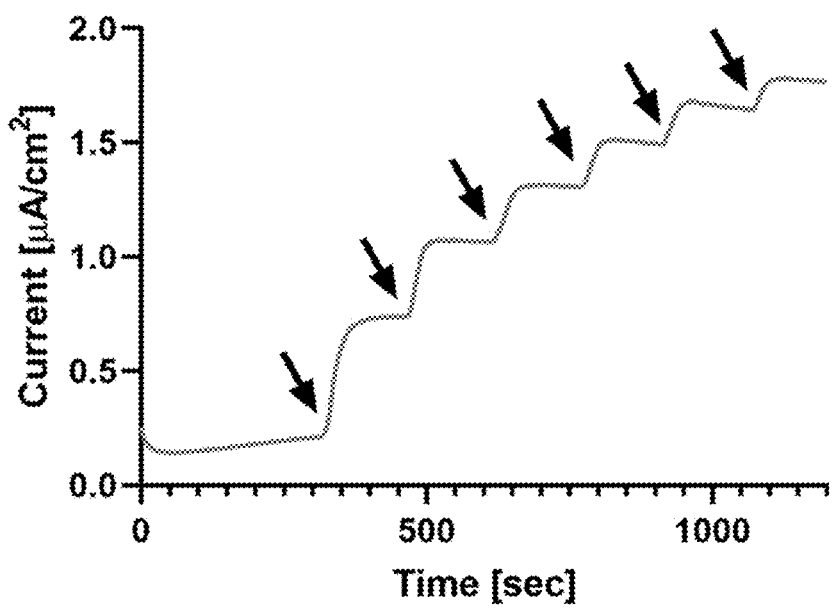
Figure 18H:
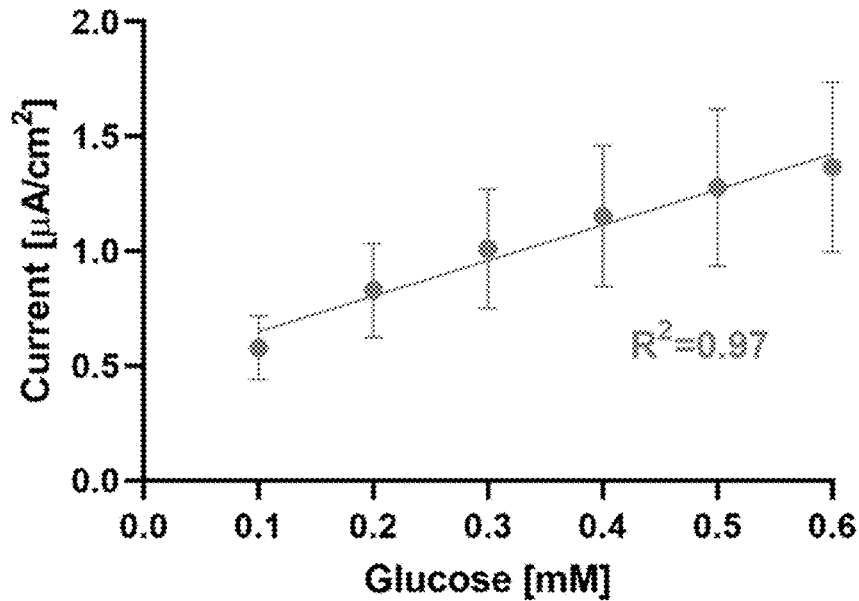
Figure 19A:
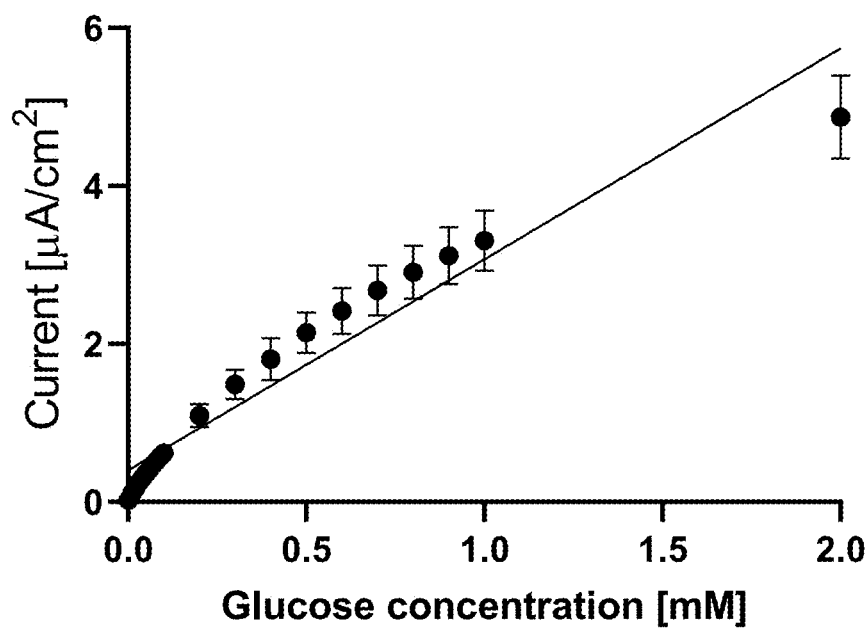
Figure 19B:
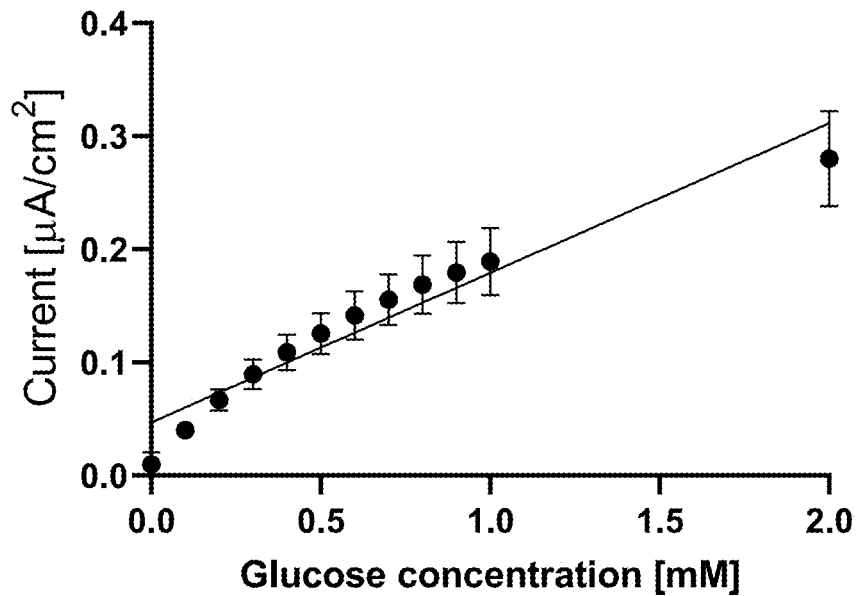
Figure 20:
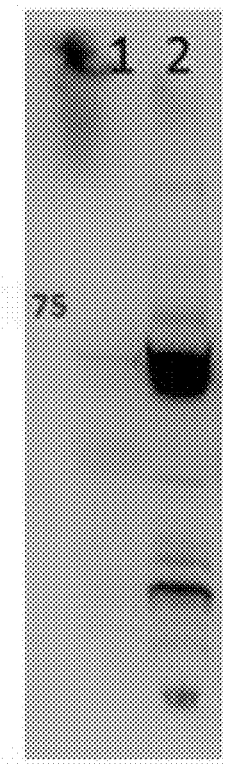
Figure 21:
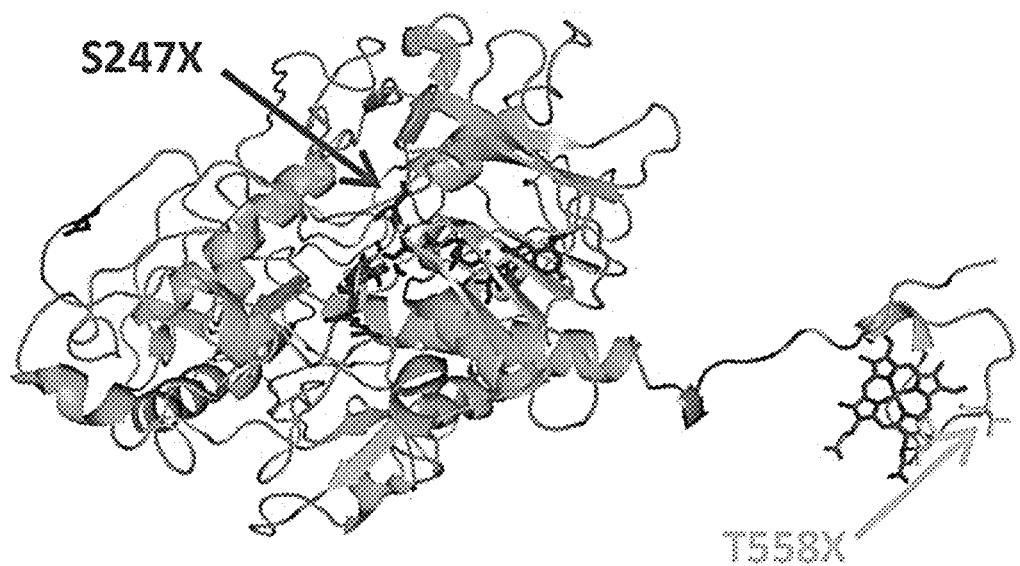
Figure 22A:
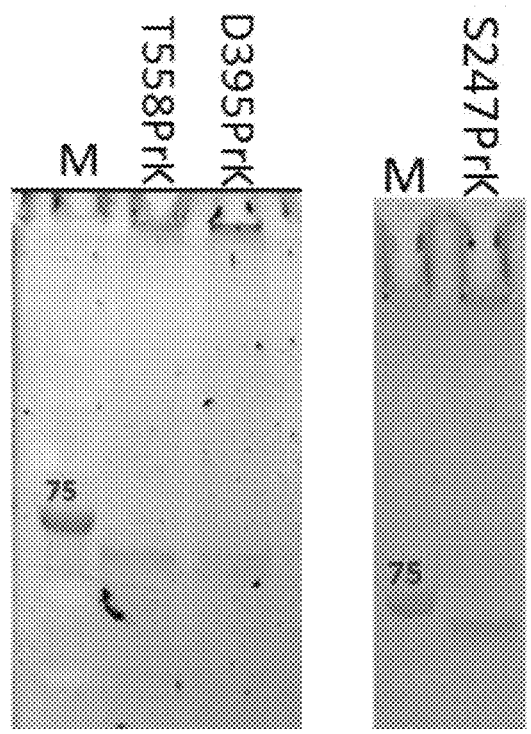
Figure 22B:
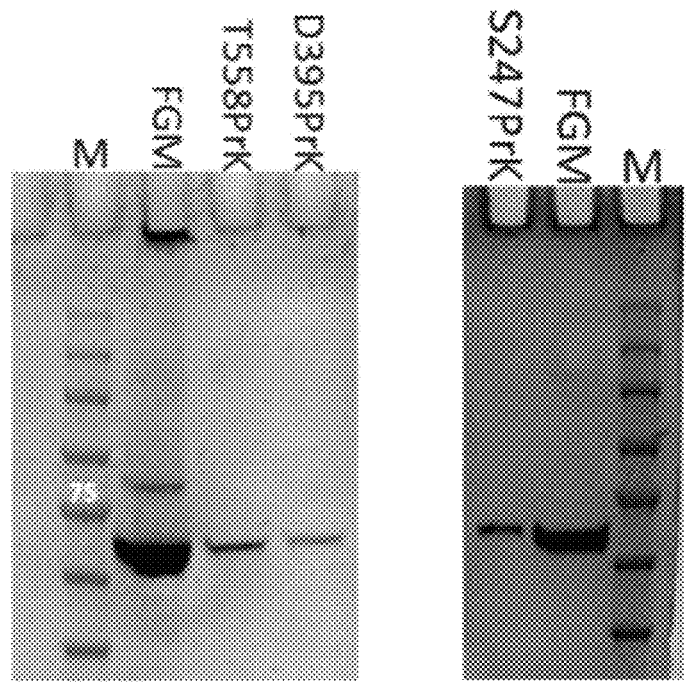
Figure 22C:
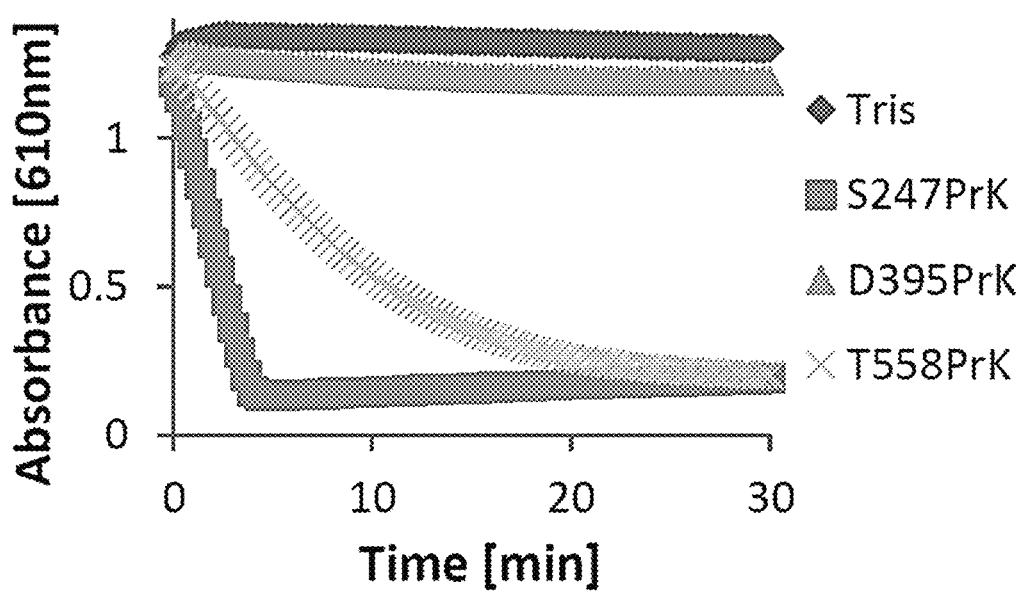
Figure 23A:
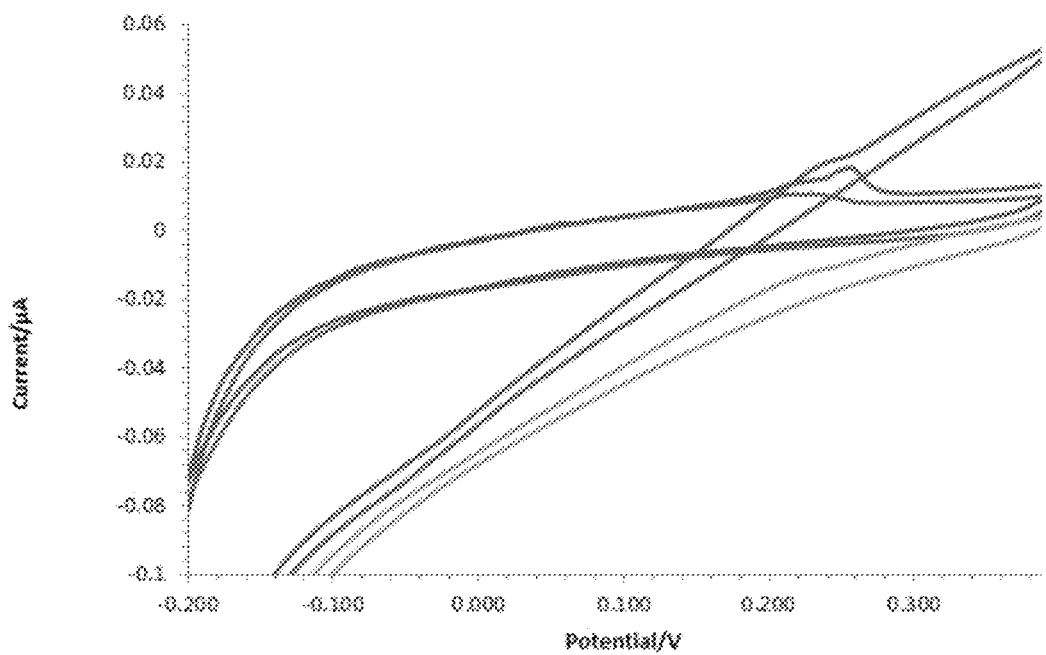
Figure 23B:
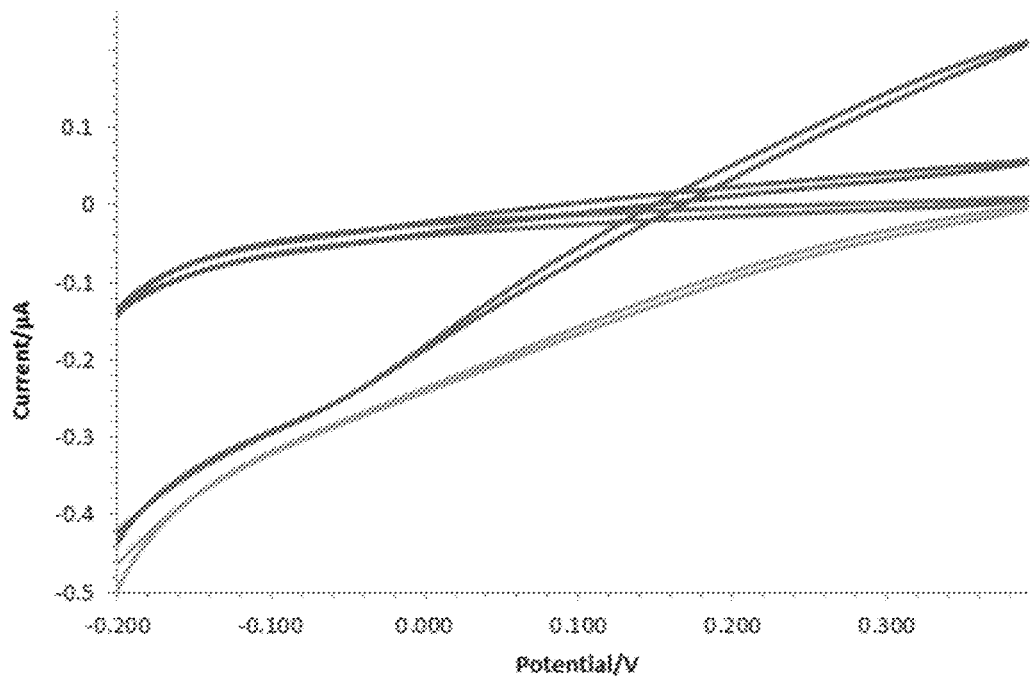
Figure 23C:
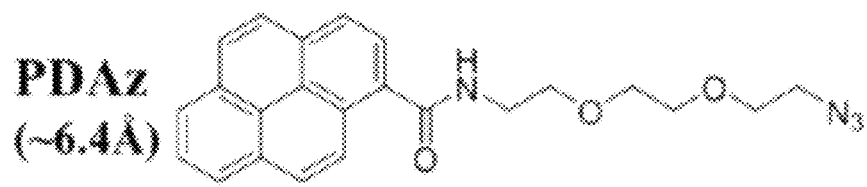
Figure 24A:
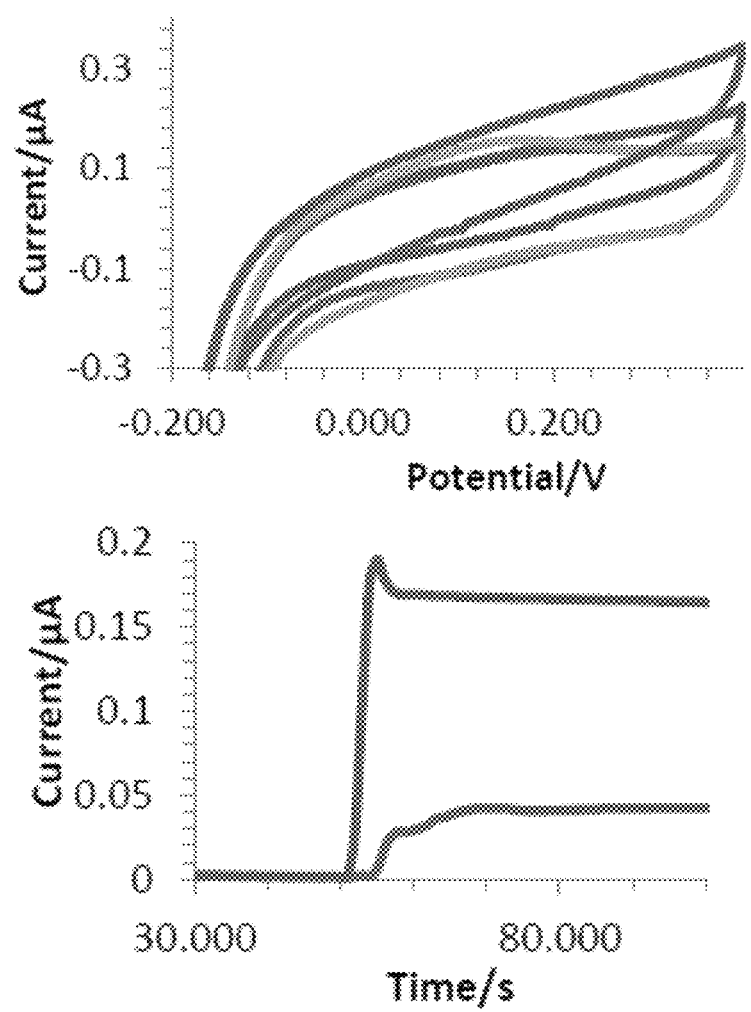
Figure 24B:
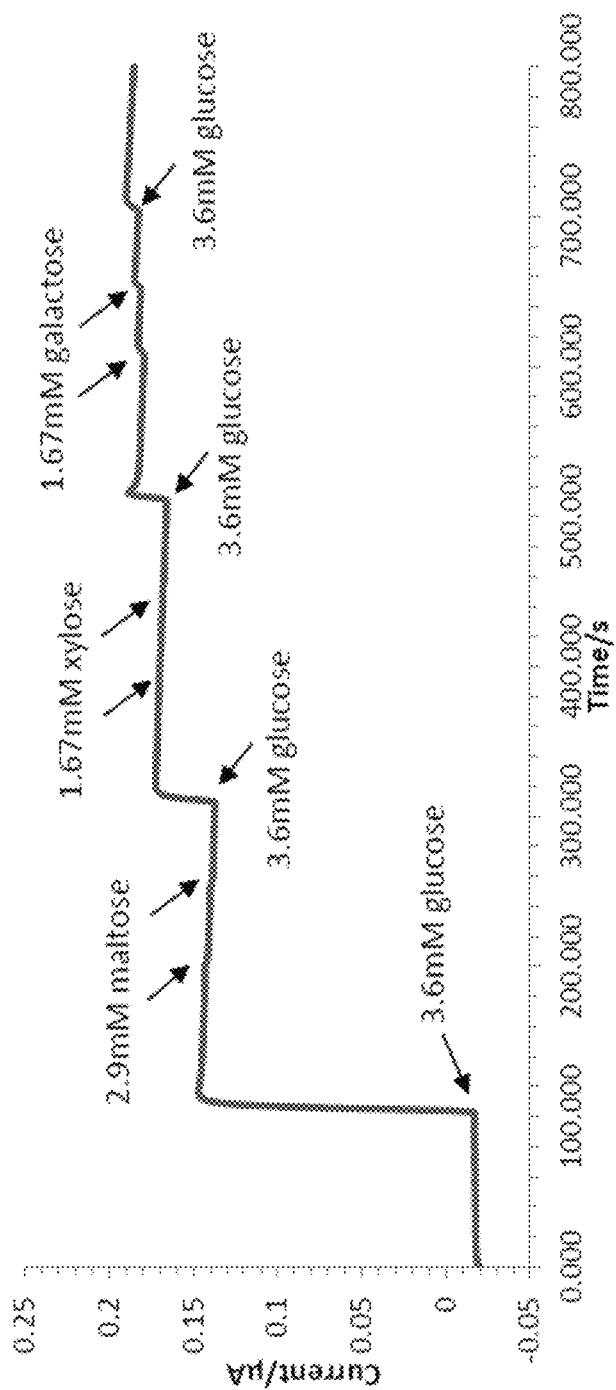
Figure 25:
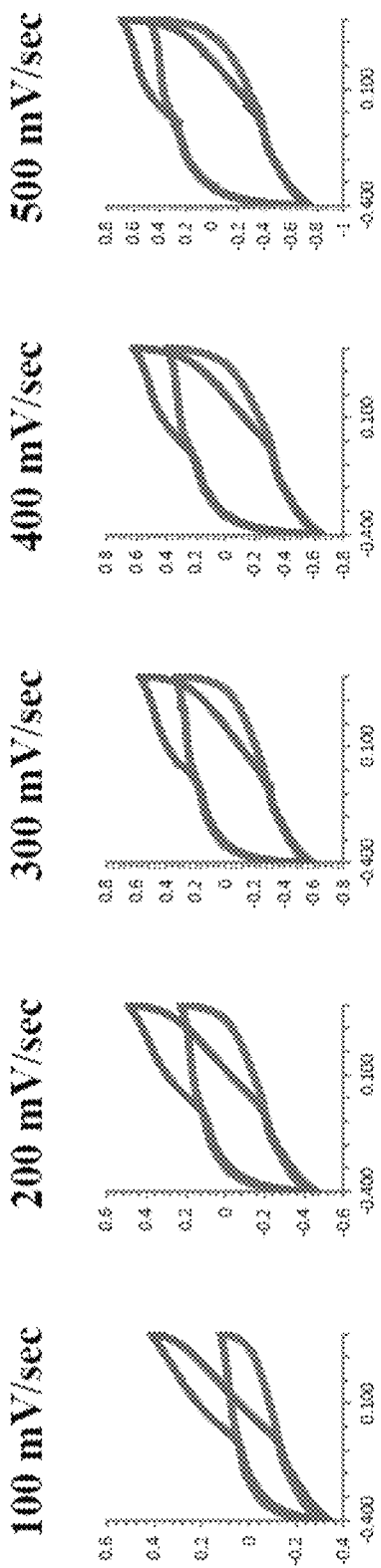

FIG. 13 presents gel micrograph verification of PrK incorporation using TAMRA-Az. 6 µM FGM-S247PrK, GDH-S247PrK and FGM-T558PrK were conjugate to TAMRA-Az using click reaction. The conjugated protein was loaded into SDS-PAGE and a fluorescent image of the gel was taken. PM2700 was used as the protein size marker;

FIG. 14 presents graphs showing cyclic voltammograms in different scan-rates in the absence of glucose and peak current vs. scan rate plots. An arrow marks the relevant peak of each variant. The relation between the peak current and the scan rate was analyzed by simple linear regression and the $R^2$ is presented;

FIGS. 15A-15B present plasmid maps of pec86-pylOTS plasmid (FIG. 15A) and pETDuet-FGMS247TAG expression plasmid (FIG. 15B);

FIG. 16 presents images of AFM measurements of highly oriented pyrolytic graphite (HOPG) after incubation using different linkers. Measurement of the height of the HOPG surface after incubation with acetate buffer (left panel), FGM-S247PDAz (middle panel) and FGM-S247PCA (right panel). The square and line on the right panel indicate the area which its height was analyzed and is presented in the graphs below the respective image, arrows indicate a single protein on the HOPG surface. 200 nm scale bars are represented by white lines. Representative 3D images of the same modified surfaces are present. All images are of the same scale and measured areas of 1 µm×1 µm;

FIG. 17 presents a graph of differential pulse voltammetry (DPV) curves of EDC-NHS+PCA coupling reaction mixture (1) and click reaction mixture (2) that lacks the protein sample. FGM-S247PCA (4) and FGM-S247PDAz (3) curves were added for the ease of comparison;

FIGS. 18A-18H present graphs of electrochemical characterization of wired FGM and GDH: DPV measurements of FGM-S247PDAz (2) and FGM-S247PCA (1) under argon in the absence of glucose (FIG. 18A). Peaks are indicated by arrows; linearized multistep amperometry current decay plot of FGM-S247PDAz (circle), FGM-T558PDAz (diamond), GDH-S247PDAz (triangle) and FGM-S247PCA (square) (FIG. 18B); CVs of FGM-S247PDAz, FGM-T558PDAz, GDH-S247PDAz and FGM-S247PCA in high scan rates before (1) and after (4, 5, 3 and 2, respectively) the addition of 5 mM glucose (FIG. 18C); CV of heme-binding domain attached to the electrode surface before (1) and after (2) the addition of 5 mM of glucose (FIG. 18D); CVs in scan rate of 10 mV/sec for FGM-S247PDAz, FGM-T558PDAz, GDH-S247PDAz and FGM-S247PCA before the addition of 5 mM glucose (1), and after the addition of 5 mM glucose (3, 5, 4 and 2, respectively) (FIG. 18E); Glucose-current calibration curves of FGM-S247PCA (circle), FGM-S247PDAz (square), FGM-T558PDAz (triangle) and GDH-S247PDAz (inverted triangle) measured using chronoamperometric detection upon application of a potential of 300 mV vs. Ag/AgCl reference electrode. The current from each glucose concentration (10 µM-10 mM) was measured in triplicates; curves of the mean currents are presented with standard deviations. Inset presents the current response of FGM-T558PDAz towards glucose in physiologically relevant glucose concentrations of sweat and tears (FIG. 18F); FGM-T558PDAz response to glucose in ALU interference solution that was measured upon application of 150 mV vs. Ag/AgCl reference electrode. Black arrows indicate 0.1 mM glucose additions (FIG. 18G); and the current response of FGM-T558PDAz in physiologically relevant range of glucose in the presence of interfering molecules. The current was measured in triplicates and the mean current values were used for the linear regression and are presented with error bars (FIG. 18H);

FIGS. 19A-19B present graphs of linear range of FGM-T558PDAz (FIG. 19A) and FGM-S247PCA (FIG. 19B) current response towards glucose;

FIG. 20 presents anti-his tag Western blot analysis of FGM expressed from pTrc plasmid (1) vs. the use of a pETDuet plasmid (2);

FIG. 21 presents FGM 3D model structure with arrows indicating the ncAA incorporation sites;

FIGS. 22A-22C present ncAA incorporated FGM variants characterization: FGM variants after 'click' with a fluorescent marker (FIG. 22A), in-gel heme staining of protein concentrated elution samples (FIG. 22B) and a graph of FAD-GDH glucose oxidation activity assay (FIG. 22C);

FIGS. 23A-23C present site-specific 'wiring' verification: Cyclic voltammetry (CV) of electrodes after incubation with a 'clicked' FGM and S247PrKFGM using a pyrene-azide linker (FIG. 23A); FGM—blue and red curves, S247PrKFGM—green and purple curves; CV of 'clicked' S247PrKFGM vs. S247PrKFGM entrapped under a dialysis membrane. Entrapped enzymes: blue and red curves, 'clicked' enzymes: green and purple curves (FIG. 23B); and pyrene-di-ethylene oxide-azide linker chemical structure (FIG. 23C);

FIG. 24A-24B present click reaction effect on S247PrKFGM: CV of S247PrKFGM+pDAz no glucose (green), S247PrKFGM+pDAz 5 mM glucose (purple), S247PrKFGM without pDAz no glucose (blue), S247PrKFGM without pDAz 5 mM glucose (red); and chronoamperometry of S247PrKFGM without pDAz (blue), S247PrKFGM+pDAz (red) (FIG. 24A) and S247PrKFGMpDAz specificity test (FIG. 24B); and FIG. 25 presents CV of S247PrKFGM response to 5 mM glucose in different scan rates.

DETAILED DESCRIPTION OF THE INVENTION

Provided herein is a recombinant flavin-adenine dinucleotide glucose dehydrogenase (FAD-GDH) enzyme, polynucleotides sequences encoding same, useful for direct electron transfer such as in bio-electrochemical applications, including, but not limited to, glucose monitoring.

The present invention is directed to a polypeptide comprising a non-canonical amino acid (ncAA). According to some embodiments, the present invention provides an electrode coupled to the polypeptide of the present invention.

The present invention is based, in part, on the surprising finding that using a site-specific incorporation of the ncAA, allows for a of a specific orientation towards the electrode. By controlling the incorporation of the ncAA and orientation, the catalytic current can be improved in response to glucose.

In some embodiments, the wiring of the polypeptides through different sites result in a significant effect on their electron transfer (ET) characteristics and their ability to communicate with an electrode. In some embodiments, the site-specific wiring of the polypeptides allows higher catalytic currents and lower onset potential, indicating highly efficient ET that is gained due to the site-specific wiring.

As provided in some embodiments of the present invention, fusing the enzyme with a minimal cytochrome domain (MCD), instead of large cytochrome, allows to shorten the enzyme-electrode distance and improve the direct electron transfer (DET) capabilities of the enzyme. As demonstrated hereinbelow under a non-limiting example, the fusion enzyme communicated with an electrode directly, without the use of a mediator molecule. Direct electron transfer between the redox enzyme and an electrode resulted in enhancement of chemical detection.

As demonstrated hereinbelow, the disclosed recombinant enzyme showed a substantially reduced redox potential, e.g., from +400 mV to 0 mV, thereby improving enzyme selectivity in various electrochemical applications including glucose sensing and monitoring as well as an electromotive force in a bio-electrochemical power device.

Before explaining further embodiments of the invention in detail, it is to be understood that the invention is not necessarily limited in its application to the details set forth in the following description or exemplified by the Examples. The invention is capable of other embodiments or of being practiced or carried out in various ways.

Polypeptides

According to some embodiments, there is provided a recombinant polypeptide comprising the amino acid sequence: MADTDTQKADVVVVGSGVAGAI-VAHQLAMAGKSVILLEAGPRMPRWEIVER-FRNQVDKTD FMAPYPSSAWAPHPEYGPPN-DYLILKGEHKFNSQYIRAVGGT TWHWAASAWRFIPNDFKMK TVYGVGRDWPIQYDD-IEHYYQRAEEELGVWGPGPEEDLYSPRKEPYPMP-PLPLSFNEQTIKSA LNGYDPKFHVVTEPVARN-SRPYDGRPTCCGNNNCMPICPIGA MYNGIVHVEKAEQAGAKLID XAVVYKLETGPDKRI-TAAVYKDKTGADHRVEGKYFVIAANGIETPKILLM-SANRDFPNGVAN SSDMVGRNLMDHPGTGVSFYA-NEKLWPGRGPQEMTSLIGFRDG PFRANEAAKKIHLSNMSRI NQETQKIFKGGKLMKPEELDAQIRDR-SARFVQFDCFHEILPQPENRIVPSKTATDAVGIPRPEIT YAIDDYVKRGAVHTREVYATAAKVLGGTEVVFNDE-FAPNNHITGATIMGADARDSVVDKDC RAFDHPNLFISSSSTMPTVGTVNVTLTIAALA-LRMSDTLKKEVEFGSGYGSGPPGPIRAGATMP HRDRGPCGACHAIIQ (SEQ ID NO: 20), wherein X is a non-canonical amino acid (ncAA).

According to some embodiments, there is provided a recombinant polypeptide comprising the amino acid sequence: MADTDTQKADVVVVGSGVAGAI-VAHQLAMAGKSVILLEAGPRMPRWEIVER-FRNQVDKTD FMAPYPSSAWAPHPEYGPPN-DYLILKGEHKFNSQYIRAVGGTT WHWAASAWRFIPNDFKMK TVYGVGRDWPIQYDD-IEHYYQRAEEELGVWGPGPEEDLYSPRKEPYPMP-PLPLSFNEQTIKSA LNGYDPKFHVVTEPVARN-SRPYDGRPTCCGNNNCMPICPIGA MYNGIVHVEKAEQAGAKLID SAVVYKLETGPDKRI-TAAVYKDKTGADHRVEGKYFVIAANGIETPKILLM-SANRDFPNGVAN SSDMVGRNLMDHPGTGVSFYA-NEKLWPGRGPQEMTSLIGFRDGPFRANEA AKKIHLSNMSRI NQETQKIFKGGKLMKPEELDAQIRDR-SARFVQFDCFHEILPQPENRIVPSKTATDAVGIPRPEIT YAIDDYVKRGAVHTREVYATAAKVLGGTEVVFNDE-FAPNNHITGATIMGADARDSVVDKDC RAFDHPNLFISSSSTMPTVGTVNVTLTIAALA-LRMSDTLKKEVEFGSGYGSGPPGPIRAGAXMP HRDRGPCGACHAIIQ (SEQ ID NO: 20), wherein X is a non-canonical amino acid (ncAA).

In some embodiments, the ncAA comprises Propargyl-lysine (PrK).

In some embodiments, the ncAA is covalently bound to a mediator molecule comprising polycyclic aromatic system.

In some embodiments, the ncAA is covalently bound to a mediator molecule, wherein the mediator molecule is represented by Formula I:

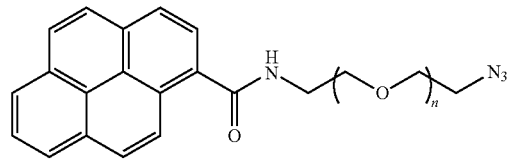

(I), wherein n is an integer in a range from 1 to 5.

In some embodiments, n is an integer in a range from 1 to 4, 1 to 3, 2 to 5, 2 to 4, or 2 to 3, including any range therebetween. Each possibility represents a separate embodiment of the invention.

In some embodiments, n equals 3. In some embodiments, n equals 2.

As used herein, the terms "polypeptide", "peptide" and "protein" are used interchangeably to refer to two or more amino acids linked together. The terms "polypeptide", "peptide", "protein", and "amino acid sequence" as used herein refer to any compound comprising naturally occurring or synthetic amino acid polymers or amino acid-like molecules including but not limited to compounds comprising amino and/or imino molecules. No particular size is implied by use of the term "peptide", "oligopeptide", "polypeptide", or "protein". Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring (e.g., synthetic). Thus, synthetic oligopeptides, dimers, multimers (e.g., tandem repeats, multiple antigenic peptide (MAP) forms, linearly-linked peptides), cyclized, branched molecules and the like, are included within the definition.

Polynucleotides

According to some embodiments, the present invention provides a polynucleotide comprising a nucleic acid sequence encoding the polypeptide described herein.

In some embodiments, the polynucleotide comprises the nucleic acid sequence set forth in SEQ ID NO: 15 or SEQ ID NO: 17.

In some embodiments, the polynucleotide comprises the nucleic acid sequence:

```
                                        (SEQ ID NO: 15)
ATGGCGGATACGGATACCCAGAAAGCGGACGTGGTCGTGGTTGGATCCG

GCGTGGCAGGCGCAATCGTGGCTCATCAACTGGCAATGGCAGGTAAAAG

CGTGATCCTGCTGGAAGCTGGTCCGCGTATGCCGCGTTGGGAAATTGTT

GAACGTTTCCGCAATCAAGTCGATAAAACCGACTTTATGGCACCGTATC

CGAGCAGCGCATGGGCACCGCATCCGGAATATGGTCCGCCGAATGATTA

CCTGATCCTGAAAGGCGAACACAAATTTAACTCACAGTACATTCGTGCA

GTGGGCGGCACCACGTGGCATTGGGCAGCCTCGGCATGGCGCTTCATCC
```

-continued
CGAACGATTTTAAAATGAAAACCGTGTATGGCGTTGGTCGTGACTGGCC

GATTCAGTACGATGACATCGAACATTATTACCAACGCGCGGAAGAAGAA

CTGGGCGTGTGGGGTCCGGGCCCGGAAGAAGACCTGTATTCACCGCGTA

AAGAACCGTACCCGATGCCGCCGCTGCCGCTGAGTTTCAATGAACAAAC

CATTAAATCCGCTCTGAACGGCTATGATCCGAAATTTCACGTGGTTACG

GAACCGGTGGCCCGTAATTCGCGCCCGTACGACGGTCGCCCGACCTGCT

GTGGCAACAATAACTGCATGCCGATTTGTCCGATCGGTGCAATGTATAA

CGGCATCGTCCATGTGGAAAAAGCTGAACAGGCAGGTGCTAAACTGATT

GATTAGGCGGTCGTGTACAAACTGGAAACGGGCCCGGACAAACGTATTA

CCGCAGCTGTTTATAAAGATAAAACGGGTGCGGACCATCGCGTCGAAGG

CAAATACTTCGTGATTGCGGCCAATGGTATCGAAACCCCGAAAATTCTG

CTGATGAGCGCGAACCGTGATTTTCCGAATGGTGTGGCCAACAGTTCCG

ATATGGTTGGCCGCAATCTGATGGACCATCCGGGCACCGGCGTGAGCTT

TTATGCAAACGAAAAACTGTGGCCGGGTCGTGGTCCGCAGGAAATGACC

TCTCTGATCGGTTTCCGTGATGGCCCGTTTCGCGCGAATGAAGCAGCGA

AGAAAATTCATCTGTCAAATATGTCGCGTATCAACCAGGAAACCCAAAA

AATCTTTAAAGGCGGTAAACTGATGAAACCGGAAGAACTGGATGCGCAG

ATCCGTGACCGCAGTGCCCGCTTTGTTCAATTCGATTGCTTTCACGAAA

TCCTGCCGCAGCCGGAAAATCGTATTGTCCCGTCCAAAACCGCAACGGA

CGCAGTGGGTATTCCGCGTCCGGAAATTACGTATGCGATCGATGACTAC

GTCAAACGTGGCGCAGTGCATACGCGCGAAGTTTATGCTACCGCGGCCA

AAGTGCTGGGCGGCACCGAAGTGGTCTTCAACGATGAATTTGCGCCGAA

TAACCACATCACCGGTGCCACGATTATGGGCGCGGATGCCCGTGACTCA

GTGGTTGATAAAGACTGTCGCGCCTTCGATCATCCGAACCTGTTTATTA

GCAGCAGCAGCACCATGCCGACGGTTGGCACCGTTAACGTCACCCTGAC

GATTGCAGCTCTGGCACTGCGTATGTCTGATACGCTGAAAAAAGAAGTC

GAATTCGGTTCTGGTTATGGCTCTGGTCCGCCGGGTCCGATTCGTGCAG

GTGCTACCATGCCGCATCGTGATCGTGGTCCGTGCGGTGCATGTCACGC

TATTATCCAGGGCAGTGGTTCCGGCCATCACCATCACCATCACTAA.

In some embodiments, the polynucleotide comprises the nucleic acid sequence:

(SEQ ID NO: 17)
ATGGCGGATACGGATACCCAGAAAGCGGACGTGGTCGTGGTTGGATCCG

GCGTGGCAGGCGCAATCGTGGCTCATCAACTGGCAATGGCAGGTAAAAG

CGTGATCCTGCTGGAAGCTGGTCCGCGTATGCCGCGTTGGGAAATTGTT

GAACGTTTCCGCAATCAAGTCGATAAAACCGACTTTATGGCACCGTATC

CGAGCAGCGCATGGGCACCGCATCCGGAATATGGTCCGCCGAATGATTA

CCTGATCCTGAAAGGCGAACACAAATTTAACTCACAGTACATTCGTGCA

GTGGGCGGCACCACGTGGCATTGGGCAGCCTCGGCATGGCGCTTCATCC

CGAACGATTTTAAAATGAAAACCGTGTATGGCGTTGGTCGTGACTGGCC

GATTCAGTACGATGACATCGAACATTATTACCAACGCGCGGAAGAAGAA

-continued
CTGGGCGTGTGGGGTCCGGGCCCGGAAGAAGACCTGTATTCACCGCGTA

AAGAACCGTACCCGATGCCGCCGCTGCCGCTGAGTTTCAATGAACAAAC

CATTAAATCCGCTCTGAACGGCTATGATCCGAAATTTCACGTGGTTACG

GAACCGGTGGCCCGTAATTCGCGCCCGTACGACGGTCGCCCGACCTGCT

GTGGCAACAATAACTGCATGCCGATTTGTCCGATCGGTGCAATGTATAA

CGGCATCGTCCATGTGGAAAAAGCTGAACAGGCAGGTGCTAAACTGATT

GATAGTGCGGTCGTGTACAAACTGGAAACGGGCCCGGACAAACGTATTA

CCGCAGCTGTTTATAAAGATAAAACGGGTGCGGACCATCGCGTCGAAGG

CAAATACTTCGTGATTGCGGCCAATGGTATCGAAACCCCGAAAATTCTG

CTGATGAGCGCGAACCGTGATTTTCCGAATGGTGTGGCCAACAGTTCCG

ATATGGTTGGCCGCAATCTGATGGACCATCCGGGCACCGGCGTGAGCTT

TTATGCAAACGAAAAACTGTGGCCGGGTCGTGGTCCGCAGGAAATGACC

TCTCTGATCGGTTTCCGTGATGGCCCGTTTCGCGCGAATGAAGCAGCGA

AGAAAATTCATCTGTCAAATATGTCGCGTATCAACCAGGAAACCCAAAA

AATCTTTAAAGGCGGTAAACTGATGAAACCGGAAGAACTGGATGCGCAG

ATCCGTGACCGCAGTGCCCGCTTTGTTCAATTCGATTGCTTTCACGAAA

TCCTGCCGCAGCCGGAAAATCGTATTGTCCCGTCCAAAACCGCAACGGA

CGCAGTGGGTATTCCGCGTCCGGAAATTACGTATGCGATCGATGACTAC

GTCAAACGTGGCGCAGTGCATACGCGCGAAGTTTATGCTACCGCGGCCA

AAGTGCTGGGCGGCACCGAAGTGGTCTTCAACGATGAATTTGCGCCGAA

TAACCACATCACCGGTGCCACGATTATGGGCGCGGATGCCCGTGACTCA

GTGGTTGATAAAGACTGTCGCGCCTTCGATCATCCGAACCTGTTTATTA

GCAGCAGCAGCACCATGCCGACGGTTGGCACCGTTAACGTCACCCTGAC

GATTGCAGCTCTGGCACTGCGTATGTCTGATACGCTGAAAAAAGAAGTC

GAATTCGGTTCTGGTTATGGCTCTGGTCCGCCGGGTCCGATTCGTGCAG

GTGCTTAGATGCCGCATCGTGATCGTGGTCCGTGCGGTGCATGTCACGC

TATTATCCAGGGCAGTGGTTCCGGCCATCACCATCACCATCACTAA.

In some embodiments, the polynucleotide comprises the nucleic acid sequence:

(SEQ ID NO: 7)
TAATACGACTCACTATAGGGGAATTGTGAGCGGATAACAATTCCCCTCT

AGAAATAATTTTGTTTAACTTTAAGAAGGAGATATACCATGGGCAGCCA

TGGCTCACAATGACAACACCCCGCACTCCCGCCGTACCGGCGATGCGGC

CGTGACCGGTATTACGCGTCGCCAGTGGCTGCAAGGCGCGCTGGCCCTG

ACCGCAGCTGGCCTGACGGGTTCCCTGGCCCTGCGCGCACTGGCTGATG

ATCCGGGCACCGCACCGCTGGATACCTTTATGACGCTGAGCGAAGCTCT

GACGGGCAAAAAGGTCTGTCTCGTGTTCTGGGCCAGCGTTTTCTGCAA

GCGCTGCAAAAAGGTTCATTCAAAACCGCGGATTCGCTGCCGCAGCTGG

CGGGCGCCCTGGCAAGCGGTTCTCTGAACCCGGACCAAGAAGCTCTGGC

GCTGAAAATCCTGGAAGCATGGTATCTGGGCATTGTTGATAATGTGGTT

-continued
```
ATCACCTACGAAGAAGCCCTGATGTTTAGTGTCGTGTCCGACACGCTGG
TCATTCCGAGCTATTGCCCGAACAAACCGGGTTTCTGGGCCGAAAAACC
GATCGAACGTCAGGCATAATGGCAGCCATCACCATCATCACCACAGCCA
GGATCCGAATTCGAGCTCGGCGCGCCTGCAGGTCGACAAGCTTGCGGCC
GCATAATGCTTAAGTCGAACAGAAAGTAATCGTATTGTACACGGCCGCA
TAATCGAAATTAATACGACTCACTATAGGGGAATTGTGAGCGGATAACA
ATTCCCCATCTTAGTATATTAGTTAAGTATAAGAAGGAGATATACATAT
GGCAGATCTCAATTGATGGCGGATACGGATACCCAGAAAGCGGACGTGG
TCGTGGTTGGATCCGGCGTGGCAGGCGCAATCGTGGCTCATCAACTGGC
AATGGCAGGTAAAAGCGTGATCCTGCTGGAAGCTGGTCCGCGTATGCCG
CGTTGGGAAATTGTTGAACGTTTCCGCAATCAAGTCGATAAAACCGACT
TTATGGCACCGTATCCGAGCAGCGCATGGGCACCGCATCCGGAATATGG
TCCGCCGAATGATTACCTGATCCTGAAAGGCGAACACAAATTTAACTCA
CAGTACATTCGTGCAGTGGGCGGCACCACGTGGCATTGGGCAGCCTCGG
CATGGCGCTTCATCCCGAACGATTTTAAAATGAAAACCGTGTATGGCGT
TGGTCGTGACTGGCCGATTCAGTACGATGACATCGAACATTATTACCAA
CGCGCGGAAGAAGAACTGGGCGTGTGGGTCCGGGCCCGAAGAAGACC
TGTATTCACCGCGTAAAGAACCGTACCCGATGCCGCCGCTGCCGCTGAG
TTTCAATGAACAAACCATTAAATCCGCTCTGAACGGCTATGATCCGAAA
TTTCACGTGGTTACGGAACCGGTGGCCCGTAATTCGCGCCCGTACGACG
GTCGCCCGACCTGCTGTGGCAACAATAACTGCATGCCGATTTGTCCGAT
CGGTGCAATGTATAACGGCATCGTCCATGTGGAAAAAGCTGAACAGGCA
GGTGCTAAACTGATTGATAGTGCGGTCGTGTACAAACTGGAAACGGGCC
CGGACAAACGTATTACCGCAGCTGTTTATAAAGATAAAACGGGTGCGGA
CCATCGCGTCGAAGGCAAATACTTCGTGATTGCGGCCAATGGTATCGAA
ACCCCGAAAATTCTGCTGATGAGCGCGAACCGTGATTTTCCGAATGGTG
TGGCCAACAGTTCCGATATGGTTGGCCGCAATCTGATGGACCATCCGGG
CACCGGCGTGAGCTTTTATGCAAACGAAAAACTGTGGCCGGGTCGTGGT
CCGCAGGAAATGACCTCTCTGATCGGTTTCCGTGATGGCCCGTTTCGCG
CGAATGAAGCAGCGAAGAAAATTCATCTGTCAAATATGTCGCGTATCAA
CCAGGAAACCCAAAAAATCTTTAAAGGCGGTAAACTGATGAAACCGGAA
GAACTGGATGCGCAGATCCGTGACCGCAGTGCCCGCTTTGTTCAATTCG
ATTGCTTTCACGAAATCCTGCCGCAGCCGGAAAATCGTATTGTCCCGTC
CAAAACCGCAACGGACGCAGTGGGTATTCCGCGTCCGGAAATTACGTAT
GCGATCGATGACTACGTCAAACGTGGCGCAGTGCATACGCGCGAAGTTT
ATGCTACCGCGGCCAAAGTGCTGGGCGGCACCGAAGTGGTCTTCAACGA
TGAATTTGCGCCGAATAACCACATCACCGGTGCCACGATTATGGGCGCG
GATGCCCGTGACTCAGTGGTTGATAAAGACTGTCGCGCCTTCGATCATC
CGAACCTGTTTATTAGCAGCAGCAGCACCATGCCGACGGTTGGCACCGT
TAACGTCACCCTGACGATTGCAGCTCTGGCACTGCGTATGTCTGATACG
CTGAAAAAGAAGTCGAATTCGGTTCTGGTTATGGCTCTGGTCCGCCGG
GTCCGATTCGTGCAGGTGCTACCATGCCGCATCGTGATCGTGGTCCGTG
CGGTGCATGTCACGCTATTATCCAGGGCAGTGGTTCCGGCCATCACCAT
CACCATCACTAAAAGCGATATCGGCCGGCCACGCGATCGCTGACGTCGG
TACCCTCGAGTCTGGTAAAGAAACCGCTGCTGCGAAATTTGAACGCCAG
CACATGGACTCGTCTACTAGCGCAGCTTAATTAACCTAGGCTGCTGCCA
CCGCTGAGCAATAACTAGCATAACCCCTTGGGGCCTCTAAACGGGTCTT
G.
```

The terms "polynucleotide" and "nucleic acid" as used interchangeably herein, refer to polymers of nucleotides of any length, and include DNA and RNA, or any combination thereof.

Polynucleotides encoding polypeptides may be obtained from any source including, but not limited to, a cDNA library prepared from tissue believed to possess the polypeptide mRNA and to express it at a detectable level. Accordingly, polynucleotides encoding a polypeptide can be conveniently obtained from a cDNA library prepared from human tissue. The polypeptide-encoding gene may also be obtained from a genomic library or by known synthetic procedures (e.g., automated nucleic acid synthesis).

In some embodiments, the polynucleotide is codon optimized to facilitate or increase translation efficiency in a host cell. In some embodiments, the polynucleotide is codon optimized for expression in a microorganism cell. Methods for codon optimization are common and would be apparent to one of ordinary skill in the art, as well as codon preference of various types of cells, e.g., of E. coli.

In some embodiments, there is provided a polynucleotide comprising: (a) a first regulatory element operably linked to the alpha catalytic subunit of the FGM expression gene; and (b) a second regulatory element operably linked to the gamma catalytic subunit of the FGM expression gene.

In some embodiments, the regulatory element is a promoter.

In some embodiments, the first regulatory element and the second regulatory element are identical. In some embodiments, the first regulatory element and the second regulatory element is a bacteriophage. In some embodiments, the first regulatory element and the second regulatory element is a T7 phage.

In some embodiments, the polynucleotide is a DNA molecule.

According to some embodiments, there is provided a vector or a plasmid comprising the polynucleotide of the invention.

In some embodiments, the expression vector or plasmid further comprises a nucleic acid sequence encoding a gamma subunit of an FAD-GDH.

In some embodiments, each of the polynucleotide encoding the polypeptide of the invention, and the nucleic acid sequence encoding the gamma subunit of an FAD-GDH are operably linked to a separate regulatory element.

In some embodiments, the expression vector further comprises a nucleic acid sequence encoding a gamma subunit of an FAD-GDH, wherein each of the polynucleotide encoding the polypeptide of the present invention, and the nucleic acid sequence encoding the gamma subunit of an FAD-GDH are operably linked to a separate regulatory element. In some embodiments, the regulatory element is a promoter. In some embodiments, the promoter is a T7 promoter.

According to some embodiments, there is provided a transgenic or a transfected cell comprising: a) the polypeptide disclosed herein; b) the polynucleotide disclosed herein; c) the expression vector or the plasmid disclosed herein; or d) any combination of (a) to (c).

In some embodiments, the cell is a prokaryotic cell. In one embodiment, the cell is a bacterial cell.

According to some embodiments, there is provided an extract obtained or derived from the cell disclosed herein. In some embodiments, the extract comprises: a) the polypeptide disclosed herein; b) the polynucleotide disclosed herein; c) the expression vector or the plasmid disclosed herein; d) any combination of (a) to (c).

According to some embodiments, there is provided a composition comprising: a) the polypeptide disclosed herein; b) the polynucleotide disclosed herein; c) the expression vector or the plasmid disclosed herein; d) the cell disclosed herein; e) the extract disclosed herein; f) any combination of (a) to (e); and g) and an acceptable carrier.

According to some embodiments, there is provided an electrode coupled to the polypeptide described herein. In some embodiments, coupled is by non-covalent interactions. In some embodiments, non-covalent interactions refer to pi-pi stacking interactions between the pyrene groups of the mediator molecule represented by Formula I and the electrode surface. As used herein "pi-pi stacking" refers to attractive, non-covalent interactions between aromatic rings.

According to some embodiments, there is provided a device comprising the electrode described hereinabove.

According to some embodiments, there is provided a method for determining an analyte in a liquid medium, the analyte being capable to undergo a biocatalytic oxidation or reduction reaction in the presence of an oxidizer or a reducer, respectively, the method comprising: (i) providing the device described hereinabove; (ii) contacting the device with the liquid medium; (iii) measuring the electric signal generated between the cathode and the anode, the electric signal being indicative of the presence and/or the concentration of the analyte; and (iv) determining the analyte based on the electric signal.

In some embodiments, the analyte comprises glucose.

According to some embodiments, there is provided a method for transferring an electron to an electrode, comprising coupling the polypeptide described herein to an electrode, thereby transferring an electron to the electrode.

According to some embodiments, there is provided a method for quantifying the amount of a reporter in a sample having a first detectable range of light absorbance in an oxidized state a second range of light absorbance in a non-oxidized state, comprising: (a) contacting polypeptide described herein with the reporter in a non-oxidized state; and (b) measuring the amount of the reporter in an oxidized state, thereby quantifying the amount of a reporter in a sample.

In some embodiments, the first detectable range of light absorbance is detectable in visible light and the second range of light absorbance is non-detectable in visible light. In some embodiments, the reporter is 2,6-Dichloroindophenol. In some embodiments, the 2,6-Dichloroindophenol is coupled to glucose.

According to some embodiments, there is provided a method for expression of the polypeptide described herein, comprising expressing a first subunit from a first regulatory element and expressing a second subunit from a second regulatory element, thereby expressing the polypeptide described herein.

In some embodiments, a first subunit is an alpha catalytic subunit of the FGM. In some embodiments, a second subunit is a gamma catalytic subunit of the FGM.

In some embodiments, the regulatory element is a promoter.

In some embodiments, the first regulatory element and the second regulatory element are identical. In some embodiments, the first regulatory element and the second regulatory element is a bacteriophage. In some embodiments, the first regulatory element and the second regulatory element is a T7 phage.

The present invention provides, in some embodiments, a recombinant protein comprising: (a) an alpha subunit of an FAD-GDH; and (b) a minimal cytochrome peptide.

In one embodiment, the alpha subunit of the FAD-GDH is derived or recovered from a prokaryotic cell. In one embodiment, the alpha subunit of the FAD-GDH is derived or recovered from a bacterial cell. In one embodiment, the alpha subunit of the FAD-GDH is *Burkholderia cepacian* alpha subunit of FAD-GDH. In one embodiment, the alpha subunit of the FAD-GDH of the present invention is derived from a thermostable enzyme, an oxygen independent enzyme, or both.

The term "thermostable enzyme" refers to an enzyme that is relatively stable to heat. The thermostable enzymes can withstand the high temperature incubation used to remove the modifier groups, typically, but not exclusively, greater than 50° C., without suffering an irreversible loss of activity.

In one embodiment, the recombinant protein further comprises the gamma subunit of an FAD-GDH. In one embodiment, the invention provides a composition comprising or consisting the recombinant protein with or without the gamma subunit of an FAD-GDH. In one embodiment, the invention provides a composition comprising or consisting the recombinant protein and the gamma subunit of an FAD-GDH. In one embodiment, the invention provides a composition comprising or consisting at least two different proteins: (a) the recombinant protein; and (b) the gamma subunit of an FAD-GDH. In one embodiment, the at least two different proteins are unbound. In some embodiments, the gamma subunit is from the same FAD-GDH as the alpha subunit. In some embodiments, the gamma subunit is from a different FAD-GDH as the alpha subunit. In some embodiments, the gamma subunit is from the same or different FAD-GDH as the alpha subunit.

In one embodiment, the recombinant protein further comprises a minimal cytochrome peptide. In one embodiment, the minimal cytochrome peptide is a natural peptide. In one embodiment, the minimal cytochrome peptide comprises a non-natural peptide.

In one embodiment, the recombinant protein is devoid of the gamma subunit of the FAD-GDH. In one embodiment, the minimal cytochrome peptide comprises a c-type cytochrome domain. In one embodiment, the minimal cytochrome peptide does not comprise a b-type cytochrome domain. In one embodiment, the minimal cytochrome peptide comprises a c-type cytochrome domain MCR-2 from a MamP protein. In one embodiment, the minimal cytochrome peptide comprises a magnetotactic bacterius minimal cytochrome peptide. In one embodiment, the minimal cytochrome peptide is a magnetotactic bacterius minimal cytochrome peptide.

In one embodiment, the minimal cytochrome peptide is a peptide comprising or consisting of 11 to 30 amino acids. In one embodiment, the minimal cytochrome peptide is a peptide comprising or consisting of 11 to 24 amino acids. In some embodiments, the minimal domain is a naturally occurring cytochrome. In some embodiments, the minimal domain is a synthetic cytochrome.

In one embodiment, the minimal cytochrome peptide is a cytochrome peptide (e.g., c-type cytochrome) comprising or consisting of 11, 12, 13, 14, 15, 16, 17, 18, 19, 20, 21, 22, 23, 24, 25, 26, 27, 28, 29, or 30 amino acids, including any range therebetween. In some embodiments, the peptide comprises cytochrome functionality. In some embodiments, the peptide comprises ET functionality.

In one embodiment, the minimal cytochrome peptide is linked to the amino terminus of the alpha subunit of an FAD-GDH. In one embodiment, the minimal cytochrome peptide is linked to the carboxy terminus of the alpha subunit of an FAD-GDH. In one embodiment, the minimal cytochrome peptide is linked to the amino terminus of the gamma subunit of an FAD-GDH. In one embodiment, the minimal cytochrome peptide is linked to the carboxy terminus of the gamma subunit of an FAD-GDH.

In one embodiment, the minimal cytochrome peptide is linked to the subunit of an FAD-GDH directly or indirectly. In one embodiment, the minimal cytochrome peptide is linked to the carboxy terminus of the subunit of an FAD-GDH directly or indirectly.

In one embodiment, the recombinant protein, further comprises a linker. In one embodiment, the recombinant protein, further comprises a peptide linker. In one embodiment, the minimal cytochrome peptide is linked to the carboxy terminus or the amino terminus of the alpha subunit of an FAD-GDH via a peptide linker. In one embodiment, the minimal cytochrome peptide is linked to the carboxy terminus or the amino terminus of the gamma subunit of an FAD-GDH via a peptide linker.

In one embodiment, the minimal cytochrome peptide is linked to the amino or carboxy terminus of the subunit via a linker comprising or consisting 5 to 20 amino acids. In one embodiment, the minimal cytochrome peptide is linked to the amino or carboxy terminus of the subunit via a linker comprising or consisting 8 to 18 amino acids. In one embodiment, the minimal cytochrome peptide is linked to the amino or carboxy terminus of the subunit via a linker comprising or consisting 12 to 15 amino acids. In one embodiment, the minimal cytochrome peptide is linked to the amino or carboxy terminus of the subunit via a linker comprising or consisting 5 to 15 amino acids. In some embodiments, the linker is between 1 and 10, 1 and 9, 1 and 8, 1 and 7, 2 and 10, 2 and 9, 2 and 8, 2 and 7, 3 and 10, 3 and 9, 2 and 8 or 2 and 7 amino acids in length.

In some embodiments, the linker comprises 30% to 60% glycine. In some embodiments, the linker comprises 30% to 60% serine. In some embodiments, the linker is hydrophilic. In some embodiments, the linker does not cause steric hinderance. In some embodiments, the linker is a flexible linker. In some embodiments, the linker does not interfere with maturation of the porphyrin binding MCD. In some embodiments, the linker does not interfere with enzymatic activity of the other subunits. In some embodiments, the linker is not so short that the other subunit interferes with maturation of the porphyrin binding MCD. In some embodiments, the linker retains the subunits in close enough proximity to allow electron transfer. In some embodiments, the linker has a length of up to 20 Å, up to 25 Å, or up to 30 Å. In some embodiments, the linker has a length of greater than or equal to 5 Å, 10 Å, 12 Å, 15 Å or 17 Å. Non-limiting exemplary linker is a peptide comprising GSGYGSG (SEQ ID NO: 27). In some embodiments, the linker comprises or consists of SEQ ID NO: 24. In some embodiments, the linker comprises or consists a non-peptide backbone.

In one embodiment, the linker is encoded by a DNA sequence comprising or consisting the nucleotide sequence: GAATTCGGTTCTGGT-TATGGCTCTGGTCCGCCGGGTCCG (SEQ ID NO: 4). It will be understood by a skilled artisan that synonymous substitutions may be made to this sequence.

In one embodiment, the linker is encoded by a DNA sequence comprising or consisting of a nucleotide sequence synonymous with SEQ ID NO: 4).

Without being bound by any particular mechanism it is assumed that a short linker containing glycine renders the linker with a desired flexibility. Further, and without being bound by any particular mechanism it is assumed that a short linker containing serine renders the linker with a desired hydrophilicity.

Further, a shorter linker (e.g. shorter than to 5 Å) could prevent proper maturation of the porphyrin binding MCD (due to its close proximity to GDH); on the other hand, a longer linker (e.g., longer than 30 Å) could prevent efficient ET between the two domains.

In one embodiment, the recombinant protein further comprises a short tag peptide (3 to 20 amino acids long). In one embodiment, the short tag peptide is his tag. In some embodiments, the tag is a 6×his tag. Protein tags are well known in the art and any tag that does not interfere with the function (redox and ET) of the recombinant protein may be used. In some embodiments, the short tag is between 1 and 30, 1 and 25, 1 and 20, 1 and 15, 1 and 10, 2 and 30, 2 and 25, 2 and 20, 2 and 25, 2 and 10, 3 and 30, 3 and 25, 3 and 20, 3 and 15 or 3 and 10 amino acids in length. Each possibility represents a separate embodiment of the invention.

In one embodiment, the recombinant protein has a molecular weight in the range of 58 to 75 kDa. In one embodiment, the recombinant protein has a molecular weight in the range of 60 to 70 kDa. In one embodiment, the recombinant protein has a molecular weight in the range of 63 to 65 kDa. In one embodiment, the recombinant protein has a molecular weight in the range of 62 to 68 kDa. In one embodiment, the recombinant protein has a molecular weight in the range of 63 to 65 kDa.

In some embodiments, the amino acid sequence of the recombinant protein comprises or consists of the following sequence: MADTDTQKADVVVVGSGVAGAI-VAHQLAMAGKSVILLEAGPRMPRWEIVER-FRNQVDKTD FMAPYPSSAWAPHPEYGPPN-DYLILKGEHKFNSQYIRAVGGTTWH WAASAWRFIPNDFKMK TVYGVGRDWPIQYDDIE-HYYQRAEEELGVWGPGPEEDLYSPRKEPYPMP-PLPLSFNEQTIKSA LNGYDPKFHVVTEPVARN-SRPYDGRPTCCGNNNCMPICPIGAMYN GIVHVEKAEQAGAKLID SAVVYKLETGPDKRI-TAAVYKDKTGADHRVEGKYFVIAANGIETPKILLM-SANRDFPNGVAN SSDMVGRNLMDHPGTGVSFYA-NEKLWPGRGPQEMTSLIGFRDGPFRA NEAAKKIHLSNMSRI NQETQKIFKGGKLMKPEELDAQIRDR-SARFVQFDCFHEILPQPENRIVPSKTATDAVGIPRPEIT YAIDDYVKRGAVHTREVYATAAKVLGGTEVVFNDE-FAPNNHITGATIMGADARDSVVDKDC RAFDHPNLFISSSSTMPTVGTVNVTLTIAAL (SEQ ID NO: 8, shortened).

Herein throughout, in some embodiments, by "shortened" or "partial" it is meant to refer to without e.g., tag peptide, and/or a linker.

In some embodiments, the amino acid sequence of the recombinant protein comprises or consists of the following sequence: MADTDTQKADVVVVGSGVAGAI-VAHQLAMAGKSVILLEAGPRMPRWEIVER-FRNQVDKTD FMAPYPSSAWAPHPEYGPPN-DYLILKGEHKFNSQYIRAVGGTTW HWAASAWRFIPNDFKMK TVYGVGRDWPIQYDDIE-HYYQRAEEELGVWGPGPEEDLYSPRKEPYPMP-PLPLSFNEQTIKSA LNGYDPKFHVVTEPVARN-SRPYDGRPTCCGNNNCMPICPIGAMYN GIVHVEKAEQAGAKLID SAVVYKLETGPDKRI-TAAVYKDKTGADHRVEGKYFVIAANGIETPKILLM-SANRDFPNGVAN SSDMVGRNLMDHPGTGVSFYA-NEKLWPGRGPQEMTSLIGFRDG PFRANEAAKKIHLSNMSRI NQETQKIFKGGKLMKPEELDAQIRDR-SARFVQFDCFHEILPQPENRIVPSKTATDAVGIPRPEIT YAIDDYVKRGAVHTREVYATAAKVLGGTEVVFNDE-FAPNNHITGATIMGADARDSVVDKDC RAFDHPNLFISSSSTMPTVGTVNVTLTIAALA-LRMSDTLKKEVIRAGATMPHRDRGPCGACHA IIQ (SEQ ID NO: 9, full).

In some embodiments, the amino acid sequence of the recombinant protein comprises or consists of the following sequence: MADTDTQKADVVVVGSGVAGAI-VAHQLAMAGKSVILLEAGPRMPRWEIVER-FRNQVDKTD FMAPYPSSAWAPHPEYGPPN-DYLILKGEHKFNSQYIRAVGGTT WHWAASAWRFIPNDFKMK TVYGVGRDWPIQYDD-IEHYYQRAEEELGVWGPGPEEDLYSPRKEPYPMP-PLPLSFNEQTIKSA LNGYDPKFHVVTEPVARN-SRPYDGRPTCCGNNNCMPICPIGA MYNGIVHVEKAEQAGAKLID SAVVYKLETGPDKRI-TAAVYKDKTGADHRVEGKYFVIAANGIETPKILLM-SANRDFPNGVAN SSDMVGRNLMDHPGTGVSFYA-NEKLWPGRGPQEMTSLIGFR DGPFRANEAAKKIHLSNMSRI NQETQKIFKGGKLMKPEELDAQIRDR-SARFVQFDCFHEILPQPENRIVPSKTATDAVGIPRPEIT YAIDDYVKRGAVHTREVYATAAKVLGGTEVVFNDE-FAPNNHITGATIMGADARDSVVDKDC RAFDHPNLFISSSSTMPTVGTVNVTLTIAALA-LRMSDTLKKEVEFGSGYGSGPPGPIRAGATMP HRDRGPCGACHAIIQGSGSGHIIHH (SEQ ID NO: 10, full).

In some embodiments, the amino acid sequence of the recombinant protein comprises or consists of the following sequence: MADTDTQKADVVVVGSGVAGAI-VAHQLAMAGKSVILLEAGPRMPRWEIVER-FRNQVDKTD FMAPYPSSAWAPHPEYGPPN-DYLILKGEHKFNSQYIRAVGGTTWH WAASAWRFIPNDFKMK TVYGVGRDWPIQYDDIE-HYYQRAEEELGVWGPGPEEDLYSPRKEPYPMP-PLPLSFNEQTIKSA LNGYDPKFHVVTEPVARN-SRPYDGRPTCCGNNNCMPICPIG AMYNGIVHVEKAEQAGAKLID SAV-VYKLETGPDKRITAAVYKDKTGADHRVEGKYFVI-AANGIETPKILLMSANRDFPNGVAN SSDMVGRNLMDHPGTGVSFYA-NEKLWPGRGPQEMTSLIGFRDGPFRANEAAKKIHL-SNMSRI NQETQKIFKGGKLMKPEELDAQIRDR-SARFVQFDCFHEILPQPENRIVPSKTATDAVGIPRPEIT YAIDDYVKRGAVHTREVYATAAKVLGGTEVVFNDE-FAPNNHITGATIMGADARDSVVDKDC RAFDHPNLFISSSSTMPTVGTVNVTLTIAALA-LRMSDTLKKEVEFGSGYGSGPPGPIRAGATMP HRDRGPCGACHAIIQ (SEQ ID NO: 11, partial).

An Electrode

In some embodiments, there is provided an electrode carrying or coupled to a recombinant protein comprising A, B, C, and D, wherein: A is a cofactor of a redox enzyme; B is a redox enzyme; C is a linker moiety; and D is an electron transfer (ET) domain that is configured to transfer electrons between the electrode and A. In some embodiment the ET comprises a cytochrome.

In one embodiment, the A, B, C, and D are linked to each other under the following order: A-B-C-D.

In some embodiments, the cofactor, when not bound to a linker moiety, comprises at least one pair of hydroxyl groups.

In one embodiment, there is provided a device comprising the electrode.

In one embodiment, the electrode comprises a material selected from, without being limited thereto, graphite and glassy carbon electrode (GCE).

In one embodiment, the electrode is made of or coated by an electrically conducting substance, such as, without being limited thereto gold, platinum, silver, conducting glass such as indium tin oxide (ITO).

In one embodiment, by "chemically attach to" it is meant to refer to being attached via a covalent bond. As used herein, the term "coupled" refers to a physical attachment, such that the two are bonded together. In some embodiments, the bond is a covalent bond. In some embodiments, the bond is a synthetic bond. In some embodiments, the bond is a chemical bond.

In another embodiment, by "chemically attach to" it is meant to refer to being attached to ("wiring") the electrode via a synthetic linker (also referred "electrode linker" or "mediator molecule" or "mediator") being configured to link the recombinant protein to an electrode.

In one embodiment, the wiring can be obtained by a non-specific process, by using a chemical modification and conductive matrices such as, without limitation, graphene oxide and multi-walled carbon nanotubes.

In one embodiment, the wiring is a site-specific wiring, performed e.g., by inserting at least one non-canonical amino acid in a desired site of one of the groups (A to D) that, optionally, covalently links to a moiety that binds to an electrode as described herein.

Without being bound by any particular mechanism, it is assumed that the recombinant protein disclosed herein (e.g., in the form of A-B-C-D) allows direct electron transfer (DET) via a domain that affords DET, resulting in a "built in" redox mediator.

In some embodiments, in order to achieve an efficient DET, the distance between the enzyme's active site and the electrode is as short as a few Angstroms (e.g., 1 to 20 Å). In some embodiments, the distance is between 0-20, 0-19, 0-18, 0-17, 0-16, 0-15, 0-14, 0-13, 0-12, 0-11, 0-10, 1-20, 1-19, 1-18, 1-17, 1-16, 1-15, 1-14, 1-13, 1-12, 1-11, 1-10, 2-20, 2-19, 2-18, 2-17, 2-16, 2-15, 2-14, 2-13, 2-12, 2-11, 3-10, 3-20, 3-19, 3-18, 3-17, 3-16, 3-15, 3-14, 3-13, 3-12, 3-11, or 3-10 Å. Each possibility represents a separate embodiment of the invention.

In some embodiments, when linked to the enzyme, the ET domain is minimal so as not to introduce additional insulation to the system by a complex proteinaceous matrix. In some embodiments, the ET domain is linked by a flexible linker. As described herein, the flexibility allows avoiding interruption of the catalytic redox activity. In some embodiments, the minimal domain is not more than 10, 12, 15, 17, 20, 22, 25, 27, 30, 32, 35, 37, 40, 42, 45, 47 or 50 amino acids. Each possibility represents a separate embodiment of the invention.

Embodiments of "minimal domain" are described hereinabove e.g., for the c-type cytochrome.

In some embodiments, the cofactor is selected from, without being limited thereto, FAD, $NAD^+$, and $NADP^+$.

In one embodiment, the redox enzyme refers to an enzyme that can catalyze a redox reaction.

In one embodiment, the redox enzyme may be selected from, without being limited thereto, oxidase, dehydrogenase, and malic enzyme (e.g., malate dehydrogenase). In some embodiments, the redox enzyme is selected from an oxidase, a dehydrogenase, a reductase, a peroxidase, a glyoxalase, a hydroxylase and a malic enzyme. In some embodiments, the redox enzyme is sugar dehydrogenase. In some embodiments, the sugar is glucose. In some embodiments, enzyme is alcohol dehydrogenase.

In one embodiment, the redox enzyme in the immobilized group is characterized by a redox potential of less than 50 mV. In one embodiment, the redox enzyme in the immobilized group is characterized by a redox potential of 50 mV, 40 mV, 30 mV, 20 mV, 10 mV, 0 V, −10 mV, −20 mV, −30 mV, −40 mV, −50 mV, −60 mV, −70 mV, −80 mV, −90 mV, −100 mV, −110 mV, −120 mV, −130 mV, −140 mV, −150 mV, −160 mV, −170 mV, −180 mV, −190 mV, or −200 mV (induced potential vs. Ag/AgCl) including any value and range therebetween.

In one embodiment, the dehydrogenase is selected from, without being limited thereto, alcohol dehydrogenase, glutamic acid dehydrogenase, cholesterol dehydrogenase, aldehyde dehydrogenase, glucose dehydrogenase, fructose dehydrogenase, sorbitol dehydrogenase, lactate dehydrogenase, and glycerol dehydrogenase.

In one embodiment, the linker moiety comprises a peptide. In one embodiment, the peptide comprises serine. In one embodiment, the linker moiety comprises a short peptide e.g. having 5 to 20 amino acids, or 5 to 15 amino acids, e.g., 5, 6, 7, 8, 9, 10, 11, 12, 13, 14, or 15 amino acids, including any range therebetween. In some embodiments, the linker is selected from any embodiments of a linker described hereinabove. In some embodiments, the linker moiety is a flexible linker. In some embodiments, the linker moiety is hydrophilic. In some embodiments, the linker moiety is synthetic. In some embodiments, the linker moiety is not from cellobiose dehydrogenase. In some embodiments, the linker moiety is not from pyranose dehydrogenase. In some embodiments, the linker moiety does not interfere with enzyme function and/or DET.

A non-limiting example of a linker is a peptide comprising GSGYGSG.

In one embodiment, the linker is characterized by a length of: 5 to 40, or 20 to 30 Å, e.g., 5, 10, 15, 20, 25, 30, 35, or 40 Å, including any value and range therebetween.

In one embodiment, the electron transfer domain comprises a cytochrome, e.g., MCD.

Embodiments of the cytochrome are described hereinabove. In some embodiments, the electron transfer domain comprises a cytochrome c. In some embodiments, the electron transfer domain does not comprise a cytochrome b. In some embodiments, the recombinant protein is not a naturally occurring protein.

In one embodiment, the device is a biosensor.

As used herein and in the art, biosensors are analytical devices that combine a biological material (e.g., tissues, microorganisms, enzymes, antibodies, nucleic acids etc.) or a biologically-derived material with a physicochemical transducer or transducing microsystem.

In one embodiment, the device comprises or is configured to attach to an electronic circuitry for energizing the electrode and measuring the response.

In some embodiments, the biosensor is for measuring the concentration of a sugar in a medium.

In some embodiments, the biosensor is for measuring the concentration of glucose in a medium. In some embodiments, the biosensor is for measuring the concentration of alcohol in a medium.

In some embodiments the medium is a bodily fluid. In some embodiments, the bodily fluid is selected from at least one of: blood, serum, gastric fluid, intestinal fluid, saliva, bile, tumor fluid, urine, breast milk, interstitial fluid, and stool. In some embodiments, the biosensor is capable of measuring whole blood, serum or plasma glucose without dilution or sample processing, which can evaluate the current status of glucose or an individual suffering from diabetes. In some embodiments, the bodily fluid is undiluted. In some embodiments, the bodily fluid is diluted with a buffer.

In some embodiments, the biosensor comprises an anode compartment and a cathode compartment, the compartments being in fluid communication, wherein the anode compartment comprises an anode electrode and a substrate; and wherein the cathode compartment comprises a cathode electrode, the anode electrode and cathode electrode in electrical communication.

In some embodiments, the electrode disclosed herein is the anode.

According to an aspect, the present invention provides a method for determining an analyte in a liquid medium, the analyte being capable to undergo a biocatalytic oxidation or reduction reaction in the presence of an oxidizer or a reducer, respectively, the method comprising:
  (i) providing the disclosed device in an embodiment thereof,
  (ii) contacting the device with the liquid medium;
  (iii) measuring the electric signal generated between the cathode and the anode, the electric signal being indicative of the presence and/or the concentration of the analyte; and
  (iv) determining the analyte based on the electric signal.

In some embodiments, the method is for determining the presence of the analyte in the medium. In some embodiments, the method is for determining the concentration of the analyte in the medium. When the liquid medium is, for example, a body fluid e.g. blood, lymph fluid or cerebrospinal fluid, and the method may be carried out in an invasive manner, the method comprises inserting the biosensor into the body and bringing it into contact with the body fluid and determining the analyte in the body fluid within the body. Alternatively, body fluids or any other analyte may be tested non-invasively, and in such cases the method may comprise adding a buffer to the fluid. In some embodiments, the buffer has pH 4 to 8. In some embodiments, the buffer has pH 5 (±1).

In some embodiments, the contacting is in vivo. In some embodiments, the contacting is ex vivo. In some embodiments, a detected electrical signal indicates the analyte is present. In some embodiments, the greater the electrical signal the greater the concentration of analyte. In some embodiments, the electrical signal is compared to a predetermined standard that indicates the concentration of the analyte based on the electrical signal.

Non-limiting examples of analytes are sugar molecules e.g., galactose, lactose, maltose and xylose glucose, fructose, maltose; lactate; bilirubin; alcohols or amino acids.

In some embodiments, provided herein is a method for transferring an electron to an electrode, comprising coupling the disclosed recombinant protein in an embodiment thereof to an electrode, thereby transferring an electron to an electrode. In one embodiment, coupling is in the absence of a mediator molecule.

In some embodiments, the amino acid sequence of the recombinant protein comprises or consists of the following sequence: MADTDTQKADVVVVGSGVAGAIVAH QLAMAGKSVILLEAGPX$_1$MPRWEIVERFRNQVDKTD FMAPYPSSAWAPHPEYGPPNDYLILKGEHKFNSQYI-RAVGGTTWHWAASAWRFIPNDFKMK TVYGVGRDWPIQYDDIEHYYQRAEEELGVWGPG-PEEDLYSPRKEPYPMPPLPLSFNEQTIKSA LNGYDPKFHVVTEPVARNSRPYDGRPTCCGNNNCM-PICPIGAMYNGIVHVEKAEQAGAKLID X$_2$AVVYKLETGPDKRITAAVYKDKTGA DHRVEGKYFVIAANGIETPKILLMSANRDFPNGVA NSSDMVGRNLMDHPGTGVSFYA-NEKLWPGRGPQEMTSLIGFRDGPFRANEAAKKIHL-SNMS RINQETQKIFKGGKLMKPEELDA QIRX$_3$RSARFVQFDCFHEILPQPENR IVPSKTATDAVGIPRP EITYAIDDYVKRGAVHT-REVYATAAKVLGGTEVVFNDEFAPNNHITGATIMGA-DARDSVVDK DCRAFDHPNLFISSSSTMPTVGT VNVTLTIAALALRMSDTLKKEVEFGSGY GSGPPGPIRAGAX$_4$MX$_5$HRDRGPCGAC HAIIQGSGSGHHHIHIHH (SEQ ID NO: 12, full).

In some embodiments, the amino acid sequence of the recombinant protein comprises or consists of the following sequence: MADTDTQKADVVVVGSGVAGAI VAHQLAMAGKSVILLEAGPX$_1$MPRWE IVERFRNQVDKTD FMAPYPSSAWAPHPEYGPPN-DYLILKGEHKFNSQYIRAVGGTTWHWAA-SAWRFIPNDFKMK TVYGVGRDWPIQYDDIE-HYYQRAEEELGVWGPGPEEDLY SPRKEPYPMPPLPLSFNEQTIKSA LNGYDPKFHVVTEPVARNSRPYDGRPTCCGNNNCM-PICPIGAMYNGIVHVEKAEQAGAKLID X$_2$AVVYKLETGPDKRITAAV YKDKTGADHRVEGKYFVIAANGIETPKILLM-SANRDFPNGVA NSSDMVGRNLMDHPGTGVSFYA-NEKLWPGRGPQEMTSLIGFRDGPFRANEAAKKIHL-SNMS RINQETQKIFKGGKLMKPEELDAQIRX$_3$ RSARFVQFDCFHEILPQPENRIVPSKTATDAVGIPRP EITYAIDDYVKRGAVHTREVYATAAKVLGGTE-VVFNDEFAPNNHITGATIMGADARDSVVDK DCRAFDHPNLFISSSSTMPTVGTVNV TLTIAALALRMSDTLKKEVEFGSGYG SGPPGPIRAGAX$_4$MX$_5$HRDRGPCGACHAIIQ (SEQ ID NO: 13, partial).

In some embodiments, $X_1$ is R. In some embodiments, $X_2$ is S. In some embodiments, $X_3$ is D. In some embodiments, $X_4$ is T. In some embodiments, $X_5$ is P.

In some embodiments, one or more amino acids selected from $X_1$ to $X_5$ comprise at least one non-canonical amino acid (ncAA) residue.

Exemplary embodiments of SEQ ID NO: 12-13 are presented in the Examples section below (e.g., SEQ ID NOs: 19-23).

The term "non-canonical amino acid residue" refers to amino acid residues in D- or L-form that are not among the 20 canonical amino acids generally incorporated into naturally occurring proteins, for example, β-amino acids, homoamino acids, cyclic amino acids and amino acids with derivatized side chains.

Non-canonical amino acid residues may be incorporated into a peptide within the scope of the invention by employing known techniques of protein engineering that use recombinantly expressing cells.

In some embodiments one or more from $X_1$ to $X_5$ are present in proximity to the protein domain selected from, without being limited thereto: FAD binding domain, or MCD. In some embodiments one or more from $X_1$ to $X_5$ are present in a site that is distant from either FAD domain or MCD.

In some embodiments, by "proximity" it is meant to refer to a distance of 10 to 25 Å, e.g., 10, 15, 20, or 25 Å, including any value and range therebetween.

In some embodiments, by "distant" it is meant to refer to a distance of 30 to 100 Å, e.g., 10, 15, 20, 25, 30, 35, 40, 45, 50, 55, 60, 65, 70, 75, 80, 85, 90, 95, or 100 Å.

In some embodiments, the ncAA is a clickable ncAA.

By "clickable ncAA" it is meant to refer to ncAA attachable to another group or moiety by biorthogonal chemical mechanism.

In exemplary embodiments, the ncAA comprises Propargyl-lysine (PrK).

In some embodiments, the ncAA has attached thereto an electrode linker (mediator) configured to couple the recombinant protein to an electrode.

In some embodiments, the linker comprises an aromatic group.

In some embodiments, the aromatic group comprises polycyclic aromatic hydrocarbon system.

In some embodiments, by "polycyclic aromatic hydrocarbon system" it is meant to refer to a system comprising e.g., 3, 4, 5, or 6, fused benzene rings, which, in some embodiments, is in the form in a flat aromatic system.

In some embodiments, the aromatic group is selected from, without being limited thereto, pyrene, perylene, benzopyrene, oxoperylene, rubrene, perylene bisimide, styrene, anthracene, tetracene, pentacene, or any derivative thereof.

In exemplary embodiments, the aromatic group comprises pyrene or a derivative thereof.

In some embodiments, the linker further comprises an azide group.

In some embodiments, the azide group allows to bind to the PrK, for example, via an alkyne group, e.g., by "click" chemistry.

In some embodiments, the aromatic system (e.g., pyrene group) is present in one pole of the linker, and the azide group is present at the other pole of the mediator.

In some embodiments, the two groups (e.g., azide group and the aromatic group) are connected to each other by an alkyl oxide, for example, and without being limited thereto, tri-ethylene oxide, di-ethylene oxide or mono-ethylene oxide. In some embodiments, the mediator is characterized by a length of 3 to 9 or 4 to 8 Å, for example 3, 4, 5, 6, 7, 8, or 9 Å, including any value and range therebetween.

The Porphyrin

In one embodiment, the recombinant protein (e.g., the cytochrome domain) is bound to a porphyrin comprising a metal. In one embodiment, the recombinant protein is bound to a compound of formula I:

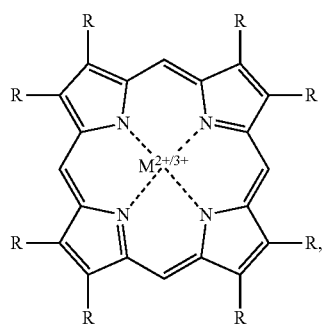

wherein R is any electron donor, or a compound as further described herein, wherein the compound of formula I is bound to a metal. In one embodiment, the recombinant protein but not the gamma subunit is bound to a porphyrin as described herein.

In one embodiment, R represents, independently and in each occurrence, a substituent selected from the group consisting of: alkyl, cycloalkyl, aryl, heteroalicyclic, heteroaryl, alkoxy, hydroxy, phosphonate, thiohydroxy, thioalkoxy, aryloxy, thioaryloxy, amino, nitro, halo, trihalomethyl, cyano, amide, amine, alkanoamine, carboxy, sulfonyl, sulfoxy, sulfinyl, and sulfonamide, or is absent. In one embodiment, R represents, independently and in each occurrence, hydrogen.

In one embodiment, R represents —$(C_1$-$C_6)$alkyl. In some embodiments, R represents —$(C_1$-$C_6)$alkoxy. In some embodiments, R represents —$(C_1$-$C_6)$alkylthio. In some embodiments, R represents —$(C_1$-$C_6)$alkylsulfinyl. In some embodiments, R represents —$(C_1$-$C_6)$alkylsulfonyl. In some embodiments, R represents —$[(C_1$-$C_6)$alkyl]NH. In some embodiments, R represents —$[(C_1$-$C_6)$alkyl]COOH.

In one embodiment, the term "alkyl" comprises an aliphatic hydrocarbon including straight chain and branched chain groups. Preferably, the alkyl group has 21 to 100 carbon atoms, and more preferably 21-50 carbon atoms. Whenever a numerical range; e.g., "21-100", is stated herein, it implies that the group, in this case the alkyl group, may contain 21 carbon atoms, 22 carbon atoms, 23 carbon atoms, etc., up to and including 100 carbon atoms.

In one embodiment, the term "long alkyl" comprises an alkyl having at least 20 carbon atoms in its main chain (the longest path of continuous covalently attached atoms). A short alkyl therefore has 20 or less main-chain carbons. In one embodiment, an alkyl can be substituted or unsubstituted. In one embodiment, the term "alkyl", as used herein, also encompasses saturated or unsaturated hydrocarbon, hence this term further encompasses alkenyl and alkynyl.

In one embodiment, the term "alkenyl" describes an unsaturated alkyl, as defined herein, having at least two carbon atoms and at least one carbon-carbon double bond. The alkenyl may be substituted or unsubstituted by one or more substituents, as described hereinabove. In one embodiment, the term "alkynyl", as defined herein, is an unsaturated alkyl having at least two carbon atoms and at least one carbon-carbon triple bond. The alkynyl may be substituted or unsubstituted by one or more substituents.

In one embodiment, the term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted.

In one embodiment, the term "aryl" describes an all-carbon monocyclic or fused-ring polycyclic (i.e., rings which share adjacent pairs of carbon atoms) groups having a completely conjugated pi-electron system. In one embodiment, an aryl group may be substituted or unsubstituted.

In one embodiment, the term alkoxy" describes both an —O-alkyl and an —O-cycloalkyl group. In one embodiment, the term "aryloxy" describes an —O-aryl. In one embodiment, the term alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule.

In one embodiment, "halide", "halogen" or "halo" describes fluorine, chlorine, bromine or iodine. In one embodiment, "haloalkyl" describes an alkyl group as defined herein, further substituted by one or more halide(s). In one embodiment, "haloalkoxy" describes an alkoxy group as defined herein, further substituted by one or more halide(s). In one embodiment, the term "hydroxyl" or "hydroxy" describes a —OH group. In one embodiment, the term "thiohydroxy" or "thiol" describes a —SH group. In one embodiment, the term "thioalkoxy" describes both an —S-alkyl group, and a —S-cycloalkyl group. In one embodiment, the term "thioaryloxy" describes both an —S-aryl and a —S-heteroaryl group. In one embodiment, the term "amine" describes a —NR'R" group, with R' and R". In one embodiment, the term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

In one embodiment, the term "heteroalicyclic" or "heterocyclyl" describes a monocyclic or fused ring group having in the ring(s) one or more atoms such as nitrogen, oxygen and sulfur. The rings may also have one or more double bonds. In one embodiment, the rings do not have a completely conjugated pi-electron system. Representative examples are piperidine, piperazine, tetrahydrofurane, tetrahydropyrane, morpholino and the like.

In one embodiment, the term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon).

In one embodiment, the term "carbonyl" describes a —C(=O)—R' group, where R' is as defined hereinabove. In one embodiment, the above-terms also encompass thio-derivatives thereof (thiocarboxy and thiocarbonyl).

In one embodiment, the term "thiocarbonyl" describes a —C(=S)—R' group, where R' is as defined hereinabove. In one embodiment, the term "thiocarboxy" group describes a —C(=S)—OR' group, where R' is as defined herein. In one embodiment, the term sulfinyl" group describes an —S(=O)—R' group, where R' is as defined herein. In one embodiment, the term sulfonyl" or "sulfonate" group describes an —S(=O)$_2$—R' group, where R' is as defined herein. In one embodiment, the term "carbamyl" or "carbamate" group describes an —OC(=O)—NR'R" group, where R' is as defined herein and R" is as defined for R'.

In one embodiment, the term "nitro" group refers to a —NO$_2$ group. In one embodiment, the term "cyano" or "nitrile" group refers to a —C≡N group. In one embodiment, the term azide" refers to a —N$_3$ group. In one embodiment, the term "sulfonamide" refers to a —S(=O)$_2$—NR'R" group, with R' and R" as defined herein.

In one embodiment, the term "phosphonyl" or "phosphonate" describes an —O—P(=O)(OR')$_2$ group, with R' as defined hereinabove. In one embodiment, the term "phosphinyl" describes a —PR'R" group, with R' and R" as defined hereinabove.

In one embodiment, the term "alkaryl" describes an alkyl, as defined herein, which substituted by an aryl, as described herein. In one embodiment, alkaryl is benzyl.

In one embodiment, the term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

In one embodiment, the terms "halo" and "halide", which are referred to herein interchangeably, describe an atom of a halogen, that is fluorine, chlorine, bromine or iodine, also referred to herein as fluoride, chloride, bromide and iodide. In one embodiment, the term "haloalkyl" describes an alkyl group as defined above, further substituted by one or more halide(s).

In one embodiment, the metal is a trivalent metal or a divalent metal.

In one embodiment, the recombinant protein as described herein comprises both peroxidase activity and oxidative activity. In one embodiment, the recombinant protein bound to a porphyrin comprising a metal comprises both peroxidase activity and oxidative activity. In one embodiment, the recombinant protein bound to a porphyrin comprising a metal comprises both peroxidase activity and oxidase activity.

In one embodiment, the recombinant protein is characterized by Michaelis-Menten constant $K_M^{app}$ value which is at least 2, 3, 4 or 5, or more, higher compared to plain GDH, as measured under the same condition (e.g., glucose concentration) of glucose oxidation.

In one embodiment, the recombinant protein is characterized by higher selectivity towards glucose oxidation as compared to other sugar's molecules. In one embodiment, the means that the rate of glucose oxidation is higher by at least 10%, by at least 20%, by at least 30%, by at least 40%, or by at least 50% than a other sugar molecule.

As used herein, the terms "peptide", "polypeptide" and "protein" are used interchangeably to refer to a polymer of amino acid residues. In some embodiment, the peptides, polypeptides and proteins described herein have modifications rendering them more stable while in the body or more capable of penetrating into cells. In some embodiment, the terms "peptide", "polypeptide" and "protein" apply to naturally occurring amino acid polymers. In another embodiment, the terms "peptide", "polypeptide" and "protein" apply to amino acid polymers in which one or more amino acid residue is an artificial chemical analogue of a corresponding naturally occurring amino acid.

As used herein, the term "recombinant protein" refers to protein which is coded for by a recombinant DNA, and is thus not naturally occurring. The term "recombinant DNA" refers to DNA molecules formed by laboratory methods of genetic recombination. Generally, this recombinant DNA is in the form of a vector used to express the recombinant protein in a cell. In one embodiment, the recombinant protein is provided within a single composition or kit with the gamma subunit FAD-GDH. In one embodiment, the recombinant protein with the gamma subunit FAD-GDH are provided within a single composition or kit as two separate proteins (unbound).

In some embodiments, the recombinant protein is a hybrid protein. In some embodiments, the recombinant protein is a chimeric protein. In some embodiments, the c-type cytochrome peptide is from a different protein than the alpha subunit. In some embodiments, the c-type cytochrome peptide is not from FAD-GDH. In some embodiments, the c-type cytochrome peptide is not from GDH. In some embodiments, the nucleic acid sequence encoding the alpha subunit and the sequence encoding the c-type cytochrome peptide are operably linked, such that a full-length protein is produced following translation and/or transcription. The term "operably linked" is intended to mean that the two nucleotide sequences of interest are linked to each other in a manner that allows for expression of the nucleotide sequence (e.g. in an in vitro transcription/translation system or in a host cell when the vector is introduced into the host cell).

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid" which refers to a circular double stranded DNA loop into which additional DNA segments can be inserted, such as by standard molecular cloning techniques. Another type of vector, wherein virally-derived DNA or RNA sequences are present in the virus (e.g. retroviruses, replication defective retroviruses, adenoviruses, replication defective adenoviruses, and adeno-associated viruses). Viral vectors also include polynucleotides carried by a virus for transfecting into host cells. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". Common expression vectors of utility in recombinant DNA techniques are often in the form of plasmids.

Recombinant expression vectors can comprise a nucleic acid coding for the protein of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

A vector or a plasmid is an artificial composite. A vector or a plasmid as described herein is man-made. A vector or a plasmid as described herein is not a product of nature.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

General methods in molecular and cellular biochemistry, such as may be useful for carrying out DNA and protein recombination, as well as other techniques described herein, can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (1 Lefkovits ed., Academic Press 1997); and Cell and Tissue Culture: Laboratory Procedures in Biotechnology (Doyle & Griffiths, John Wiley & Sons 1998).

It should be well understood to one skilled in the art that a recombinant protein is produced by expressing the recombinant DNA in a cell and then purifying the protein. The cells expressing the DNA are cultured under effective conditions, which allow for the expression of high amounts of recombinant polypeptide. Such effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

Purification of a recombinant protein involves standard laboratory techniques for extracting a recombinant protein that is essentially free from contaminating cellular components, such as carbohydrate, lipid, or other proteinaceous impurities associated with the peptide in nature. Purification can be carried out using a tag that is part of the recombinant protein or thought immuno-purification with antibodies directed to the recombinant protein. Kits are commercially available for such purifications and will be familiar to one skilled in the art. Typically, a preparation of purified peptide contains the peptide in a highly-purified form, i.e., at least about 80% pure, at least about 90% pure, at least about 95% pure, greater than 95% pure, or greater than 99% pure.

In some embodiments, the protein comprises an amino acid sequence with at least 60%, at least 65%, at least 70%, at least 75%, at least 80%, at least 85%, at least 90%, at least 95%, at least 99% homology to the amino acid sequence set forth below in SEQ ID NO: 1. In some embodiments, the amino acid sequence with at least 70% homology to SEQ ID NO: 1 is the amino acid sequence set forth in SEQ ID NO: 6.

Mutations and deletions in a recombinant protein are created by introducing the mutation or deletion into the recombinant DNA. Methods of site-directed mutagenesis, and routine DNA recombination can be found in such standard textbooks as are enumerated above. Mutagenesis of one amino acid to another may require mutation of 1, 2, or 3 of the bases that make up the codon corresponding to the amino acid to be changed.

In some embodiments, provided herein a method for quantifying the amount of a reporter in a sample having a first detectable range of light absorbance in an oxidized state a second range of light absorbance in a non-oxidized state and, comprising: contacting the recombinant protein with the reporter in a non-oxidized state; and measuring the amount of the reporter in an oxidized state, thereby quantifying the amount of a reporter in a sample. In some embodiments, coupled is directly bound. In another embodiment, first detectable range of light absorbance is detectable in visible light and the second range of light absorbance is non-detectable in visible light. In some embodiments, the reporter is 2,6-Dichloroindophenol. In some embodiments, the reporter is coupled to glucose. In some embodiments, 2,6-Dichloroindopheno is coupled to glucose.

DNA Sequences

In one embodiment, provided herein is a DNA molecule encoding the recombinant protein. In one embodiment, provided herein is a DNA molecule comprising: a transcription regulatory element, a translation regulatory element or both; operably linked to a nucleotide sequence encoding the recombinant protein. In one embodiment, the invention provides a DNA molecule encoding both the recombinant protein and the gamma subunit of an FAD-GDH. In one embodiment, the invention provides a single DNA molecule encoding both the recombinant protein and the gamma subunit of an FAD-GDH as two separate proteins.

In one embodiment, provided herein is a DNA molecule comprising a nucleic acid sequence encoding the recombinant protein. In one embodiment, provided herein is a DNA molecule comprising a nucleic acid sequence encoding the recombinant protein and the gamma subunit of an FAD-GDH. In one embodiment, provided herein is a DNA molecule comprising the nucleic acid sequence selected from the group consisting SEQ ID NOs: 5-7. In one embodiment, the invention provides a plasmid or a vector (such as an expression vector) comprising a nucleic acid sequence encoding the recombinant protein. In one embodiment, provided herein is a cell comprising a DNA molecule, a plasmid or a vector as described herein. In one embodiment, the cell is a prokaryotic cell. In one embodiment, the cell is a bacterial cell.

In one embodiment, the alpha subunit of the FAD-GDH is encoded by a DNA sequence comprising or consisting of the nucleotide sequence:

(SEQ ID NO: 1)
ATGGCGGATACGGATACCCAGAAAGCGGACGTGGTCGTGGTTGGATCCGG

CGTGGCAGGCGCAATCGTGGCTCATCAACTGGCAATGGCAGGTAAAAGCG

TGATCCTGCTGGAAGCTGGTCCGCGTATGCCGCGTTGGGAAATTGTTGAA

CGTTTCCGCAATCAAGTCGATAAAACCGACTTTATGGCACCGTATCCGAG

CAGCGCATGGGCACCGCATCCGGAATATGGTCCGCCGAATGATTACCTGA

TCCTGAAAGGCGAACACAAATTTAACTCACAGTACATTCGTGCAGTGGGC

GGCACCACGTGGCATTGGGCAGCCTCGGCATGGCGCTTCATCCCGAACGA

TTTTAAAATGAAAACCGTGTATGGCGTTGGTCGTGACTGGCCGATTCAGT

ACGATGACATCGAACATTATTACCAACGCGCGGAAGAAGAACTGGGCGTG

TGGGGTCCGGGCCCGGAAGAAGACCTGTATTCACCGCGTAAAGAACCGTA

CCCGATGCCGCCGCTGCCGCTGAGTTTCAATGAACAAACCATTAAATCCG

CTCTGAACGGCTATGATCCGAAATTTCACGTGGTTACGGAACCGGTGGCC

CGTAATTCGCGCCCGTACGACGGTCGCCCGACCTGCTGTGGCAACAATAA

CTGCATGCCGATTTGTCCGATCGGTGCAATGTATAACGGCATCGTCCATG

TGGAAAAAGCTGAACAGGCAGGTGCTAAACTGATTGATAGTGCGGTCGTG

TACAAACTGGAAACGGGCCCGGACAAACGTATTACCGCAGCTGTTTATAA

AGATAAAACGGGTGCGGACCATCGCGTCGAAGGCAAATACTTCGTGATTG

CGGCCAATGGTATCGAAACCCCGAAAATTCTGCTGATGAGCGCGAACCGT

GATTTTCCGAATGGTGTGGCCAACAGTTCCGATATGGTTGGCCGCAATCT

GATGGACCATCCGGGCACCGGCGTGAGCTTTTATGCAAACGAAAAACTGT

GGCCGGGTCGTGGTCCGCAGGAAATGACCTCTCTGATCGGTTTCCGTGAT

GGCCCGTTTCGCGCGAATGAAGCAGCGAAGAAAATTCATCTGTCAAATAT

GTCGCGTATCAACCAGGAAACCCAAAAAATCTTTAAAGGCGGTAAACTGA

TGAAACCGGAAGAACTGGATGCGCAGATCCGTGACCGCAGTGCCCGCTTT

GTTCAATTCGATTGCTTTCACGAAATCCTGCCGCAGCCGGAAAATCGTAT

TGTCCCGTCCAAAACCGCAACGGACGCAGTGGGTATTCCGCGTCCGGAAA

TTACGTATGCGATCGATGACTACGTCAAACGTGGCGCAGTGCATACGCGC

GAAGTTTATGCTACCGCGGCCAAAGTGCTGGGCGGCACCGAAGTGGTCTT

CAACGATGAATTTGCGCCGAATAACCACATCACCGGTGCCACGATTATGG

GCGCGGATGCCCGTGACTCAGTGGTTGATAAAGACTGTCGCGCCTTCGAT

CATCCGAACCTGTTTATTAGCAGCAGCAGCACCATGCCGACGGTTGGCAC

CGTTAACGTCACCCTGACGATTGCAGCTCTGGCACTGCGTATGTCTGATA

CGCTGAAAAAGAAGTC.

In one embodiment, the recombinant protein is encoded by a DNA molecule comprising a coding nucleotide sequence encoding the alpha subunit of the FAD-GDH.

In one embodiment, the alpha subunit of the FAD-GDH is encoded by a DNA sequence of 1200 to 1700 nucleotides. In one embodiment, the alpha subunit of the FAD-GDH is encoded by a DNA sequence of 1200 to 1650 nucleotides. In one embodiment, the alpha subunit of the FAD-GDH is encoded by a DNA sequence of 1300 to 1650 nucleotides. In one embodiment, the alpha subunit of the FAD-GDH is encoded by a DNA sequence of 1400 to 1700 nucleotides. In one embodiment, the alpha subunit of the FAD-GDH is encoded by a DNA sequence of 1500 to 1700 nucleotides. In one embodiment, the alpha subunit of the FAD-GDH is encoded by a DNA sequence of 1500 to 1650 nucleotides. In one embodiment, the alpha subunit of the FAD-GDH is encoded by a DNA sequence of 1550 to 1640 nucleotides. In one embodiment, the alpha subunit of the FAD-GDH is encoded by a DNA sequence of 1600 to 1650 nucleotides.

In one embodiment, the alpha subunit of the FAD-GDH is a mutant of alpha FAD-GDH or a mutant of SEQ ID NO: 1. Active mutants of alpha FAD-GDH or SEQ ID NO: 1 are readily available to one of skill in the art. By the term active mutant, as used in conjunction with an FAD-GDH, is meant a mutated form of the naturally occurring FAD-GDH. FAD-GDH mutant or variants will typically but not exclusively have at least 70%, e.g., 80%, 85%, 90% to 95% or more, and for example 98% or more amino acid sequence identity to the amino acid sequence of the reference FAD-GDH molecule.

In one embodiment, the DNA sequence of a mutant of FAD-GDH or a mutant of SEQ ID NO: 1 is at least 70% identical to SEQ ID NO: 1. In one embodiment, the DNA sequence of a mutant of FAD-GDH or a mutant of SEQ ID NO: 1 is at least 75% identical to SEQ ID NO: 1. In one embodiment, the DNA sequence of a mutant of FAD-GDH or a mutant of SEQ ID NO: 1 is at least 80% identical to SEQ ID NO: 1. In one embodiment, the DNA sequence of a mutant of FAD-GDH or a mutant of SEQ ID NO: 1 is at least 85% identical to SEQ ID NO: 1. In one embodiment, the DNA sequence of a mutant of FAD-GDH or a mutant of SEQ ID NO: 1 is at least 90% identical to SEQ ID NO: 1. In one embodiment, the DNA sequence of a mutant of FAD-GDH or a mutant of SEQ ID NO: 1 is at least 95% identical to SEQ ID NO: 1. In one embodiment, the DNA sequence of a mutant of FAD-GDH or a mutant of SEQ ID NO: 1 is at least 97% identical to SEQ ID NO: 1.

In one embodiment, the gamma subunit of the FAD-GDH is encoded by a DNA sequence comprising or consisting of the nucleotide sequence: ATGGCT-CACAATGACAACACCCCGCACTCCCG CCGTACCGGCGATGCGGCCGTGACCGGT ATTACGCGTCGCCAGTGGCTGCAAG GCGCGCTGGCCCTGACCGCAGCTGGCCTGACGGGT TCCCTGGCCCTGCGCGCACTGGCTGAT-GATCCGGGCACCGCACCGCTGGATACCTTTATG ACGCTGAGCGAAGCTCTGACGGGCAA AAAAGGTCTGTCTCGTGTTCTGGGCCAGCGTTTT CTGCAAGCGCTGCAAAAAGGTTCATT-CAAAACCGCGGATTCGCTGCCGCAGCTGGCGGGC GCCCTGGCAAGCGGTTCTCTGAACCCGGAC-CAAGAAGCTCTGGCGCTGAAAATCCTGGAA GCATGGTATCTGGGCATTGTTGATAATGTGGTTAT-CACCTACGAAGAAGCCCTGATGTTTA GTGTCGTGTCCGACACGCTGGTCATTCCGAGCTAT-TGCCCGAACAAACCGGGTTTCTGGG CCGAAAAACCGATCGAACGTCAGGCATAA (SEQ ID NO: 2).

In one embodiment, the gamma subunit of the FAD-GDH is translated into a discrete protein. In one embodiment, the gamma subunit of the FAD-GDH is encoded by a DNA sequence of 400 to 700 nucleotides. In one embodiment, the gamma subunit of the FAD-GDH is encoded by a DNA sequence of 450 to 650 nucleotides. In one embodiment, the gamma subunit of the FAD-GDH is encoded by a DNA sequence of 450 to 550 nucleotides. In one embodiment, the gamma subunit of the FAD-GDH is encoded by a DNA sequence of 480 to 530 nucleotides. In one embodiment, the gamma subunit of the FAD-GDH is encoded by a DNA sequence of 500 to 540 nucleotides. In one embodiment, the gamma subunit of the FAD-GDH is encoded by a DNA sequence of 500 to 530 nucleotides.

In one embodiment, the gamma subunit of the FAD-GDH is a mutant of gamma FAD-GDH or a mutant of SEQ ID NO: 2. In one embodiment, active mutants of gamma FAD-GDH or SEQ ID NO: 2 are readily available to one of skill in the art.

In one embodiment, the DNA sequence of a mutant of FAD-GDH or a mutant of SEQ ID NO: 2 is at least 70% identical to SEQ ID NO: 2. In one embodiment, the DNA sequence of a mutant of FAD-GDH or a mutant of SEQ ID NO: 2 is at least 75% identical to SEQ ID NO: 2. In one embodiment, the DNA sequence of a mutant of FAD-GDH or a mutant of SEQ ID NO: 2 is at least 80% identical to SEQ ID NO: 2. In one embodiment, the DNA sequence of a mutant of FAD-GDH or a mutant of SEQ ID NO: 2 is at least 85% identical to SEQ ID NO: 2. In one embodiment, the DNA sequence of a mutant of FAD-GDH or a mutant of SEQ ID NO: 2 is at least 90% identical to SEQ ID NO: 2. In one embodiment, the DNA sequence of a mutant of FAD-GDH or a mutant of SEQ ID NO: 2 is at least 95% identical to SEQ ID NO: 2. In one embodiment, the DNA sequence of a mutant of FAD-GDH or a mutant of SEQ ID NO: 2 is at least 97% identical to SEQ ID NO: 2.

In one embodiment, the minimal cytochrome peptide is encoded by a DNA sequence comprising or consisting of the nucleotide sequence: ATTCGTGCAGGTGCTAC-CATGCCGCATCGTGATCGTGGTCCGTGCGGTG-CATGTCACGCTA TTATCCAG (SEQ ID NO: 3).

In one embodiment, the recombinant protein is encoded by a DNA sequence comprising or consisting of the nucleotide sequence:

CTCACAATGACAACACCCCGCACTCCCGCCGTACCGGCGATGCGGCCGTG

ACCGGTATTACGCGTCGCCAGTGGCTGCAAGGCGCGCTGGCCCTGACCGC

AGCTGGCCTGACGGGTTCCCTGGCCCTGCGCGCACTGGCTGATGATCCGG

GCACCGCACCGCTGGATACCTTTATGACGCTGAGCGAAGCTCTGACGGGC

AAAAAAGGTCTGTCTCGTGTTCTGGGCCAGCGTTTTCTGCAAGCGCTGCA

AAAAGGTTCATTCAAAACCGCGGATTCGCTGCCGCAGCTGGCGGGCGCCC

TGGCAAGCGGTTCTCTGAACCCGGACCAAGAAGCTCTGGCGCTGAAAATC

CTGGAAGCATGGTATCTGGGCATTGTTGATAATGTGGTTATCACCTACGA

AGAAGCCCTGATGTTTAGTGTCGTGTCCGACACGCTGGTCATTCCGAGCT

ATTGCCCGAACAAACCGGGTTTCTGGGCCGAAAAACCGATCGAACGTCAG

GCATAATGGCGGATACGGATACCCAGAAAGCGGACGTGGTCGTGGTTGGA

TCCGGCGTGGCAGGCGCAATCGTGGCTCATCAACTGGCAATGGCAGGTAA

AAGCGTGATCCTGCTGGAAGCTGGTCCGCGTATGCCGCGTTGGGAAATTG

TTGAACGTTTCCGCAATCAAGTCGATAAAACCGACTTTATGGCACCGTAT

CCGAGCAGCGCATGGGCACCGCATCCGGAATATGGTCCGCCGAATGATTA

CCTGATCCTGAAAGGCGAACACAAATTTAACTCACAGTACATTCGTGCAG

-continued

TGGGCGGCACCACGTGGCATTGGGCAGCCTCGGCATGGCGCTTCATCCCG

AACGATTTTAAAATGAAAACCGTGTATGGCGTTGGTCGTGACTGGCCGAT

TCAGTACGATGACATCGAACATTATTACCAACGCGCGGAAGAAGAACTGG

GCGTGTGGGGTCCGGGCCCGGAAGAAGACCTGTATTCACCGCGTAAAGAA

CCGTACCCGATGCCGCCGCTGCCGCTGAGTTTCAATGAACAAACCATTAA

ATCCGCTCTGAACGGCTATGATCCGAAATTTCACGTGGTTACGGAACCGG

TGGCCCGTAATTCGCGCCCGTACGACGGTCGCCCGACCTGCTGTGGCAAC

AATAACTGCATGCCGATTTGTCCGATCGGTGCAATGTATAACGGCATCGT

CCATGTGGAAAAAGCTGAACAGGCAGGTGCTAAACTGATTGATAGTGCGG

TCGTGTACAAACTGGAAACGGGCCCGGACAAACGTATTACCGCAGCTGTT

TATAAAGATAAAACGGGTGCGGACCATCGCGTCGAAGGCAAATACTTCGT

GATTGCGGCCAATGGTATCGAAACCCGAAAATTCTGCTGATGAGCGCGA

ACCGTGATTTTCCGAATGGTGTGGCCAACAGTTCCGATATGGTTGGCCGC

AATCTGATGGACCATCCGGGCACCGGCGTGAGCTTTTATGCAAACGAAAA

ACTGTGGCCGGGTCGTGGTCCGCAGGAAATGACCTCTCTGATCGGTTTCC

GTGATGGCCCGTTTCGCGCGAATGAAGCAGCGAAGAAAATTCATCTGTCA

AATATGTCGCGTATCAACCAGGAAACCCAAAAAATCTTTAAAGGCGGTAA

ACTGATGAAACCGGAAGAACTGGATGCGCAGATCCGTGACCGCAGTGCCC

GCTTTGTTCAATTCGATTGCTTTCACGAAATCCTGCCGCAGCCGGAAAAT

CGTATTGTCCCGTCCAAAACCGCAACGGACGCAGTGGGTATTCCGCGTCC

GGAAATTACGTATGCGATCGATGACTACGTCAAACGTGGCGCAGTGCATA

CGCGCGAAGTTTATGCTACCGCGGCCAAAGTGCTGGGCGGCACCGAAGTG

GTCTTCAACGATGAATTTGCGCCGAATAACCACATCACCGGTGCCACGAT

TATGGGCGCGGATGCCCGTGACTCAGTGGTTGATAAAGACTGTCGCGCCT

TCGATCATCCGAACCTGTTTATTAGCAGCAGCAGCACCATGCCGACGGTT

GGCACCGTTAACGTCACCCTGACGATTGCAGCTCTGGCACTGCGTATGTC

TGATACGCTGAAAAAAGAAGTCATTCGTGCAGGTGCTACCATGCCGCATC

GTGATCGTGGTCCGTGCGGTGCATGTCACGCTATTATCCAG (SEQ ID

NO: 5 without linker, his and restriction sites).

In one embodiment, the recombinant protein is encoded by a DNA sequence comprising or consisting of the nucleotide sequence:

CTCACAATGACAACACCCCGCACTCCCGCCGTACCGGCGATGCGGCCGTG

ACCGGTATTACGCGTCGCCAGTGGCTGCAAGGCGCGCTGGCCCTGACCGC

AGCTGGCCTGACGGGTTCCCTGGCCCTGCGCGCACTGGCTGATGATCCGG

GCACCGCACCGCTGGATACCTTTATGACGCTGAGCGAAGCTCTGACGGGC

AAAAAAGGTCTGTCTCGTGTTCTGGGCCAGCGTTTTCTGCAAGCGCTGCA

AAAAGGTTCATTCAAAACCGCGGATTCGCTGCCGCAGCTGGCGGGCGCCC

TGGCAAGCGGTTCTCTGAACCCGGACCAAGAAGCTCTGGCGCTGAAAATC

CTGGAAGCATGGTATCTGGGCATTGTTGATAATGTGGTTATCACCTACGA

-continued
```
AGAAGCCCTGATGTTTAGTGTCGTGTCCGACACGCTGGTCATTCCGAGCT

ATTGCCCGAACAAACCGGGTTTCTGGGCCGAAAAACCGATCGAACGTCAG

GCATAATGGCGGATACGGATACCCAGAAAGCGGACGTGGTCGTGGTTGGA

TCCGGCGTGGCAGGCGCAATCGTGGCTCATCAACTGGCAATGGCAGGTAA

AAGCGTGATCCTGCTGGAAGCTGGTCCGCGTATGCCGCGTTGGGAAATTG

TTGAACGTTTCCGCAATCAAGTCGATAAAACCGACTTTATGGCACCGTAT

CCGAGCAGCGCATGGGCACCGCATCCGGAATATGGTCCGCCGAATGATTA

CCTGATCCTGAAAGGCGAACACAAATTTAACTCACAGTACATTCGTGCAG

TGGGCGGCACCACGTGGCATTGGGCAGCCTCGGCATGGCGCTTCATCCCG

AACGATTTTAAAATGAAAACCGTGTATGGCGTTGGTCGTGACTGGCCGAT

TCAGTACGATGACATCGAACATTATTACCAACGCGCGGAAGAAGAACTGG

GCGTGTGGGGTCCGGGCCCGGAAGAAGACCTGTATTCACCGCGTAAAGAA

CCGTACCCGATGCCGCCGCTGCCGCTGAGTTTCAATGAACAAACCATTAA

ATCCGCTCTGAACGGCTATGATCCGAAATTTCACGTGGTTACGGAACCGG

TGGCCCGTAATTCGCGCCCGTACGACGGTCGCCCGACCTGCTGTGGCAAC

AATAACTGCATGCCGATTTGTCCGATCGGTGCAATGTATAACGGCATCGT

CCATGTGGAAAAAGCTGAACAGGCAGGTGCTAAACTGATTGATAGTGCGG

TCGTGTACAAACTGGAAACGGGCCCGGACAAACGTATTACCGCAGCTGTT

TATAAAGATAAACGGGTGCGGACCATCGCGTCGAAGGCAAATACTTCGT

GATTGCGGCCAATGGTATCGAAACCCCGAAAATTCTGCTGATGAGCGCGA

ACCGTGATTTTCCGAATGGTGTGGCCAACAGTTCCGATATGGTTGGCCGC

AATCTGATGGACCATCCGGGCACCGGCGTGAGCTTTTATGCAAACGAAAA

ACTGTGGCCGGGTCGTGGTCCGCAGGAAATGACCTCTCTGATCGGTTTCC

GTGATGGCCCGTTTCGCGCGAATGAAGCAGCGAAGAAAATTCATCTGTCA

AATATGTCGCGTATCAACCAGGAAACCCAAAAAATCTTTAAAGGCGGTAA

ACTGATGAAACCGGAAGAACTGGATGCGCAGATCCGTGACCGCAGTGCCC

GCTTTGTTCAATTCGATTGCTTTCACGAAATCCTGCCGCAGCCGGAAAAT

CGTATTGTCCCGTCCAAAACCGCAACGGACGCAGTGGGTATTCCGCGTCC

GGAAATTACGTATGCGATCGATGACTACGTCAAACGTGGCGCAGTGCATA

CGCGCGAAGTTTATGCTACCGCGGCCAAAGTGCTGGGCGGCACCGAAGTG

GTCTTCAACGATGAATTTGCGCCGAATAACCACATCACCGGTGCCACGAT

TATGGGCGCGGATGCCCGTGACTCAGTGGTTGATAAAGACTGTCGCGCCT

TCGATCATCCGAACCTGTTTATTAGCAGCAGCAGCACCATGCCGACGGTT

GGCACCGTTAACGTCACCCTGACGATTGCAGCTCTGGCACTGCGTATGTC

TGATACGCTGAAAAAGAAGTCGAATTCGGTTCTGGTTATGGCTCTGGTC

CGCCGGGTCCGATTCGTGCAGGTGCTACCATGCCGCATCGTGATCGTGGT

CCGTGCGGTGCATGTCACGCTATTATCCAG (SEQ ID NO: 6 with linker and without his and restriction sites).
```

In one embodiment, the recombinant protein is encoded by a DNA sequence comprising or consisting of the nucleotide sequence: CCATGG

```
CCATGGCTCACAATGACAACACCCCGCACTCCCGCCGTACCGGCGATGCG

GCCGTGACCGGTATTACGCGTCGCCAGTGGCTGCAAGGCGCGCTGGCCCT

GACCGCAGCTGGCCTGACGGGTTCCCTGGCCCTGCGCGCACTGGCTGATG

ATCCGGGCACCGCACCGCTGGATACCTTTATGACGCTGAGCGAAGCTCTG

ACGGGCAAAAAGGTCTGTCTCGTGTTCTGGGCCAGCGTTTTCTGCAAGC

GCTGCAAAAAGGTTCATTCAAAACCGCGGATTCGCTGCCCGCAGCTGGCGG

GCGCCCTGGCAAGCGGTTCTCTGAACCCGGACCAAGAAGCTCTGGCGCTG

AAAATCCTGGAAGCATGGTATCTGGGCATTGTTGATAATGTGGTTATCAC

CTACGAAGAAGCCCTGATGTTTAGTGTCGTGTCCGACACGCTGGTCATTC

CGAGCTATTGCCCGAACAAACCGGGTTTCTGGGCCGAAAAACCGATCGAA

CGTCAGGCATAATGGCGGATACGGATACCCAGAAAGCGGACGTGGTCGTG

GTTGGATCCGGCGTGGCAGGCGCAATCGTGGCTCATCAACTGGCAATGGC

AGGTAAAAGCGTGATCCTGCTGGAAGCTGGTCCGCGTATGCCGCGTTGGG

AAATTGTTGAACGTTTCCGCAATCAAGTCGATAAAACCGACTTTATGGCA

CCGTATCCGAGCAGCGCATGGGCACCGCATCCGGAATATGGTCCGCCGAA

TGATTACCTGATCCTGAAAGGCGAACACAAATTTAACTCACAGTACATTC

GTGCAGTGGGCGGCACCACGTGGCATTGGGCAGCCTCGGCATGGCGCTTC

ATCCCGAACGATTTTAAAATGAAAACCGTGTATGGCGTTGGTCGTGACTG

GCCGATTCAGTACGATGACATCGAACATTATTACCAACGCGCGGAAGAAG

AACTGGGCGTGTGGGGTCCGGGCCCGGAAGAAGACCTGTATTCACCGCGT

AAAGAACCGTACCCGATGCCGCCGCTGCCGCTGAGTTTCAATGAACAAAC

CATTAAATCCGCTCTGAACGGCTATGATCCGAAATTTCACGTGGTTACGG

AACCGGTGGCCCGTAATTCGCGCCCGTACGACGGTCGCCCGACCTGCTGT

GGCAACAATAACTGCATGCCGATTTGTCCGATCGGTGCAATGTATAACGG

CATCGTCCATGTGGAAAAAGCTGAACAGGCAGGTGCTAAACTGATTGATA

GTGCGGTCGTGTACAAACTGGAAACGGGCCCGGACAAACGTATTACCGCA

GCTGTTTATAAAGATAAACGGGTGCGGACCATCGCGTCGAAGGCAAATA

CTTCGTGATTGCGGCCAATGGTATCGAAACCCCGAAAATTCTGCTGATGA

GCGCGAACCGTGATTTTCCGAATGGTGTGGCCAACAGTTCCGATATGGTT

GGCCGCAATCTGATGGACCATCCGGGCACCGGCGTGAGCTTTTATGCAAA

CGAAAAACTGTGGCCGGGTCGTGGTCCGCAGGAAATGACCTCTCTGATCG

GTTTCCGTGATGGCCCGTTTCGCGCGAATGAAGCAGCGAAGAAAATTCAT

CTGTCAAATATGTCGCGTATCAACCAGGAAACCCAAAAAATCTTTAAAGG

CGGTAAACTGATGAAACCGGAAGAACTGGATGCGCAGATCCGTGACCGCA

GTGCCCGCTTTGTTCAATTCGATTGCTTTCACGAAATCCTGCCGCAGCCG

GAAAATCGTATTGTCCCGTCCAAAACCGCAACGGACGCAGTGGGTATTCC

GCGTCCGGAAATTACGTATGCGATCGATGACTACGTCAAACGTGGCGCAG

TGCATACGCGCGAAGTTTATGCTACCGCGGCCAAAGTGCTGGGCGGCACC
```

```
-continued
GAAGTGGTCTTCAACGATGAATTTGCGCCGAATAACCACATCACCGGTGC

CACGATTATGGGCGCGGATGCCCGTGACTCAGTGGTTGATAAAGACTGTC

GCGCCTTCGATCATCCGAACCTGTTTATTAGCAGCAGCAGCACCATGCCG

ACGGTTGGCACCGTTAACGTCACCCTGACGATTGCAGCTCTGGCACTGCG

TATGTCTGATACGCTGAAAAAAGAAGTCGAATTCGGTTCTGGTTATGGCT

CTGGTCCGCCGGGTCCGATTCGTGCAGGTGCTACCATGCCGCATCGTGAT

CGTGGTCCGTGCGGTGCATGTCACGCTATTATCCAGGGCAGTGGTTCCGG

CCATCACCATCACCATCACTAAAAGCTT (SEQ ID NO: 7 with linker, his and restriction sites).
```

In one embodiment, the recombinant protein with or without the gamma subunit as described herein is encoded by a DNA sequence of 1500 to 3000 nucleotides. In one embodiment, the recombinant protein with or without the gamma subunit as described herein is encoded by a DNA sequence of 1600 to 2600 nucleotides. In one embodiment, the recombinant protein with or without the gamma subunit as described herein is encoded by a DNA sequence of 1800 to 2500 nucleotides. In one embodiment, the recombinant protein is encoded by a DNA sequence of 2000 to 2400 nucleotides.

In one embodiment, the recombinant protein is 350 to 700 amino acids long. In one embodiment, the recombinant protein is 220 to 600 amino acids long. In one embodiment, the recombinant protein is 250 to 550 amino acids long. In one embodiment, the recombinant protein is 450 to 850 amino acids long. In one embodiment, the recombinant protein is 470 to 750 amino acids long. In one embodiment, the recombinant protein is 500 to 700 amino acids long. In one embodiment, the recombinant protein is 710 to 780 amino acids long. In one embodiment, the recombinant protein is 500 to 600 amino acids long. In one embodiment, the recombinant protein is 520 to 580 amino acids long. In one embodiment, the recombinant protein is 350 to 550 amino acids long.

In one embodiment, a DNA sequence encoding the recombinant protein and the gamma subunit protein as described herein of SEQ ID NOs: 5 and 6 further comprises a Methionine codon (the initiation codon nucleotide sequence) 5' to SEQ ID NOs: 5 and/or 6. In one embodiment, a DNA sequence encoding the recombinant protein of SEQ ID NOs: 5 and 6 further comprises a Methionine codon (the initiation codon nucleotide sequence) 5' to SEQ ID NOs: 5 and/or 6. In one embodiment, a DNA sequence encoding the recombinant protein of SEQ ID NOs: 5 and 6 further comprises at its 5' end, a short DNA sequence comprising any 1-10 nucleotides sequence. In one embodiment, a DNA sequence encoding the recombinant protein of SEQ ID NOs: 5 and 6 further comprises at its 5' end, a short DNA sequence comprising 1-10 nucleotides sequence. In one embodiment, the 1-10 nucleotides sequence comprises the Methionine codon.

In one embodiment, a DNA sequence or molecule as described herein comprising a coding sequence encoding the recombinant protein, further encodes the gamma subunit protein as described herein (as a separate protein).

In one embodiment, the DNA sequence encoding the recombinant protein of the invention is any DNA molecule encoding the amino acid sequence encoded by anyone of SEQ ID NOs: 5-7 or the amino acid sequence of anyone of SEQ ID NOs: 8-11. In one embodiment, the DNA sequence encoding the recombinant protein with or without the gamma subunit as described herein is at least 70% identical to anyone of SEQ ID NOs: 5-7. In one embodiment, the DNA sequence encoding the recombinant protein with or without the gamma subunit as described herein is at least 75% identical to anyone of SEQ ID NOs: 5-7. In one embodiment, the DNA sequence encoding the recombinant protein with or without the gamma subunit as described herein is at least 80% identical to anyone of SEQ ID NOs: 5-7. In one embodiment, the DNA sequence encoding the recombinant protein with or without the gamma subunit as described herein is at least 85% identical to anyone of SEQ ID NOs: 5-7. In one embodiment, the DNA sequence encoding the recombinant protein with or without the gamma subunit as described herein is at least 90% identical to anyone of SEQ ID NOs: 5-7. In one embodiment, the DNA sequence encoding the recombinant protein with or without the gamma subunit as described herein is at least 95% identical to anyone of SEQ ID NOs: 5-7. In one embodiment, the DNA sequence encoding the recombinant protein with or without the gamma subunit as described herein is at least 95% identical to anyone of SEQ ID NOs: 5-7.

In some embodiments, a DNA molecule of the invention or a DNA sequence described herein comprises or consists any sequence encoding the recombinant protein including (but not limited to) the recombinant protein comprising or consisting anyone of SEQ ID NOs: 8-11. In some embodiments, a DNA molecule of the invention or a DNA sequence described herein comprises or consists any sequence encoding the recombinant protein and the gamma subunit, as described herein, including (but not limited to) the amino acid sequences set forth in anyone of SEQ ID NOs: 8-11. In one embodiment, the recombinant protein and/or the gamma subunit, as described herein is/are translated based on the DNA sequences provided herein. In one embodiment, the recombinant protein has an amino acid sequence that is at least 70%, 80%, 90%, 95%, or 97% identical to: (a) a recombinant protein translated from the DNA sequences provided herein or (b) anyone of SEQ ID NOs: 8-11.

In some embodiments, the protein of the invention comprises a tag. In some embodiments, the DNA encoding the proteins of the invention comprises sequence encoding the tag. In some embodiments, the tag is selected from an n-terminal tag, a c-terminal tag and an internal tag. A skilled artisan will appreciate that the tag should be positioned so as not to interfere with the function of the recombinant protein. Thus, the tag will not interfere with the redox activity or the DET activity. In some embodiments, the tag is a c-terminal tag. In some embodiments, the tag is a His tag. In some embodiments, the tag is a 6×His tag. In some embodiments, the His tag comprises or consists of the amino acid sequence IHIHHHHH. In some embodiments, the DNA encoding the His tag comprises the sequence CATCACCATCACCAT-CAC (SEQ ID NO: 24) (e.g., in addition to SEQ ID NO: 19-23). A skilled artisan will appreciate that any sequence which encodes the tag may be used. Protein tags are well known in the art and include, but are not limited to, HA tags, His tags, GFP tags, Myc tags, biotin tags, FLAG tags, streptavidin tags, and many, many others. Tagging may be useful for purification of the protein, and the tag may be cleaved before the enzyme is used. In some embodiment, the tag is small. In some embodiments, the tag is equal to or smaller than 40, 35, 30, 25, 20, 15, 10, 7, or 5 amino acids. Each possibility represents a separate embodiment of the invention. A smaller tag may be advantageous in that it is less likely to interfere with DET.

In some embodiments, the tag is connected to the recombinant protein by a linker. The linker may be a linker such as has been described hereinabove. In some embodiments, the linker comprises or consists of the sequence GSGSG. In some embodiments, the DNA sequence that encodes the linker comprises or consists of the sequence GGCAGTGGTTCCGGC (SEQ ID NO: 25) (e.g., in addition to SEQ ID NO: 19-23). A skilled artisan will appreciate that any sequence which encodes the linker may be used. In some embodiments, the linker is produced by the restriction site introduced into the DNA to produce the recombinant protein. Indeed, there may be a linker produced by restriction site insertion between any of the different parts of the recombinant protein.

General

As used herein the term "about" refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, and material arts.

As used herein, the term "treating" includes abrogating, substantially inhibiting, slowing or reversing the progression of a condition, of aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples which, together with the above descriptions, illustrate the invention in a non-limiting fashion.

Example 1

Plasmid Construction

Figure 6:
FIG. 6 is a map of expressed FGM. For the GDH, MCD sequence has been removed.

FAD-GDH γ subunit as well as its catalytic α subunit were cloned into pTrcHis6A2 vector between NcoI and HindIII restriction sites. The partial FAD-GDH gene was followed by a short flexible polypeptide linker (13 amino-acids long) and the MCR2 (minimal cytochrome domain—MCD) DNA sequence with 6×His tag at the sequence's C-terminal, as shown in FIG. 6 in a map of the new fusion protein. For the WT GDH the same construct was used, but without the MCD sequence. Full DNA construct:

```
                                        (SEQ ID NO: 26)
CCATGGCTCACAATGACAACACCCCGCACTCCCGCCGTACCGGCGATGCG

GCCGTGACCGGTATTACGCGTCGCCAGTGGCTGCAAGGCGCGCTGGCCCT

GACCGCAGCTGGCCTGACGGGTTCCCTGGCCCTGCGCGCACTGGCTGATG

ATCCGGGCACCGCACCGCTGGATACCTTTATGACGCTGAGCGAAGCTCTG

ACGGGCAAAAAAGGTCTGTCTCGTGTTCTGGGCCAGCGTTTTCTGCAAGC
```

-continued

```
GCTGCAAAAAGGTTCATTCAAAACCGCGGATTCGCTGCCGCAGCTGGCGG
GCGCCCTGGCAAGCGGTTCTCTGAACCCGGACCAAGAAGCTCTGGCGCTG
AAAATCCTGGAAGCATGGTATCTGGGCATTGTTGATAATGTGGTTATCAC
CTACGAAGAAGCCCTGATGTTTAGTGTCGTGTCCGACACGCTGGTCATTC
CGAGCTATTGCCCGAACAAACCGGGTTTCTGGGCCGAAAAACCGATCGAA
CGTCAGGCATAATGGCGGATACGGATACCCAGAAAGCGGACGTGGTCGTG
GTTGGATCCGGCGTGGCAGGCGCAATCGTGGCTCATCAACTGGCAATGGC
AGGTAAAAGCGTGATCCTGCTGGAAGCTGGTCCGCGTATGCCGCGTTGGG
AAATTGTTGAACGTTTCCGCAATCAAGTCGATAAAACCGACTTTATGGCA
CCGTATCCGAGCAGCGCATGGGCACCGCATCCGGAATATGGTCCGCCGAA
TGATTACCTGATCCTGAAAGGCGAACACAAATTTAACTCACAGTACATTC
GTGCAGTGGGCGGCACCACGTGGCATTGGGCAGCCTCGGCATGGCGCTTC
ATCCCGAACGATTTTAAAATGAAAACCGTGTATGGCGTTGGTCGTGACTG
GCCGATTCAGTACGATGACATCGAACATTATTACCAACGCGCGGAAGAAG
AACTGGGCGTGTGGGGTCCGGGCCCGGAAGAAGACCTGTATTCACCGCGT
AAAGAACCGTACCCGATGCCGCCGCTGCCGCTGAGTTTCAATGAACAAAC
CATTAAATCCGCTCTGAACGGCTATGATCCGAAATTTCACGTGGTTACGG
AACCGGTGGCCCGTAATTCGCGCCCGTACGACGGTCGCCCGACCTGCTGT
GGCAACAATAACTGCATGCCGATTTGTCCGATCGGTGCAATGTATAACGG
CATCGTCCATGTGGAAAAAGCTGAACAGGCAGGTGCTAAACTGATTGATA
GTGCGGTCGTGTACAAACTGGAAACGGGCCCGGACAAACGTATTACCGCA
GCTGTTTATAAAGATAAAACGGGTGCGGACCATCGCGTCGAAGGCAAATA
CTTCGTGATTGCGGCCAATGGTATCGAAACCCCGAAAATTCTGCTGATGA
GCGCGAACCGTGATTTTCCGAATGGTGTGGCCAACAGTTCCGATATGGTT
GGCCGCAATCTGATGGACCATCCGGGCACCGGCGTGAGCTTTTATGCAAA
CGAAAAACTGTGGCCGGGTCGTGGTCCGCAGGAAATGACCTCTCTGATCG
GTTTCCGTGATGGCCCGTTTCGCGCGAATGAAGCAGCGAAGAAAATTCAT
CTGTCAAATATGTCGCGTATCAACCAGGAAACCCAAAAAATCTTTAAAGG
CGGTAAACTGATGAAACCGGAAGAACTGGATGCGCAGATCCGTGACCGCA
GTGCCCGCTTTGTTCAATTCGATTGCTTTCACGAAATCCTGCCGCAGCCG
GAAAATCGTATTGTCCCGTCCAAAACCGCAACGGACGCAGTGGGTATTCC
GCGTCCGGAAATTACGTATGCGATCGATGACTACGTCAAACGTGGCGCAG
TGCATACGCGCGAAGTTTATGCTACCGCGGCCAAAGTGCTGGGCGGCACC
GAAGTGGTCTTCAACGATGAATTTGCGCCGAATAACCACATCACCGGTGC
CACGATTATGGGCGCGGATGCCCGTGACTCAGTGGTTGATAAAGACTGTC
GCGCCTTCGATCATCCGAACCTGTTTATTAGCAGCAGCAGCACCATGCCG
ACGGTTGGCACCGTTAACGTCACCCTGACGATTGCAGCTCTGGCACTGCG
TATGTCTGATACGCTGAAAAAAGAAGTCGAATTCGGTTCTGGTTATGGCT
CTGGTCCGCCGGGTCCGATTCGTGCAGGTGCTACCATGCCGCATCGTGAT
CGTGGTCCGTGCGGTGCATGTCACGCTATTATCCAGGGCAGTGGTTCCGG
CCATCACCATCACCATCACTAAAAGCTT.
```

The first 6 nucleotides and the last 6 nucleotides are NcoI and HindIII' restriction sites. The Gamma subunit is expressed as a separate protein encoded from nucleotide 3 to nucleotide 512 of the DNA molecule described herein. The Alpha subunit is from nucleotide 512 to nucleotide 2128. The flexible linker is from nucleotide 2129 to nucleotide 2167. The carboxy terminal MCD linker is from nucleotide 2168 to nucleotide 2238. 6 times His-Tag from nucleotide 2239 to nucleotide 2269.

Enzyme Expression and Purification

The complete pTrcHis6A2-FAD-GDH-MCD plasmid was transformed into E-coli BL21 cells for the expression of the fusion protein (FAD-GDH-MCD). Bacteria were cultured in an auto-induction medium (Formedium™, Hunstanton, England) with 0.5% glycerol (Bio-Lab ltd., Jerusalem, Israel) and 10 µg/mL carbenicillin (Apollo, Manchester, England) and grown in 37° C., with shaking at 250 rpm, for 6 hours after which cells were transferred to 27° C. for 18 additional hours.

The cells were then centrifuged at 6000 rpm for 10 minutes, the pallet was resuspended using 20 mL 50 mM Tris-base buffer (TB, Fisher scientific, Geel, Belgium) pH=7.0, centrifuged, weighted, and resuspended using lysis buffer (300 mM KCl, 50 mM $KH_2PO_4$, 10 mM imidazole pH=7.0) in a 1:3 (weight:buffer volume) ratio. Protease inhibitors, lysozyme and supernuclease were added to the suspension in 1:500, 1:400, and 1:5000 ratios, respectively. The cells were lysed using sonication needle followed by 15 minutes of 50° C. incubation and centrifugation (11,500 rpm for 25 minutes). The supernatant was filtered using 0.22 µm filter.

The fusion enzyme was purified using IMAC purification system (Bio-Rad, Profinia, Hercules, CA, USA) according to manufacturer instructions.

FAD-GDH Activity Assay

To assess FGM's D-glucose oxidation activity, glucose oxidation was measured in the presence of 0.6 mM 2,6-Dichloroindophenol (DCIP, Sigma-Aldrich, Rehovot, Israel), 0.6 mM phenazine methyl sulfate (PMS, Tokyo chemical industry, Tokyo, Japan), different concentrations of D-glucose and 0.2 mM FGM, all dissolved in 50 mM TB pH=7.0. Assay was performed in 37° C. using a 96-well plate reader (BioTek instruments, Winoosky, VT, USA) with shaking between measurements, monitoring the decrease in the DCIP absorbance $\lambda=610$ nm every 15 seconds over 25 min of activity.

Heme Activity Measurements

To verify the attachment of a porphyrin to the MCD domain, heme activity was measured using 1 mM dimethoxybenzidine (DMB, Alfa Aesar, Heysham, England), 1 mM hydrogen peroxide (Sigma-Aldrich, Rehovot, Israel), and 0.2 mM of the enzyme. Measurements were performed at 37° C. using a 96-wells plate reader, monitoring the increase in DMB absorbance $\lambda=455$ nm every 15 seconds over 30 min of activity.

Peroxidase Activity Interference Measurements

To verify that FGM does not transfer electrons to oxygen, producing hydrogen peroxide, that interferes with the FAD-GDH activity assay, peroxidase activity test was performed in the absence of hydrogen peroxide. 0.17 mM DMB and 172 mM glucose were mixed with 8 μL of 0.1 mg/mL Horseradish peroxidase (HRP, Sigma-Aldrich, Rehovot, Israel) to generate a reaction mix. 8 μL of concentrated FGM or glucose oxidase (GOx) were added to the reaction mix right before measurement. Measurements were performed at 37° C. using a plate reader, monitoring the increase in DMB absorbance λ=500 nm every 15 seconds over 25 min of activity (FIG. 3C).

Electrode Preparation

Glassy carbon electrodes (GCE, 3 mm in diameter; ALS, Tokyo, Japan) were polished using 0.05 μm alumina slurry on polishing pad for two minutes, then transferred to a 20 mL glass with 10 mL double-distilled water (DDW) and sonicated for five minutes in a sonication bath. The electrodes were then dried under nitrogen gas. 10 μL of enzyme solution in wanted concentrations was dropped on the electrode surface. The electrodes were incubated in 4° C. overnight to generate an enzyme film on the GCE. Electrode's surfaces were then covered with 12-14 kDa dialysis membrane (Membrane Filtration Products, Seguin, TX, USA) and tightened using an O-ring rubber to prevent diffusion of the enzyme to the solution.

Electrochemical Measurements

Figure 7A:
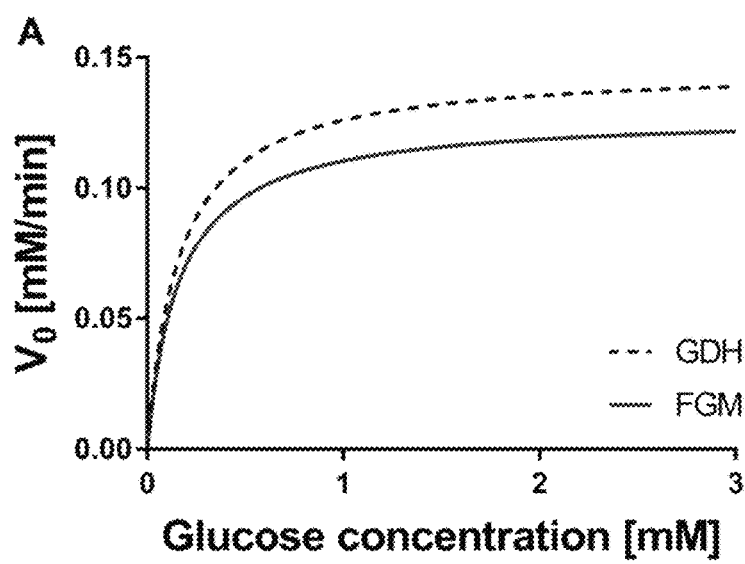
FIGS. 7A-7C are graphs showing: Michaelis-Menten (FIG. 7A) and Lineweaver-Burk (FIG. 7B) plots of biochemical FAD-GDH activity for both, FGM and GDH. Linear trend line equations were calculated to be y=1.2x+6.7 for GDH and y=1.2x+7.7 for FGM and chronoamperometric measurements of glucose catalytic oxidation by FGM and GDH at an applied potential of 0.0 mV (FIG. 7C)
Figure 7B:
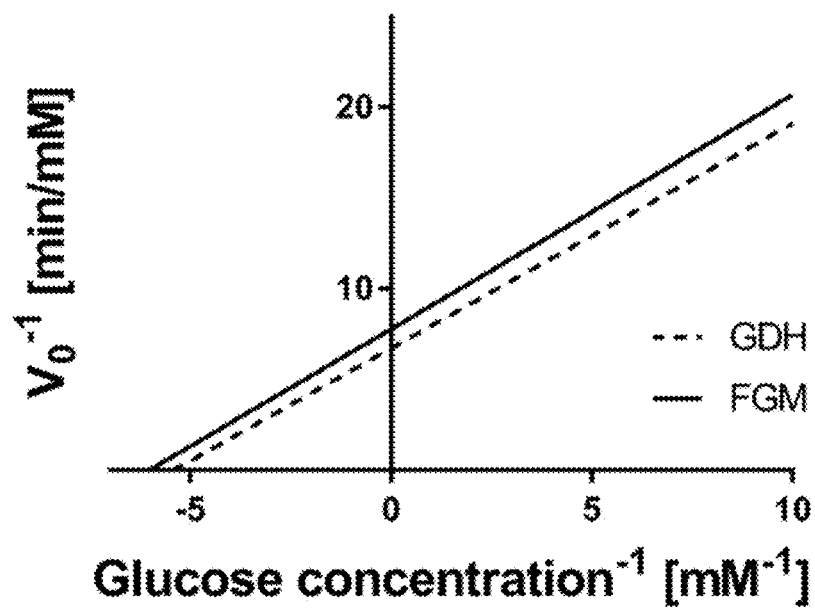
Figure 7C:
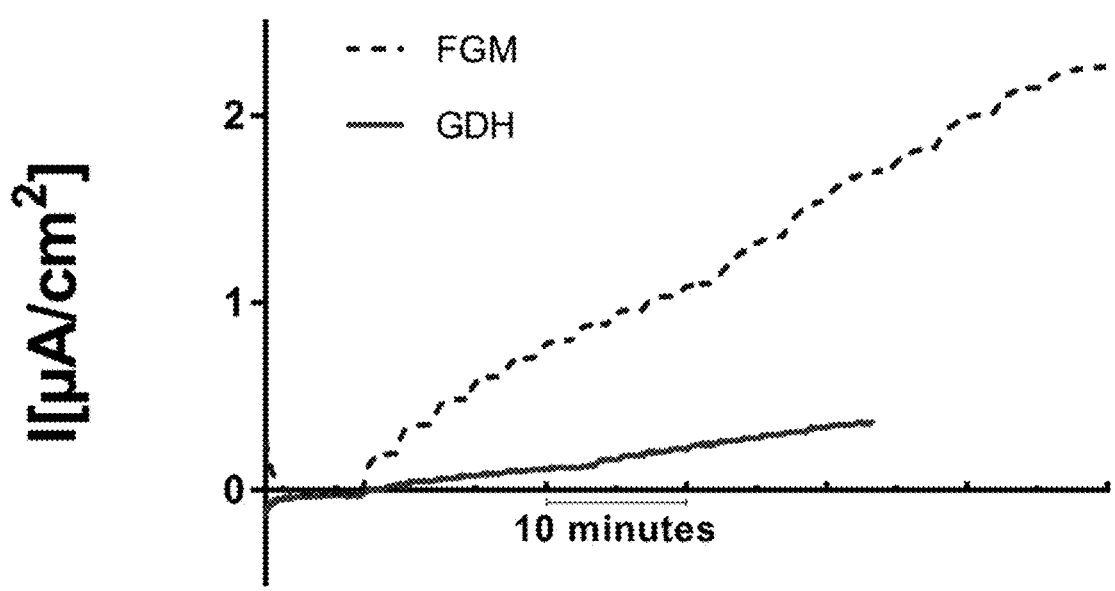

Cyclic voltammetric measurements were performed using a PalmSense2 potentiostat (Palm Instruments, Houten, The Netherlands) using a standard three electrodes system with 0.9 mm graphite rod as an auxiliary electrode, 3M KCl saturated Ag/AgCl reference electrode (ALS, Tokyo, Japan) and GCE as the working electrode in 0.15M phosphate-citrate buffer pH=5.0. Chronoamperometric measurements (FIG. 7) were performed under the same conditions with the application of 0 mV vs. Ag/AgCl with the addition of varying concentrations of glucose or potential interfering molecules. Square wave voltammetry (SWV) measurements were performed under the same conditions.

FGM Selectivity Test

Figure 8A:
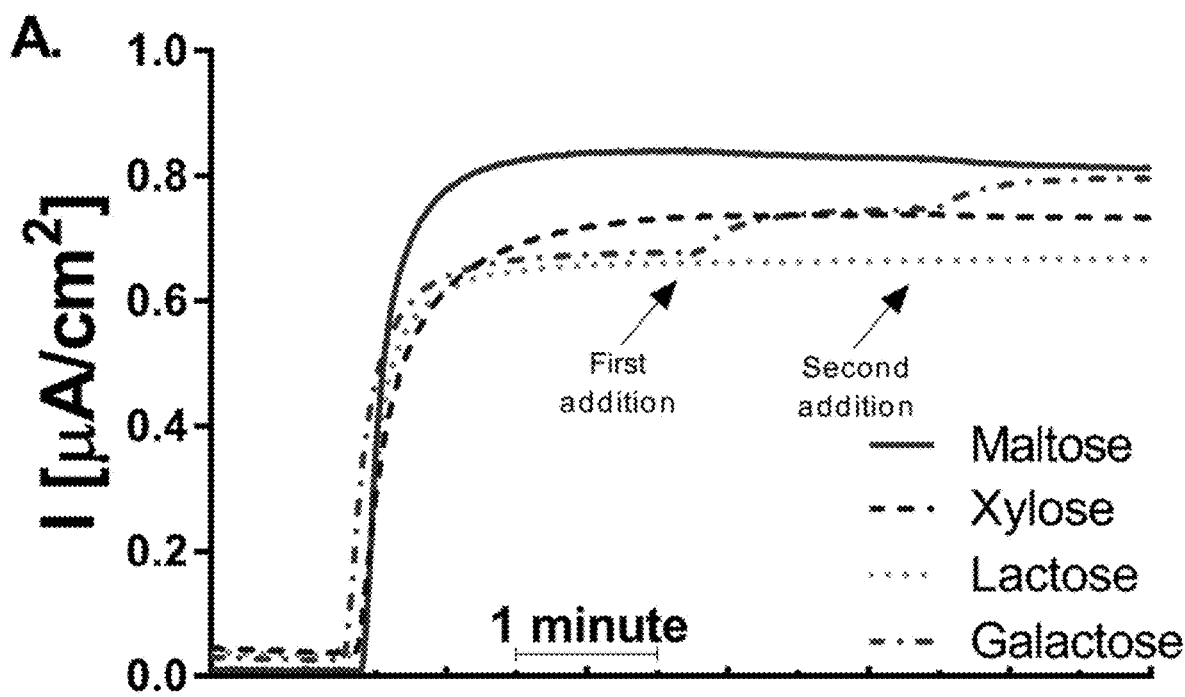
FIGS. 8A-8C are graphs showing GCE/FGM selectivity test that was performed by adding 3.6 mM glucose followed by two sequential additions of sugars in their relevant physiological concentration—1.67 and 3.3 mM galactose (-•-), 0.3 and 0.6 mM lactose (•••), 2.9 and 5.8 mM maltose (red -) and 1.67 and 3.3 mM xylose (- - -) (FIG. 8A); other molecules interference was tested by adding 3.6 mM glucose followed by two additions of 0.17 mM ascorbic acid and 0.2 mM acetaminophen at an applied potential of 0.0 mV (FIG. 8B); and 300 mV vs. Ag/AgC (FIG. 8C)
Figure 8B:
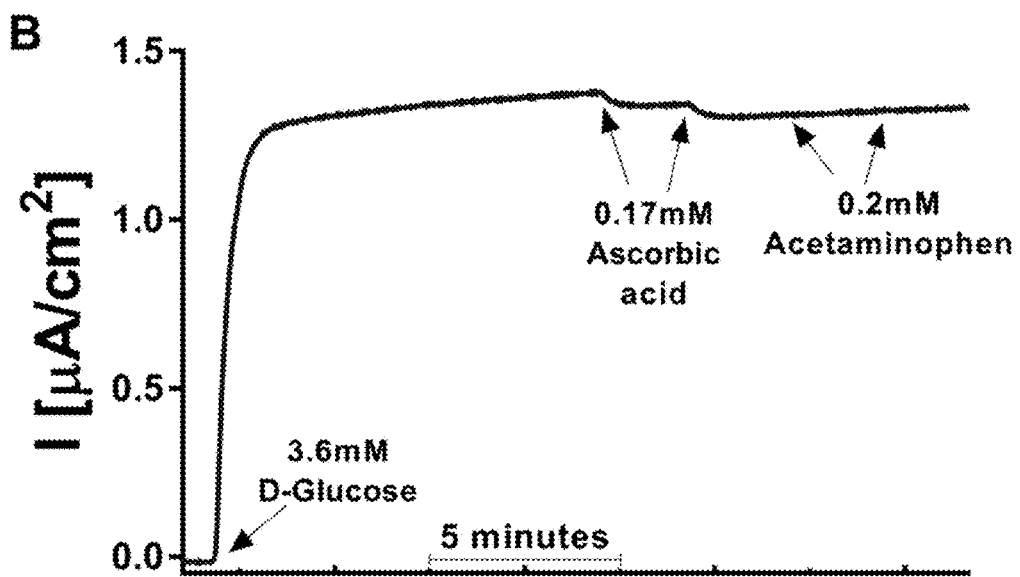
Figure 8C:
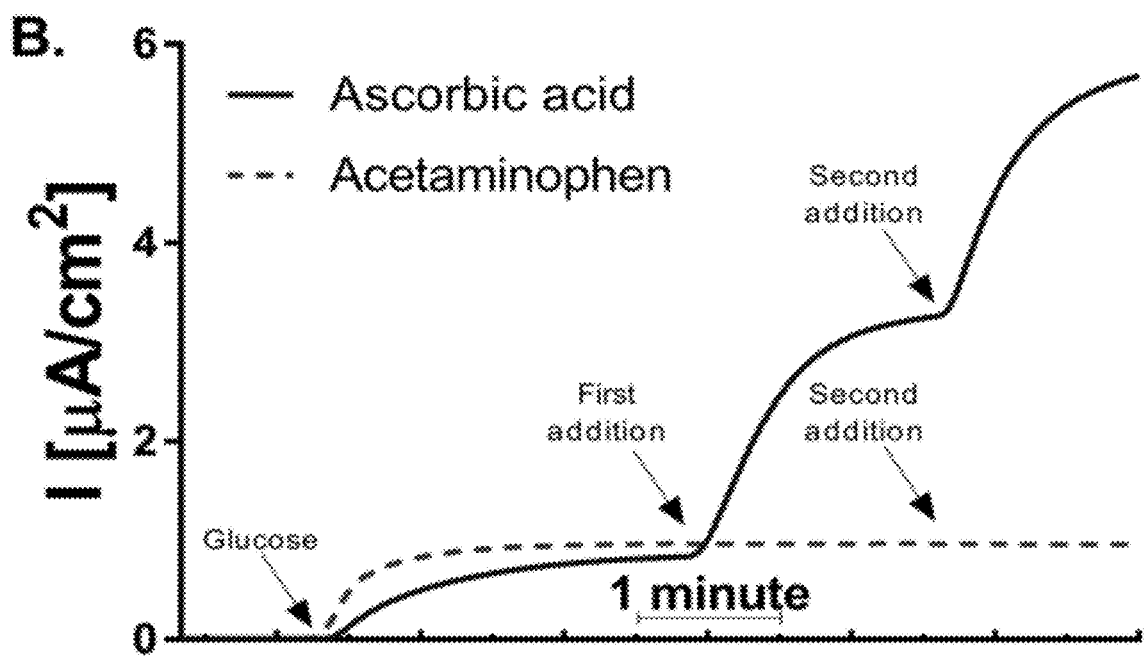

The interference of different sugars and molecules on glucose biosensing by GCE/FGM was measured using chronoamperometry (see selectivity FIGS. 8A-C). Measurements were performed in 0.15M phosphate-citrate buffer pH=5.0 with the application of 0 mV vs. Ag/AgCl reference electrode. FGM selectivity was tested by adding 3.6 mM of glucose followed by two sequential additions of one of the different sugars or molecules in their relevant physiological concentrations. The sugars used for this test were D-galactose, lactose, D-maltose and D-xylose and the molecules were ascorbic acid and acetaminophen (all from Sigma-Aldrich, Rehovot, Israel). Selectivity test have revealed a small interference caused by galactose while other sugars did not interfere with the measurement. This result indicates high selectivity towards glucose and low/no reaction with other sugars that can be found in human blood samples, which is very important for biosensing accuracy. GCE\FGM showed low sensitivity to ascorbic acid and no sensitivity to acetaminophen.

The Biocatalytic Recombinant Protein

Figure 1:
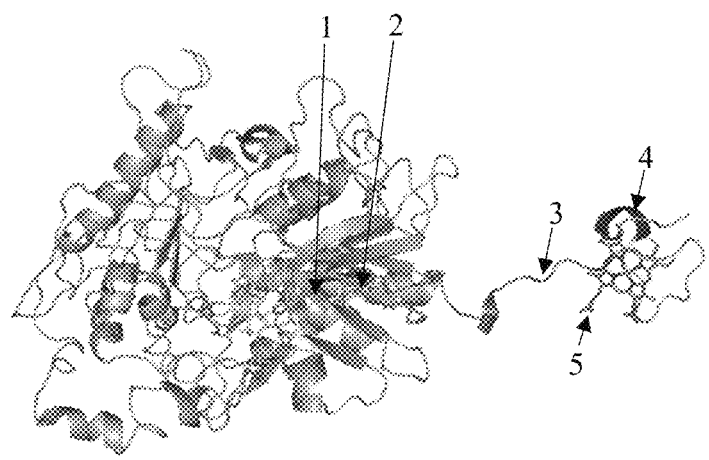
FIG. 1 is a 3D model of Flavin-adenine dinucleotide dependent glucose dehydrogenase FAD-GDH-MCD (FGM) based on the structure of GDH, predicted by homology to formate oxidase using Swiss-model (3q9t) and on the structure of MCD from MamP crystal structure (4jj0). FAD-GDH from *Burkholderia cepacia* is presented with its FAD binding motif (orange, "1") and the FAD co-factor MCD model (light orange, "2") and the linker (grey, "3") were cut from mamP known 3D structure and include the Heme binding motif (red, "4") and heme molecule (pink, "5"). Heme and FAD molecules were attached to the protein model manually using PyMOL.

In the present study, a fusion enzyme was designed in a combination of a biocatalytic function from a redox enzyme domain that was fused to a natural minimal ET domain via a short polypeptide linker as shown in FIG. 1. As the catalytic domain, the a subunit of an FAD-GDH from *Burkholderia cepacia* was used. As a minimal ET unit, the c-type cytochrome domain MCR-2 from a MamP protein which originates from a magnetotactic bacteria magnetoovoid bacterium MO-127 was chosen. MamP is part of the magnetosome, a unique organelle that is found in magnetotactic bacteria that allows magneto taxis to occur in these bacteria. MCR-2 is one of the shortest natural c-type cytochromes known today (23 amino-acids long), thus can be used to achieve DET.

In order for FAD-GDH-MCD (FGM) fused enzyme to mature properly in the host cell, FAD-GDH α subunit should correctly fold. The Enzyme's γ subunit aids in the maturation of the a subunit and locates it in the periplasm. Within the bacterial periplasmatic environment, the maturation of c-type cytochromes (heme binding cytochromes) occurs with the help of a specific gene cluster called ccmA-H29. In that manner, the holo-enzyme is being transferred to the periplasm and there the MCD's maturation process occurs.

Figure 2A:
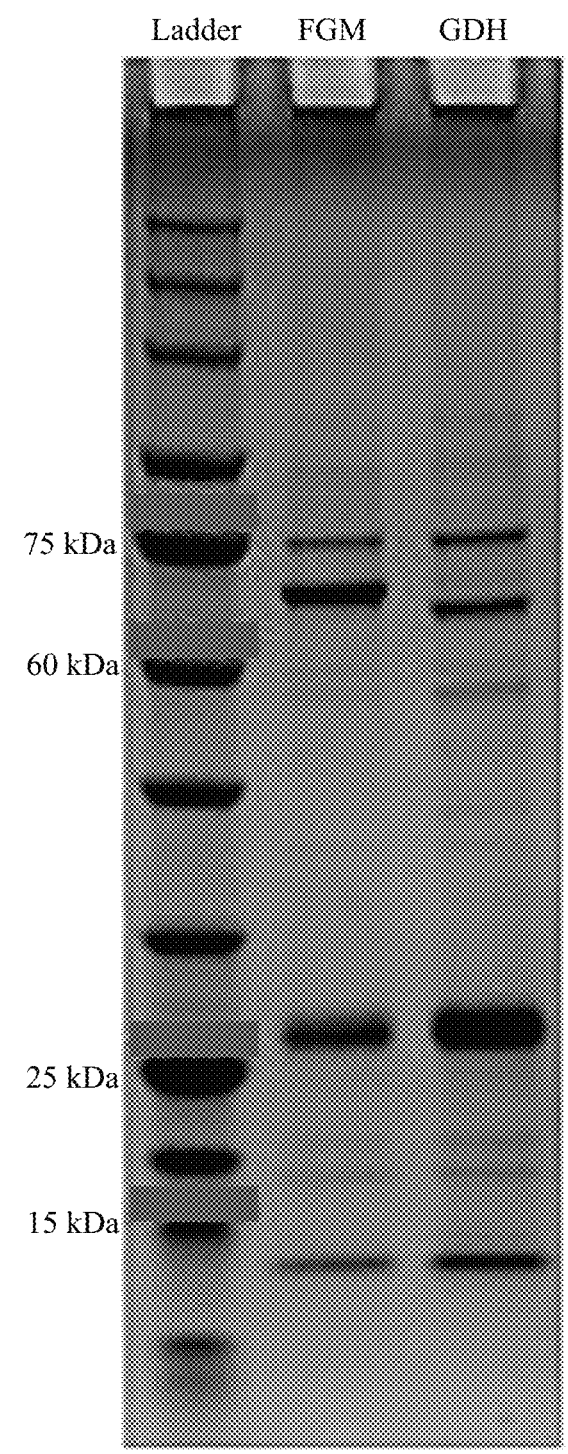
FIGS. 2A-2B present gel micrographs: Coomassie stained sodium dodecyl sulfate-polyacrylamide gel electrophoresis (SDS-PAGE) analysis of FGM and GDH elution fractions resulting from IMAC purification. FGM and GDH catalytic sub-units are shown between 60 to 75 kDa. Band at ca. 13 kDa in both lanes correlates to FAD-GDH γ subunit (FIG. 2A); and in-gel heme staining showing the presence of a heme molecule in FGM compared to its absence in GDH (FIG. 2B, left panel) and Anti 6×his-tag Western blot verifying the full-length protein expression.
Figure 2B:
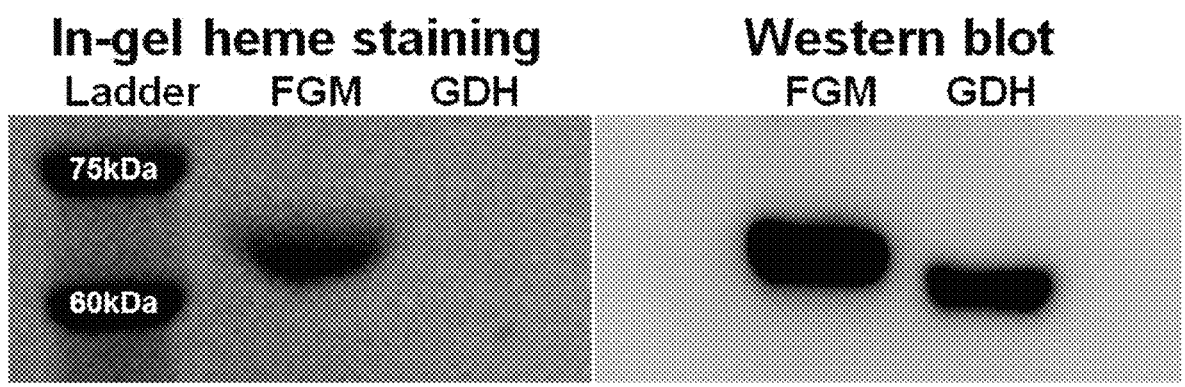

Fusion enzyme's engineered DNA sequence was cloned into pTrcHis6A2 expression vector and was transformed into *E-coli* BL21. FGM was overexpressed in the bacterial expression system and then purified by utilizing immobilized metal affinity chromatography (IMAC) purification system (FIG. 2A). In-gel heme staining was performed to verify the presence of the heme compared to GDH and Anti his-tag Western blot analysis was performed in order to verify the full-length enzyme's expression (FIG. 2B, right panel). As shown in FIG. 2B, both FGM and GDH enzymes were expressed and their respective bands appeared in the expected size—ca. 64 kDa and 62 kDa for FGM and GDH, respectively. In-gel heme staining revealed a band for FGM only, indicating the presence of a porphyrin containing iron bound to FGM.

Figure 3A:
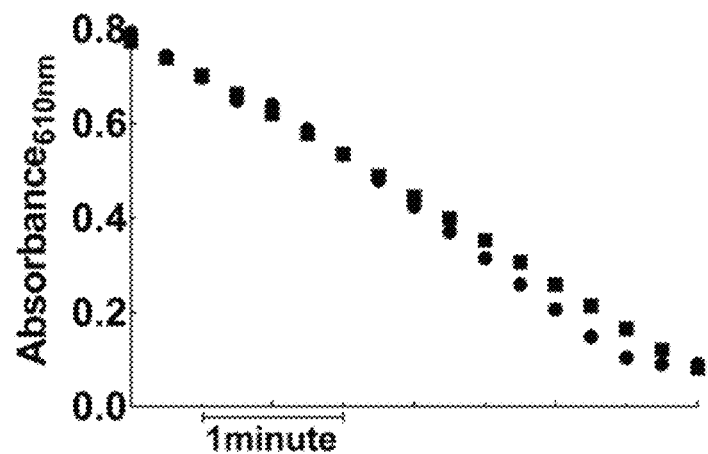
FIGS. 3A-3D are graphs showing: 2,6-dichloroindophenol (DCIP) reduction assay comparing the oxidation of D-glucose by both FGM (■) and GDH (•) (FIG. 3A) and Heme activity measurements verifying the presence of a porphyrin in FGM compared to GDH. Measurements were performed in 37° C., 50 mM Tris buffer, pH=7.0 (FIG. 3B); Peroxidase activity interference test; FGM was compared to Glucose oxidase (GOx) which is oxygen sensitive; No hydrogen peroxide was detected upon glucose oxidation by FGM while GOx, as a positive control, showed hydrogen peroxide production and its subsequent reduction by HRP is visible (FIG. 3C); and absorbance spectrum of FGM and GDH showing peak in absorbance at 408 nm for FGM and no peak for GDH (FIG. 3D)

FGM catalytic redox activity and heme peroxidase activity were measured biochemically and compared to GDH as shown in FIG. 3A. FGM has oxidized D-glucose as was measured by FAD-GDH activity assay in 50 mM Tris-base (pH 7.0), 0.6 mM 2,6-Dichloroindophenol (DCIP) and 0.6 mM phenazine methyl sulfate (PMS) in 37° C. Absorbance (lambda=610 nm) was monitored using a plate reader while the oxidized DCIP (blue color) was being reduced by FGM to its reduced form (colorless). FGM has also shown peroxidase activity, measured by heme activity assay in 1 mM 3,3'-Dimethoxybenzidine (DMB) and 1 mM of hydrogen peroxide. Absorbance in 455 nm was monitored while the DMB oxidation occurs by the MCD, resulted in an oxidized DMB (red color). Heme activity assay results indicate that FGM indeed binds a heme group while no heme molecules are bound by GDH.

Figure 3B:
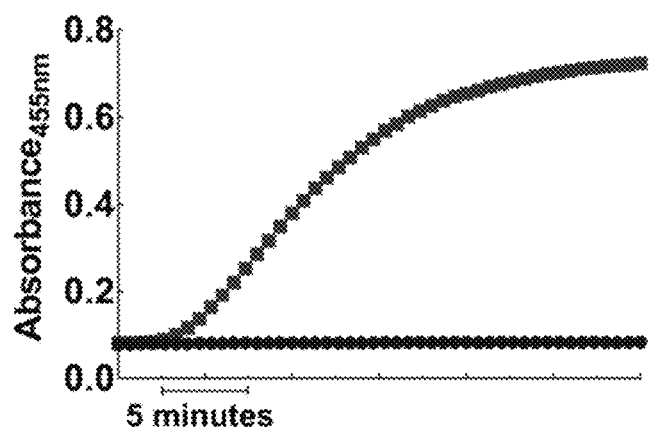
Figure 3C:
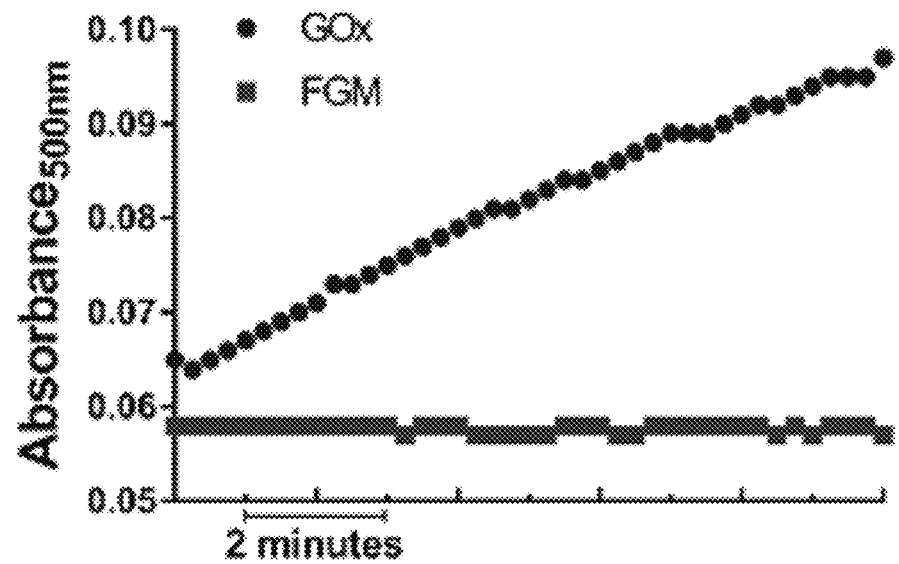
Figure 3D:
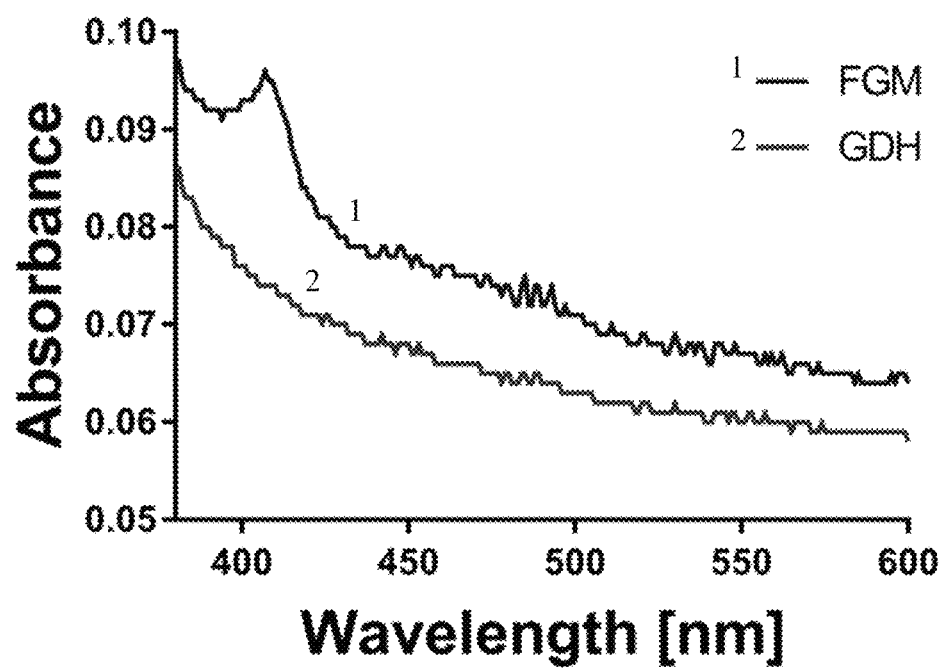

Absorbance measurements of protein sample spectrum revealed a peak in absorbance at 408 nm for FGM and no peak for GDH, indicating presence of heme c in FGM (FIG. 3B). 408 nm/A280 nm ratio was calculated to be 0.4 for FGM expressed in the presence of pEC86 plasmid, compared to 0.2 for FGM expressed in the absence of this plasmid, indicating more efficient heme maturation in the presence of the helper plasmid.

The apparent kinetic and thermodynamic parameters of FGM were calculated using FAD-GDH biochemical activity assay in 37° C. (Table 1). FGM and GDH concentrations were first determined spectrophotometrically using a standard Bradford assay. Michaelis-Menten curves were transformed to Lineweaver-Burk curves in order to determine the kinetic and thermodynamic parameters of the enzyme. One enzyme activity unit was defined as amount of enzyme oxidizing 1 μM of substrate per minute. The molar absorption coefficient of DCIP was calculated to be 4.7 cm$^{-1}$mM$^{-1}$. By using the biochemical activity assay and DCIP molar absorption coefficient, FGM and GDH specific activity were calculated to be 16 mU.

Lineweaver-Burk plots (FIGS. 7A-B) were used to calculate kinetic and thermodynamic parameters of the enzyme. $K_M^{app}$ values were 157±5 μM and 174+9 μM for FGM and GDH, respectively, showing different affinity of the enzymes toward the substrate. GDH's $K_M^{app}$ value is lower than reported values but yet in the same order of magnitude of some. $K_M^{app}$ value was ca. 3 times higher for FGM compared to GDH, indicating faster oxidation of D-glucose by FGM. FGM also showed more than 3 times higher catalytic efficiency (k) compared to GDH (Table 1). Next, the electrochemical activity of the enzymes was measured to determine whether the addition of the minimal cytochrome domain improves enzyme-electrode ET.

Figure 5A:
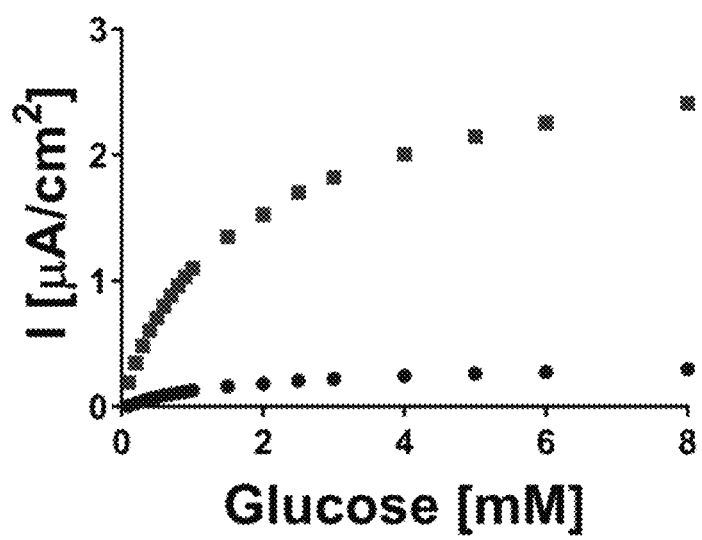
FIGS. 5A-5B present graphs showing steady state currents from chronoamperometry measurements of GCE/GDH (•) and GCE/FGM (■) using different glucose concentrations (FIG. 5A); and Lineweaver-Burk plots of electrochemical activity for both, FGM and GDH. Linear trend line equations were calculated to be y=123x+42.3 for GDH and y=10.1x+7.1 for FGM (FIG. 5B)
Figure 5B:
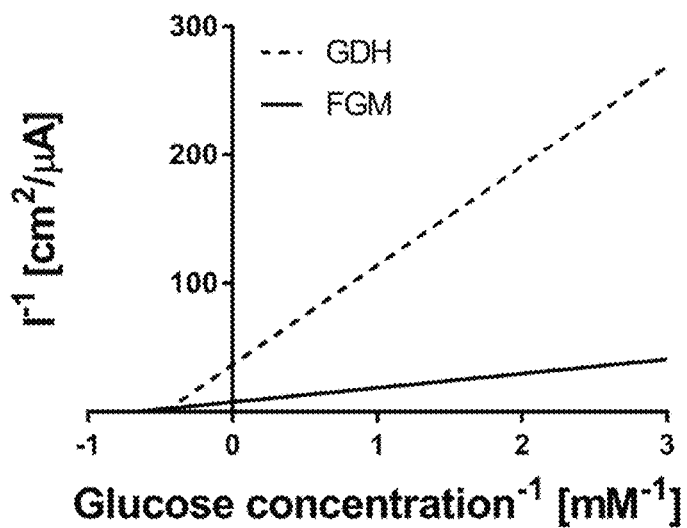

Chronoamperometric measurements (FIG. 7C) were performed to determine the apparent kinetic parameters of FGM compared to GDH. Using a standard 3 electrode electrochemical cell, the current was measured vs. successive glucose additions. A potential of 0V was applied during the measurements. The current for each glucose concentration was determined and is presented in FIG. 5A. As described above, using the linear part of the transient curves and Linewaver-Burk transformation—the electrochemical kinetic constants were calculated (FIG. 5B).

TABLE 1

Apparent biochemical kinetic parameters of FGM and GDH

|  | $k_{cat}^{app}$ (s$^{-1}$) | $K_M^{app}$ (µM) | $K_{cat}^{app}/K_M^{app}$ (s$^{-1}$ · mM$^{-1}$) |
|---|---|---|---|
| GDH | 1.7 ± 0.1 | 174 ± 9 | 9.6 ± 0 |
| FGM | 5.2 ± 0.1 | 157 ± 5 | 33 ± 0 |

For the electrochemical measurements, a standard 3 electrode electrochemical cell with 0.9 mm graphite rod as the auxiliary electrode were used, 3M KCl saturated Ag/AgCl reference electrode and 3 mm diameter glassy carbon electrode (GCE) as the working electrode. 10 µL of ca. 30 µg/mL FGM or GDH enzyme solution were dropped on the GCE surface and dried in 4° C. overnight. The electrodes surface was then covered with 12-14 kDa dialysis membrane tightened to the surface with an O-ring to keep the enzyme close to the electrode surface during measurements and to avoid enzyme diffusion to the surrounding buffer. Cyclic voltammetry (CV) measurements were performed to compare the enzyme-electrode communication of FGM to that of GDH.

Optimal pH value for electrochemical measurements was tested by measuring the catalytic current in pH values of 3.6-7.0 and found to be 5.0.

Figure 4A:
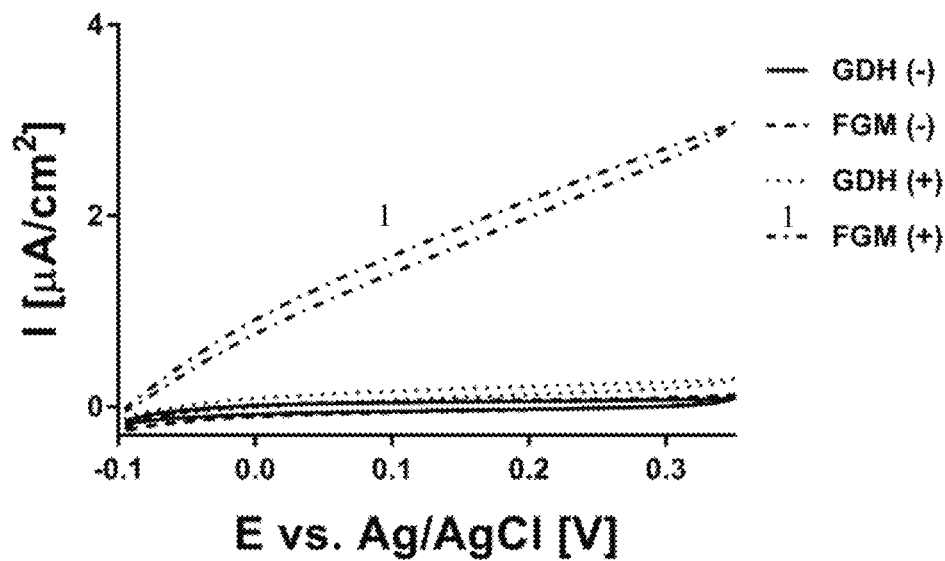
FIGS. 4A-4C present graphs showing cyclic voltammograms of GCE/GDH and GCE/FGM with (+) and without (−) 5 mM glucose. The measurements were performed in 150 mM phosphate-citrate buffer, pH=5.0 at room temperature vs Ag/AgCl as a reference electrode at a scan rate of 5 mV s$^{-1}$ (FIG. 4A) and 100 mV s$^{-1}$ (FIG. 4B), and square-wave voltammetry (SWV)s of GCE/GDH and GCE/FGM. Measurements performed in 150 mM phosphate-citrate buffer, pH=5.0 vs Ag/AgCl reference electrode with 5 mV steps, amplitude 10 mV and a frequency 5 Hz (FIG. 4C). Background GCE current subtracted from the signal (GCE: glassy carbon electrode)
Figure 4B:
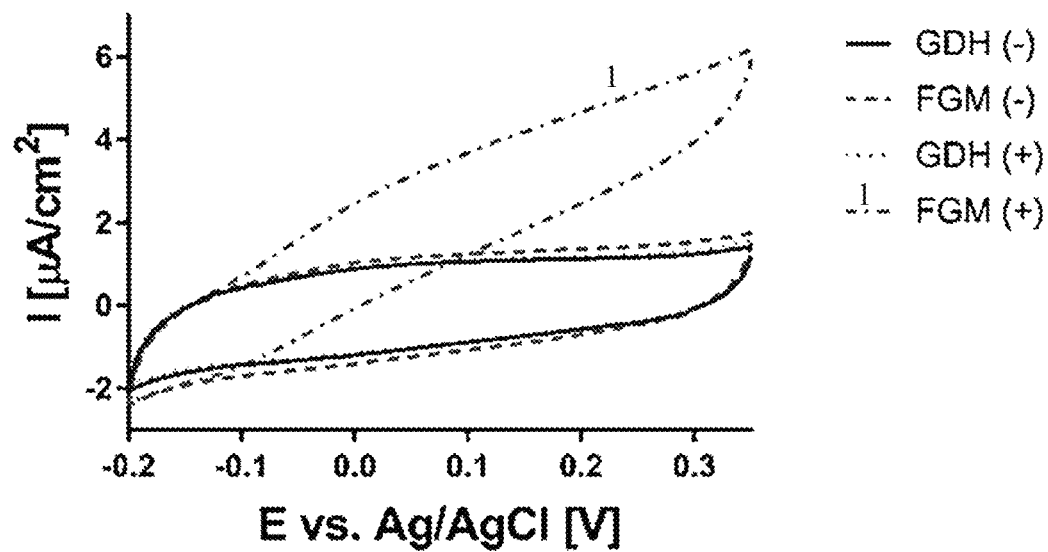

Measurements were performed in phosphate-citrate buffer pH=5.0 at room temperature and a scan rate of 5 mV/sec for both enzymes with and without the addition of 5 mM glucose. It can be seen in FIGS. 4A-B that the CVs of both enzymes before the addition of glucose are almost identical. No clear anodic or cathodic peaks were identified for both enzymes. After the addition of glucose to a final concentration of 5 mM, FGM has demonstrated 10 times higher electrocatalytic current compared to that of GDH with an onset potential of ca. −100 mV for both enzymes (indicating no apparent shift in potentials due to the fusion of MCD). That difference in the ET efficiency is probably due to the addition of the minimal cytochrome domain that mediates the ET from the buried FAD co-factor to GCE.

Figure 4C:
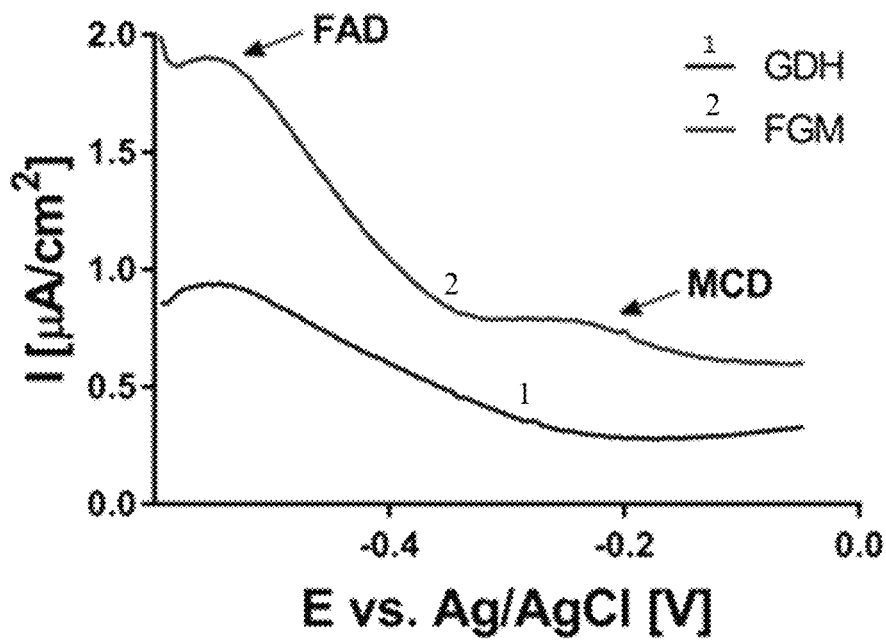

After the addition of glucose to a final concentration of 5 mM, FGM demonstrated a higher electrocatalytic current compared to that of GDH with an onset potential of ca. (−) 150 mV. The fact that no catalytic current was observed at this high scan rate using GDH, but a significant catalytic current evolved using FGM, is an indication of fast ET rates of FGM. That observed ET efficiency is probably due to addition of the minimal cytochrome domain that mediates ET from the buried FAD cofactor to GCE. To identify a peak originating from the MCD domain, square-wave voltammetry (SWV) was performed. As shown in FIGS. 4C, the voltammogram of an electrode with FGM revealed a peak around (−) 230 mV, whereas GDH had no observable peak at this potential.

As shown in Table 2, the electrochemical $K_M^{app}$ is 2.84±0.57 mM for GDH and 1.40±0.27 mM for FGM, indicating no significant difference in the affinity towards glucose. The $i_{max}$ value is one order of magnitude higher for FGM compared to GDH—2.04±0.45 µA·cm$^{-2}$ and 0.4±0.17 µA·cm$^{-2}$, respectively. The difference in the $i_{max}$ value is indicative that the DET efficiency is different between the two enzymes where FGM shows five to seven times higher current then GDH for the same glucose concentrations.

TABLE 2

Apparent electrochemical kinetic and thermodynamic parameters of FGM and GDH

|  | $K_M^{app}$ (mM) | $i_{max}$ (µA · cm$^{-2}$) |
|---|---|---|
| GDH | 2.8 ± 0.6 | 0.4 ± 0.2 |
| FGM | 1.4 ± 0.3 | 2.0 ± 0.5 |

Figure 9:
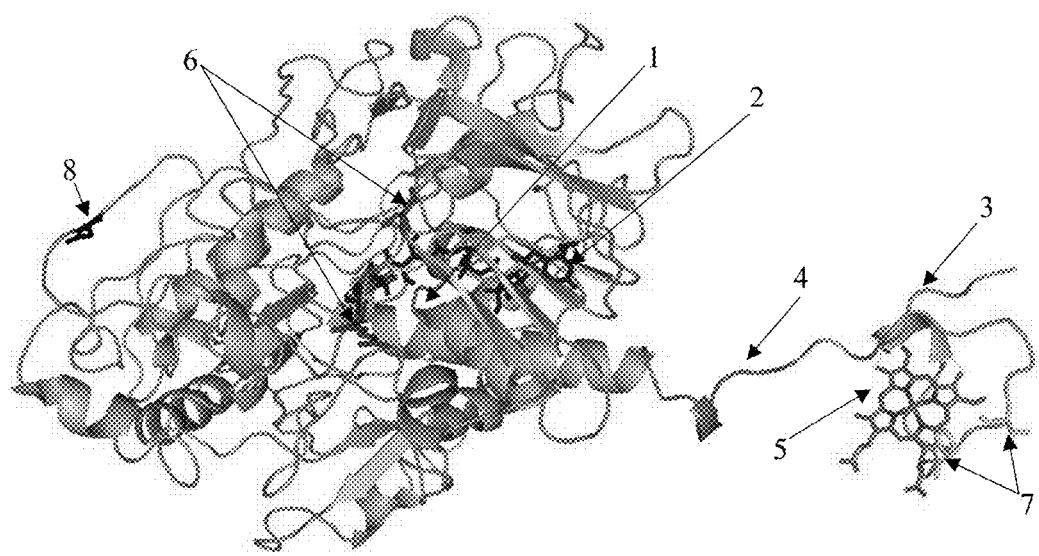
FIG. 9 presents 3D model of FAD-GDH from *B. cepacia* (green) is presented with its FAD binding motif (orange, "1") and the FAD co-factor (blue, "2"). MCD model (cyan, "3") and the linker (grey, "4") were cut from MamP known 3D structure and include the heme molecule (pink, "5"). The fusion shown in this figure was manually generated using PyMOL software. ncAA possible incorporation sites were colored—proximity to FAD (red, "6"), to MCD (yellow, "7"), distant from both FAD and MCD (black, "8")

*Burkholderia cepacia* is considered a good candidate for biosensing applications because of its stability in high temperatures and insensitivity to oxygen. By adding a minimal cytochrome domain to FAD-GDH c-terminus an improved DET was provided, showing higher catalytic currents compered to GDH with almost the same affinity to the substrate. When tested electrochemically with 0V induced potential vs Ag/AgCl, FGM showed much higher currents for the same substrate concentrations compared to GDH, which makes it more accurate for glucose biosensing with improved sensitivity than previously reported for GDH.
Non-Canonical Amino Acids (ncAAs) Incorporation into FGM for Site-Specific Wiring to an Electrode:
FGM Electron Transfer Machineries Investigation To incorporate non-canonical amino acids (ncAAs) into FGM, a few constructs containing the amber (TAG) mutation on pTrcHis6A2-FGM plasmid were prepared using standard site-directed mutagenesis PCR protocol. The mutations were chosen with a proximity to the protein different domains—FAD binding domain, MCD and one site that is distant from either FAD domain or MCD. For proximity to FAD binding domain, two sites were found to be possible for ncAA incorporation—R42X and S247X (FIG. 9—red), both ca. 11 Å from FAD binding domain. For proximity to MCD, T558X and P560X (yellow) are possible sites for incorporation, with 10 and 7 Å from MCD, respectively. D395X (black) was found to be far from both FAD and MCD as it is about 37 Å from FAD and 83 Å from MCD.

Mutated plasmids were transformed into super competent *E. coli* DH5α cells and were plated on selective LB-agar plates. Bacterial colonies were isolated and plasmids were purified using miniprep kit followed by sequencing.
Non-Canonical Amino Acids (ncAA) Incorporation into FGM Plasmids, with amber codon-containing FGM mutants sequences were co-transformed to *E. coli* BL21 strain containing the pEVOL plasmid expressing Pyrrolysyl orthogonal translation system to incorporate Propargyl-lysine (PrK) into the protein sequence. PrK containing protein was expressed in 20 mL auto-induction medium (AIM) in the presence of 1 mM PrK, lysed using Bugbuster lysis solution and was isolated utilizing IMAC purification method. PrK is an example to a clickable nCAA, all clickable biorthogonal chemical handles can be considered for the site-specific wiring of this enzyme.

Pyrene-Azide Linkers for Enzyme Wiring to Electrode

Figure 10A:
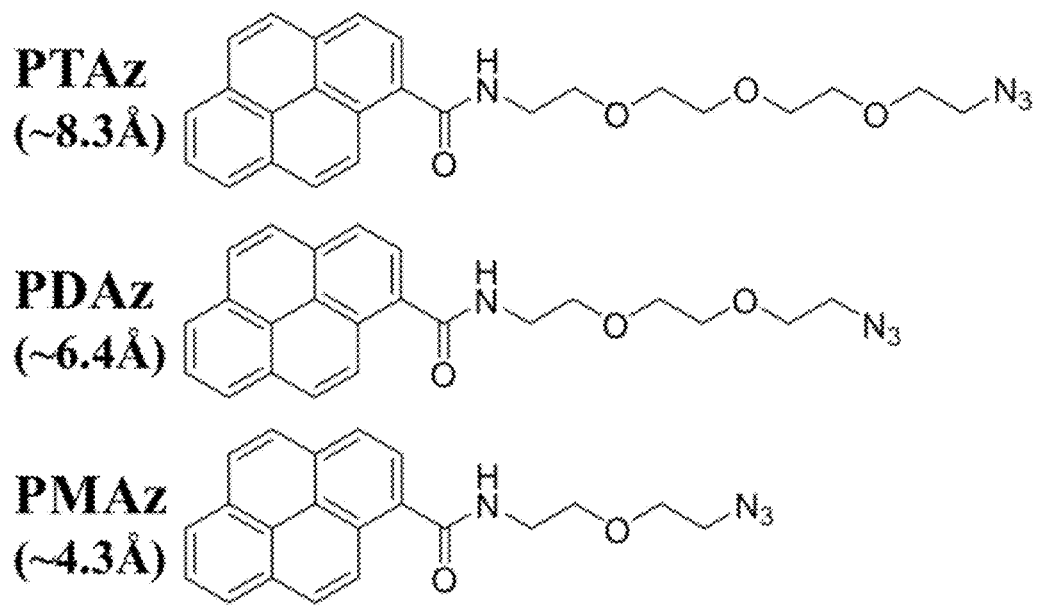
FIGS. 10A-10B present non-limiting pyrene-azide linker structures with different lengths (FIG. 10A) and 5-etramethylrhodamine (TAMRA)-azide chemical structure (FIG. 10B)
Figure 10B:
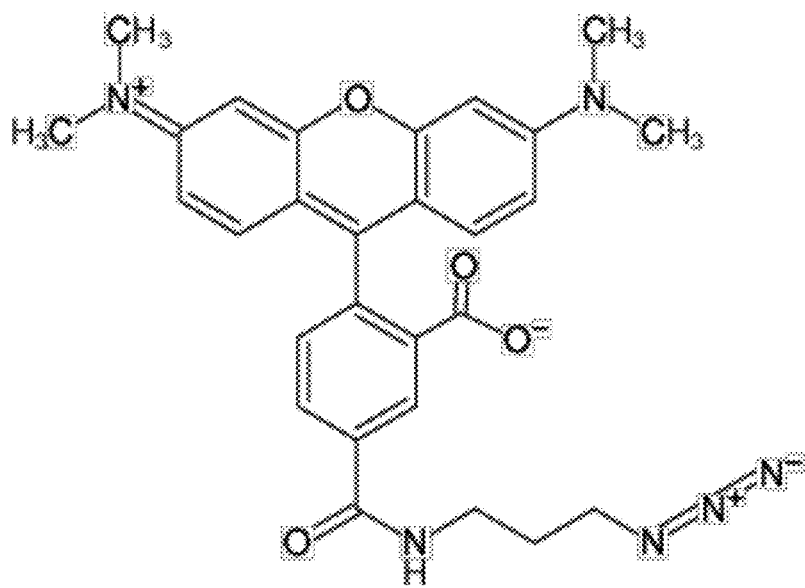

In order to wire FGM with site-specifically incorporated PrK to an electrode, a synthetic linker was used. The synthetic linker contained a pyrene group in one pole and an azide group at the other. The two groups were connected by a tri-ethylene oxide, di-ethylene oxide or mono-ethylene oxide, to get three different lengths of 8.3, 6.4 and 4.3 Å, respectively. The pyrene group is a polycyclic aromatic hydrocarbon consisting of four fused benzene rings, results in a flat aromatic system. Due to overlapping of π-bonds between aromatic side chains, the pyrene group can be attached to glassy carbon electrodes surface through π-π stacking. The azide group was used to attach the alkyne group of PrK using "click" chemistry. Exemplary pyrene-azide linker structures with different lengths are presented in FIGS. 10A-B.

Click Reaction:

Copper-catalyzed azide-alkyne cycloaddition (CuAAC) reaction is based on the formation of 1,4-disubstituted 1,2,3-triazoles between a terminal alkyne and an aliphatic azide in the presence of copper. The reaction is a facile, selective, high yielding with mild conditions and with few or no byproducts. It can be performed in room-temperature, what makes it relevant for use in proteins. CuAAC was used to link FGM to a pyrene-azide synthetic linker. Click reaction mix contained tris-KCl buffer (pH=8.2), pyrene-azide linker, $Cu^+$, Tris(3-hydroxypropyltriazolylmethyl)amine (THPTA), FGM with incorporated PrK and sodium-ascorbate (Na-Asc). Reaction mix was incubated in RT for 30-60 min with moderate mixing, centrifuged for 10 min, and the supernatant was collected for further examinations.

ncAA Incorporation Validation

TAMRA-azide is an azide-linked reporter tag that can be used for visualization of alkyne containing proteins. To validate incorporation of PrK into FGM sequence, purified FGM was clicked with the florescent marker TAMRA-azide. Clicked protein sample was loaded on SDS-PAGE and the protein gel was checked for florescence using LAS4000 camera. In addition, anti 6×His-tag antibodies will be used for Western blot analysis. MS-MS analysis was performed on isolated protein to give another validation for PrK incorporation.

Enzyme Site-Specific Wiring to GCE

Ten µL of pyrene-azide clicked to PrK containing FGM was dropped on clean GCE and incubate in RT for 15 min. The pyrene groups from the linker adhere to GCE surface through π-π stacking. GCE was washed using DW to avoid unbound protein showing signal in electrochemical measurements.

Relevant FGM DNA Sequences (all Sequences are of the FAD-GDH α-Subunit+MCD, without the γ-Subunit):

R42X (SEQ ID NO: 14); S247X (SEQ ID NO: 15); D395X (SEQ ID NO: 16); T558X (SEQ ID NO: 17); P560X (SEQ ID NO: 18).

Relevant FGM protein sequences (all sequences are of the FAD-GDH α-subunit+MCD, without the γ-subunit): R42X (SEQ ID NO: 19); S247X (SEQ ID NO: 20); D395X (SEQ ID NO: 21); T558X (SEQ ID NO: 22); P560X (SEQ ID NO: 23).

Example 2

Reagents and Materials

All DNA oligos used for the plasmid construction were purchased from Syntezza Bioscience Ltd. (Jerusalem, Israel). For the bacterial expression cultures, Auto-induction medium was purchased from Formedium™ (Hunstanton, England), glycerol was purchased from Bio-Lab ltd. (Jerusalem, Israel), chloramphenicol was purchased from Chemimpex int'l (Wood Dale, IL, USA), carbenicillin was purchased from Apollo (Manchester, England) and Propargyl-l-lysine was purchased from Synchem (Elk Grove Village, IL, USA). Tris buffer was purchased from Fisher scientific (Geel, Belgium), sodium chloride from Bio-Lab ltd. (Jerusalem, Israel), Imidzole from Glentham Life Sciences Ltd (Corsham, England), and Bradford reagent and Ni-NTA beads from Merck (Rehovot, Israel). Dimethoxybenzidine was purchased from Alfa Aesar (Heysham, England), 2,6-Dichlorophenolindophenol was purchased from Sigma-Aldrich (Rehovot, Israel), phenazine methyl sulfate and PCA from Tokyo chemical industry (Tokyo, Japan). TAMRA-Azide, THPTA and sodium ascorbate were purchased from Sigma-Aldrich (Rehovot, Israel). PDAz linker was purchased from Lumiprobe (Hunt Valley, MD, USA). Highly oriented pyrolytic graphite grade ZYB was purchased from Ted Pella inc. (Redding, CA, USA). Sodium acetate was purchased from Avantor inc. (Radnor, PA, USA), acetic acid from Bio-Lab ltd. (Jerusalem, Israel) and glassy carbon electrodes, Ag\AgCl reference electrodes, alumina polishing pad and 0.05 µm alumina slurry were purchased from ALS (Tokyo, Japan). Urea, ascorbic acid and lactate were purchased from Sigma-Aldrich (Rehovot, Israel).

Protein Expression and Verification

Figure 11A:
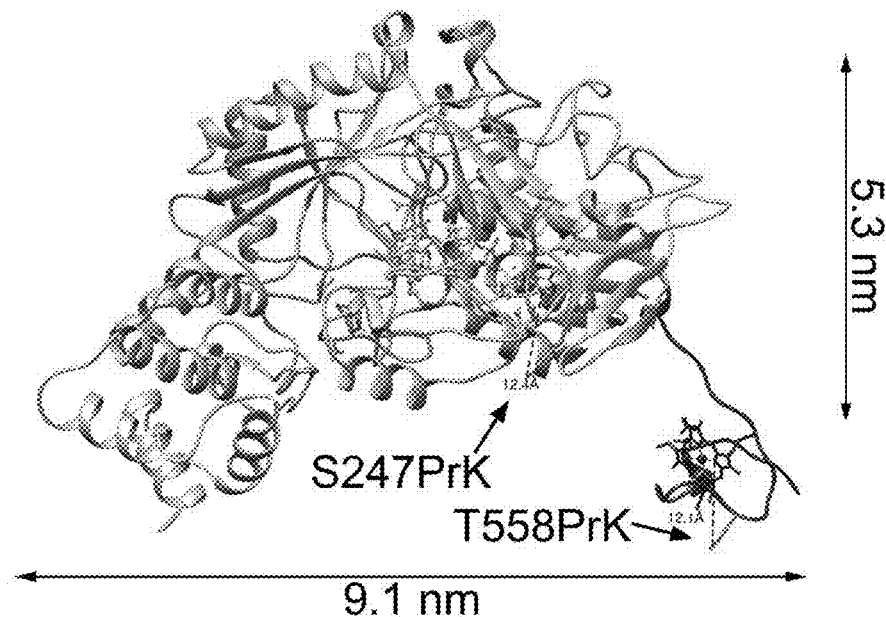
FIGS. 11A-11E present FGM structural model: a 3D model of FGM was modeled by fusing the crystal structure of FAD-GDH from *Burkholderia cepacia* (γ-subunit in silver, α-subunit in gold, PDB ID: 6A2U) to the crystal structure of MCR2 domain from MamP crystal structure in dark green (PDB ID: 4JJ0) (FIG. 11A). Dimensions of protein's height and width were estimated using UCSF chimera software. PrK at positions S247 and T558 are labeled in light blue, FAD co-factor is blue, heme is dark red; B. Chemical structures of PrK (1), PDAz (2) and PCA (3) (FIG. 11B); distance measurements between S247PrK residue and the FAD co-factor (left panel) and between the T558PrK residue and the heme domain (right panel) (FIG. 11C); schematic illustration of the glassy-carbon electrode modification procedure (FIG. 11D); and schematic illustration of the expected orientation of FGM-S247PDAz, FGM-T558PDAz and FGM-S247PCA on the electrode surface (FIG. 11E)
Figure 11B:
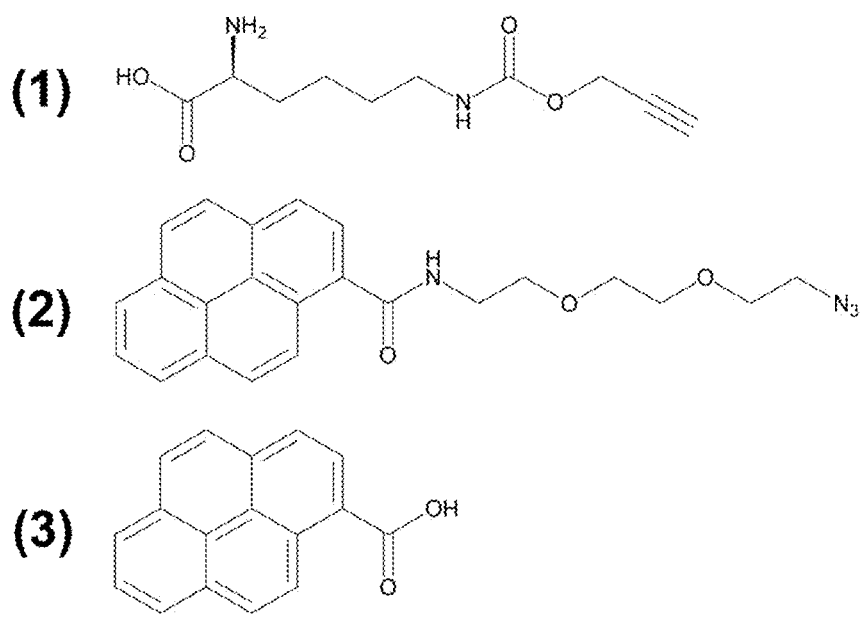

FGM-S247PrK (FIG. 11A) was expressed in 100 mL Auto-induction media supplemented with 1:100 overnight cultured bacteria, 50 µg/mL chloramphenicol, 100 µg/mL carbenicillin, 0.5% glycerol and 2 mM of UAA Propargyl-l-lysine (PrK) (FIG. 11B (1)) for 48 h in 20° C. The cells were then collected using centrifugation in 8000 rpm for 10 minutes followed by two washes with 15 mL lysis buffer (20 mM tris pH=8.0, 20 mM Imidazole, 500 mM NaCl). Cells were lysed using sonication needle and lysates were centrifuged for 30 min at 11,000 rpm to get a clear lysate. The lysate was then purified using immobilized metal affinity chromatography purification beads. The eluted protein concentration was then estimated using a Bradford assay to be 1 mg/mL and verified using anti his-tag Western blot analysis (FIG. 12A), in-gel heme staining (FIG. 12 B) and 2,6-Dichlorophenolindophenol (DCIP) glucose oxidation activity assay (FIG. 12C).

Verification of UAA Incorporation into the Protein Sequence

To verify UAA incorporation in response to the TAG mutation, a Cu(I)-catalyzed azide-alkyne cycloaddition (click reaction) was used to bind the alkyne residue of (1) to the azide residue of the fluorescent marker 5-Carboxytetramethylrhodamine-azide (TAMRA-Az). 6 µM purified protein was mixed with 50 µM TAMRA-Az, 100 mM phosphate buffer (PB) pH=7.0, 200 µM $CuCl_2$, 1.2 mM Tris(3-hydroxypropyltriazolylmethyl) amine (THPTA) and 2.5 mM sodium ascorbate (NaAsc), and incubated for 1 h in the dark at RT with shaking. The fluorescence of the conjugated protein-TAMRA-Az was then analyzed by SDS-PAGE imaging using ImageQuant LAS4000 imager on a Cy3 mode (GE Healthcare, Little Chalfont, UK) (FIG. 13).

In-Gel Heme Staining

Polyacrylamide gel after SDS-PAGE was first washed with DDW to remove the electrophoresis buffer. The gel then incubated in 20 mL DDW, and 5 mL of Dimethoxybenzidine (DMB) solution were added to a final concentration of 0.8 mg/mL. After 10 minutes incubation with shake, hydrogen peroxide was added to a final concentration of 0.7% v/v and gel was incubated with shake until bands of the oxidized DMB have appeared. Gel image was taken using ImageQuant LAS4000 imager.

FAD-GDH Glucose Oxidation Activity Assay Using DCIP

D-glucose oxidation was measured biochemically in the presence of 0.6 mM phenazine methyl sulfate (PMS), 0.6 mM 2,6-Dichlorophenolindophenol (DCIP), 100 mM D-glucose and 4.5 µM FGM-S247PrK solution in total volume of 80 µL. All dissolved in tris buffer pH=7.0. The 80 µL mix absorbance in 610 nm was measured using plate reader (BioTek instruments, Winoosky, VT) in 37° C. with shacking. Decrease in the DCIP absorbance indicates glucose oxidation. Enzyme activity unit was determined to be the amount of enzyme oxidizing one µmol of substrate per minute. The inventors have calculated the extinction coefficient of DCIP to be 4.7 $cm^{-1}mM^{-1}$.

AFM Analysis

To assess the protein wiring and its distribution on the electrode surface, a highly oriented pyrolytic graphite (HOPG) grade ZYB was used as the substrate for AFM measurements. 5 µL drop of 3 µM pyrene-conjugated protein sample was incubated on a freshly cleaved HOPG surface for 10 minutes followed by a wash with double distilled water (DDW), to remove unbound molecules, then drying in air before a measurement in 100 µL of 100 mM acetate buffer pH=5.0. HOPG surface was cleaned before each measurement by cleaving it and exposing a new layer using an adhesive tape. Measurements were performed using a Cypher-ES (Asylum research, Oxford instruments) on AC mode with a micro cantilever BL-AC40TS (Olympus, Japan).

Verification of Protein Wiring on the Electrode

To verify that both, FGM-S247PDAz and FGM-S247PCA are wired on the electrode surface, we first identified peaks using CVs (at 100 mV and 145 mV vs. Ag/AgCl, respectively). By using different scan rates, we have plotted the anodic peak current vs. the scan rates (FIG. 14). It can be seen that both samples showed high linearity of peak currents with the scan rate and not with its square root ($R^2$>0.99) which indicates wired specie on the electrode surface.

UAA Incorporation into FGM

Figure 11C:
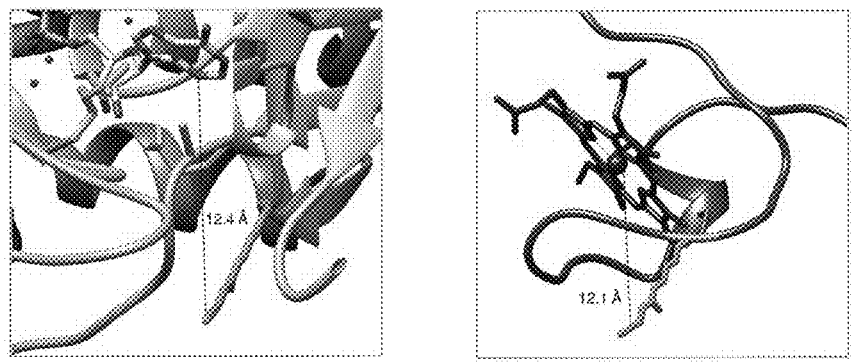
Figure 11D:
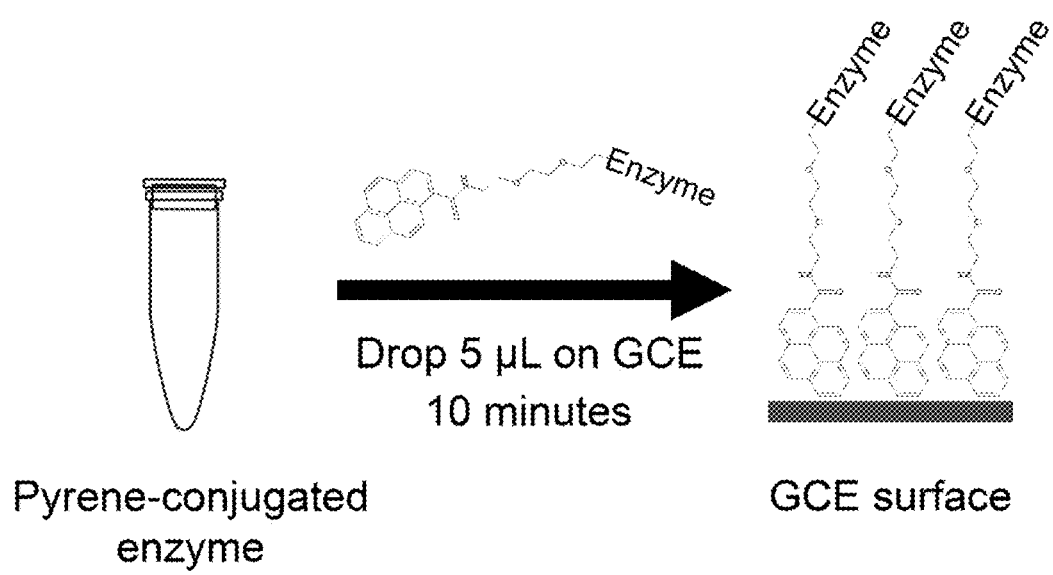

E. coli BL21 bacterial expression system was used for the expression of the FGM enzyme with site-specifically incorporated UAA. Pyrrolysyl orthogonal translation system (pylOTS) DNA sequence was amplified from the pEVOL plasmid using polymerase chain reaction (PCR) and cloned into the backbone of pec86 plasmid using Gibson's assembly to generate a new plasmid called pec86-pylOTS (FIG. 15A). pylOTS allows the continuous expression of an orthogonal translation system (orthogonal tRNA and aminoacyl tRNA synthetase) for incorporation of PrK (1) using the amber (TAG) stop codon suppression, while the pec86 plasmid is responsible for the continuous expression of E. coli cytochrome c maturation system. The second plasmid, pETDuet-FGM (FIG. 15B) was used for the expression of FGM with a TAG mutation encoded in the desired incorporation site. Four different TAG mutants were planned using site-directed mutagenesis, according to GDH crystal structure. Our guiding rational for mutation sites was to control the enzyme orientation in a manner that will allow proximity of 14 Å or less between the FAD or heme site and the electrode, without interference with the protein structure and correct folding. The sites that were tested were R42TAG and S247TAG, which are in close proximity to the FAD binding-site, while T558TAG (FIG. 11C, right panel) is in a close proximity to the heme domain. For the FAD proximity mutation site, we had the highest expression levels and activity with the S247TAG mutant (FIG. 11C, left panel). Hence, from here on we have focused our studies on S247TAG and T558TAG mutants. As a control that will allow us to find out whether the MCD affects ET properties of a site-specifically wired enzyme, we have also generated an S247TAG mutant GDH that lacks its MCD domain.

Protein Conjugation with Pyrene Containing Linkers

For the site-specific wiring of FGM-S247PrK, FGM-T558PrK and GDH-S247PrK we have used a pyrene-diethyleneglycol-azide (PDAz) linker (FIG. 11B, 2). The azide in (2) was clicked to the alkyne residue of (FIG. 11B, 1). 3 µM of protein sample was mixed with 400 µM (2), 2 mM tris pH=8.2, 10 mM KCl, 1 mM Cu(I), 1.2 mM THPTA, 2.5 mM NaAsc and 10% Dimethyl sulfoxide (DMSO). The reaction was incubated for 1 h in the dark at room temperature with shaking, then transferred to 4° C. for two days before use. For the non-specific wiring of FGM-S247PrK we have used a standard EDC-N-Hydroxysuccinimide (NHS) coupling with a PCA linker (FIG. 11B, 3). 3 µM of protein sample was mixed with 200 mM EDC, 400 mM NHS, 25 mM 4-(2-hydroxyethyl)-1-piperazineethanesulfonic acid (HEPES) buffer pH=7.0 and 100 µM (3) and incubated for 12 h at RT with shaking.

Electrode Preparations and Electrochemical Measurements

Figure 11E:
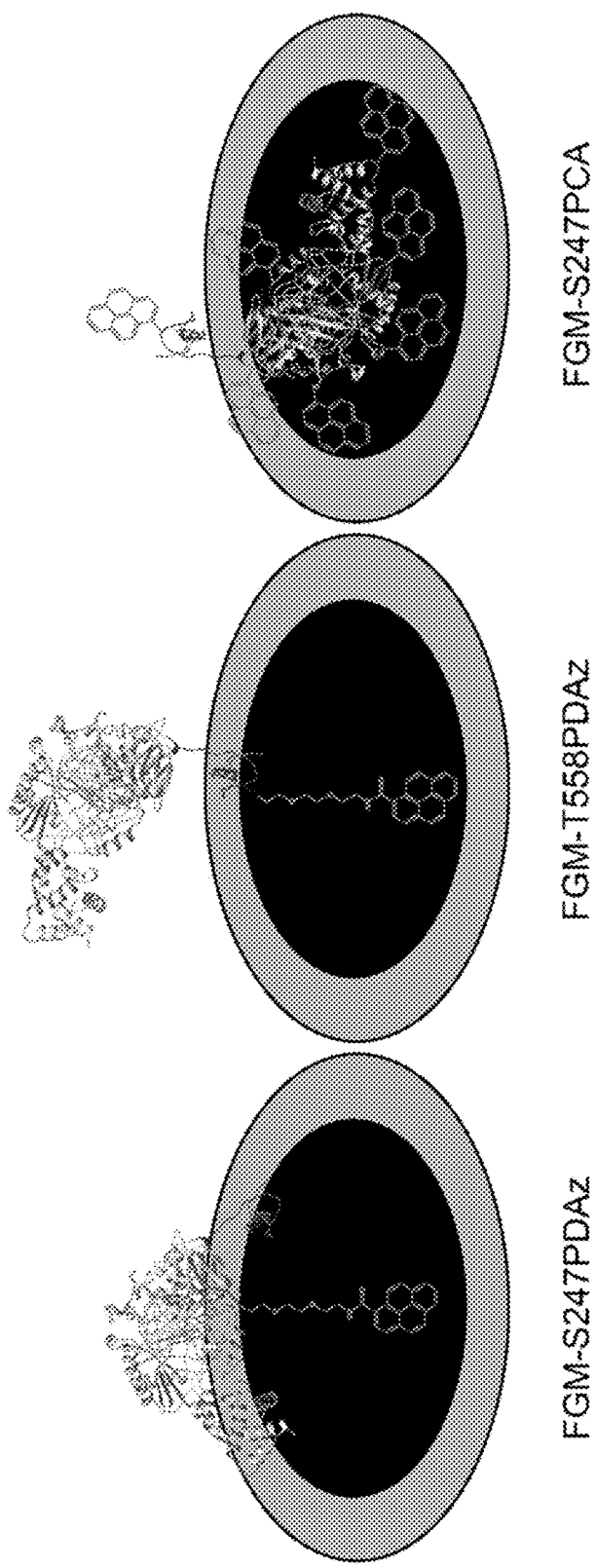

Glassy carbon electrode was first polished on 0.05 µm alumina polishing pad followed by five minutes sonication in DDW and drying using pure argon gas. Protein wiring to electrode was performed by dropping 5 µL of 3 µM pyrene-conjugated protein sample on GCE surface for 10 minutes incubation at RT (FIG. 1D) to allow the wiring of the protein through pi-pi stacking interactions between the pyrene groups and the GCE surface. After 10 minutes, the electrode was rinsed with DDW to remove unbound molecules and measured using a standard 3-electrodes electrochemical system with Ag/AgCl reference electrode and a pencil rod as the counter electrode. The expected orientations of all FGM variants towards the electrode are presented in FIG. 11E. GDH-S247PDAz is not presented since it is expected to be oriented like FGM-S247PDAz, lacking MCD. All measurements were performed using Palmsense 3 potentiostat (Palm Instruments, Houten, The Netherlands) at RT in 100 mM acetate buffer pH=5.0 under argon atmosphere and at variable scan rates. DPV measurements were performed with potential pulse of 100 mV for 0.1 sec, with scan rate of 25 mV/sec. In the multistep amperometry measurements the electrode's potential was biased from (−200) mV to 0 mV, framing the onset potentials of all modified electrodes, measuring the current decay for 10 sec for each step. In case of negative current values, a constant value was added to allow current decay linearization using natural logarithm (ln) transformation. To test the enzyme-electrode performance in the presence of interfering molecules, we have used acetate buffer supplemented with 50 µM ascorbic acid, 10 mM lactate and 10 mM urea (ALU) and measured the current response upon application of 150 mV vs. Ag/AgCl reference electrode.

Results and Discussion

Enzyme Characterization

FGM-S247PrK expression was first verified using anti His-tag Western-blot analyses (FIG. 12A). Two expression cultures were grown, while only one of them was supplemented with 2 mM of (1), the cells were then lysed and analyzed. It can be seen that only with the supplementation of (1) to the expression culture we could observe a 67 kDa band indicating the successful expression of a full-length His-tagged protein. In the absence of (1) in the growth culture, we could not detect any protein band in the relevant size. The incorporation of (1) into the protein was verified by "clicking" a tetramethylrhodamine-Azide (TAMRA-Az) to the FGM-S247PrK, GDH-S247PrK and FGM-T558PrK protein variants. Fluorescent gel image (FIG. 13) has demonstrated that the mutants of FGM and GDH indeed had (1) incorporated into their amino-acid sequence. One band in the expected size indicated that the FGM/GDH mutants are the only proteins in the sample that contain the alkyne residue of (1). Next, we have used in-gel heme staining to verify a proper minimal cytochrome c maturation process (FIG. 12B), where a band of around 67 kDa was observed, indicating a successful heme maturation. The enzyme's catalytic activity towards glucose was tested biochemically using 2,6-Dichlorophenolindophenol (DCIP) colorimetric assay for glucose oxidation (FIG. 12C). The colorimetric activity assay indicated that FGM-S247PrK, GDH-S247PrK and FGM-T558PrK are all capable of oxidizing glucose with a similar specific activity.

AFM Measurements

Understanding protein orientation on carbon surface can be realized by the combination of the knowledge the inventors have from the protein crystal structure (FIG. 11A) with AFM measurements. The inventors have analyzed the topography of an atomically flat carbon surface after wiring FGM-S247 in different methods and compare it to the known expected size of the protein. FIG. 16 show the AFM measurements of HOPG surfaces after 10 minutes of incubation in acetate buffer (FIG. 16, left panel), FGM-S247 wired through (2) (FIG. 16, middle panel) and FGM-S247 wired through (3) (FIG. 16, right panel). Since HOPG is atomically flat, we could measure the height of the bound enzyme on the HOPG surface and compare it to an approximate enzyme foot-print and height calculated from the crystal structure of FAD-GDH (FIG. 11A) taking into account the estimated lengths of the respective linkers. As a control, only acetate buffer added to the surface, does not result in salt accumulation (FIG. 16, left panel). Measurement of the FGM-S247 linked through (3) showed islands of bound molecules averaging around 70 nm in height, almost 10 times higher than the height expected from a monolayer of FGM. These islands may be a result of protein aggregation caused by the wiring of the enzyme through multiple sites as expected from non-specific wiring. Coupling to (3) may result in multiple pyrene molecules on each protein. The adhesion of the protein to the surface through multiple pyrene residues can expose the hydrophobic core of the protein, which may result in the aggregation observed in the AFM measurements. However, measurement of the FGM-S247 clicked to (2) showed scattered particles on the surface with an average height of ca. 6 nm. When taking into consideration the anchoring point of the protein (S247) and the length of (2) (which is estimated to be 0.6 nm in its stretched form), this observation is very close to the estimated height of a single layer of a wired FGM in its expected orientation (FIG. 11A) on the HOPG surface. These results suggest that using site-specific wiring affords a relatively good control over the protein orientation towards the surface as well as better surface coverage of active and correctly folded enzyme with a mono-layer pattern, although not a densely packed one, rather than multi layered and partially unfolded aggregates.

Electrochemical Characterization

For the electrochemical characterization of the wired enzyme, three different enzyme variants were compared using a site-specific wiring approach with the PDAz linker. In addition, the site-specific wiring approach was compared to a non-specific wiring approach using EDC coupling of one of the mutants to the electrode (FGM-S247PCA). In order to see whether we can detect the electroactive peaks and differentiate between the wiring approaches we have conducted DPV measurements that are more sensitive and less prone to background from non-Faradaic currents. FIG. 18A shows DPVs of FGM-S247PDAz and FGM-S247PCA in the absence of glucose. While FGM-S247PCA shows two well-defined peaks at (−100) mV and (+75) mV, FGM-S247PDAz shows a minute peak at (−250) mV and a defined albeit wide peak at ca. 0 mV vs. Ag/AgCl reference electrode. A control experiment where the DPV was performed on the conjugation reagents only (without adding protein samples) shows that the observed peaks indeed originate from FGM electroactive-sites (FIG. 17) and not from the presence of other factors in the reaction mixture.

In order to elucidate the source of the two defined peaks in the non-specifically bound enzyme compared with the broad peak in the site-specifically bound enzyme, we have calculated the apparent ET coefficient ($k_{ET}^{app}$) using multi-step amperometry as was previously described by the inventors. In FIG. 18B it can be seen that the linearized current decay of the site-specifically wired enzyme has a mono-exponential decay characteristic (R2>0.93) while the non-specifically wired enzyme has a bi-exponential decay dependence, which indicates ET from one or two redox active-sites. It cannot be excluded that the observed mono-exponential characteristic signal is an average from both, FAD and heme domain, but it can be deduced from this result that only one orientation is dominant on the electrode surface. Hence, we could extract $k_{ET}^{app}$ values from the slope of the linearized current decay curve as summarized in Table 3.

TABLE 3

Apparent electrochemical constants of the different tested variants

| Enzyme variant | $K_M^{app}$ (mM) | $i_{max}$ (μA · cm$^{-2}$) | $k_{ET}^{app}$ (s$^{-1}$) |
| --- | --- | --- | --- |
| GDH-S247PDAz | 1.55 ± 0.16 | 3.74 ± 0.12 | 8.0 ± 0.6 |
| FGM-S247PDAz | 1.89 ± 0.10 | 8.88 ± 0.40 | 11.2 ± 0.7 |
| FGM-T558PDAz | 1.58 ± 0.22 | 9.80 ± 0.18 | 13.4 ± 1.4 |
| FGM-S247PCA | 1.82 ± 0.18 | 0.55 ± 0.02 | 4.80 ± 0.02 |

Since we have observed a mono-exponential current decay from the site-specifically bound enzymes variants and a bi-exponential current decay from the non-specifically bound one, it could be an indication of the source of the two peaks: whereas one peak origin is a direct communication between the heme and the electrode and the other is a mediated ET from the FAD to the heme and then to the electrode. We hypothesize that the porphyrin, in the case of non-specific attachment is adsorbed directly on the electrode due to two lysine residues in a close proximity to its binding site. Whereas an internal ET (between the FAD and the heme) can be hardly observed when fast scan rates are being used as no electrocatalytic current is apparent in the presence of glucose under higher scan rates regime and only the two separate peaks are visible and are well defined (which is an indication of Faradaic processes but not catalytic ones) (FIG. 18C). This result is in agreement with a control experiment that have shown that no electrocatalytic current is observed from attaching the heme binding domain only to the electrode in the presence of glucose as it cannot oxidize glucose in the absence of the FAD binding domain (FIG. 18D).

FIG. 18E shows the bioelectrocatalytic currents of three site-specifically wired variants and one non-specifically wired enzyme in response to 5 mM glucose addition using CV with a slow potential scan rate of 10 mV/sec. As oppose to a high-potential-scan rate measurements (FIG. 18C), at a low scan rate, we can observe the catalytic currents from the different variants almost independently from ET rates (provided that those ET rates are faster than the potential scan rate). The catalytic response of the site-specifically wired enzymes is much higher compared to the non-specifically wired enzyme (ca. 10 folds higher increase in maximal currents) and its onset potential is lower (−100 mV for all the site-specifically wired enzymes compared to −45 mV for FGM-S247PCA). This result indicates better accessibility of the protein's electroactive site towards the electrode. Within the site-specifically wired enzymes, both GDH-S247PDAz and FGM-S247PDAz, which are bound with proximity to the FAD domain, present almost the same catalytic current while the FGM-T558PDAz shows almost two-fold higher catalytic current compared to both of them. In the site-specifically wired enzyme the substrate has a direct access to the catalytic site and the electrons can be transferred directly to the electrode without any barriers. By comparing the two points of attachment, it was evident that higher catalytic currents are observed when the enzyme was wired close to its cytochrome domain (FGMT558TAG) rather than through sites that are close to its FAD binding-site (FGMS274TAG). While with the non-specifically wired enzyme, ET can be deterred by proteins covering the electrode in different orientations that are not optimal for efficient ET.

For a given glucose concentration, the highest catalytic current was observed for FGM-T558PDAz variant, followed by FGM-S247PDAz and the lower catalytic current was observed with the GDH-S247PDAz electrode. Using high potential scan rates can help us understand whether the MCD has a role in the electron transfer to the electrode. While using low potential-scan rates resulted in almost the same catalytic current for both GDH and FGM, which are wired through the S247 site, using high scan rates resulted in higher currents for FGM. This observation suggests that the MCD participates in the ET process to the electrode, rendering it more efficient.

Apparent electron transfer rate constants were determined for the different variants, the highest $k_{ET}^{app}$ was observed for FGM-T558PDAz wired to the electrode close to its MCD, next was the FGM-S247PDAz wired close to its FAD binding-site, the lowest value was that of GDH-S247PDAz which is wired in a close proximity to its FAD however in the absence of MCD and the lowest value was that of the non-specifically wired FGM-S247PCA. Glucose concentration vs. current calibration curves of all variants is presented in FIG. 18F. It can be seen that the site-specifically wired enzymes show much higher currents than the non-specific wired ones. The apparent electrochemical Michaelis-Menten constants were determined based on a non-linear fit of the calibration curves shown in FIG. 18F (Table 3). $K_M^{app}$ of all samples did not differ significantly between variants within the error of the measurements in the range of 1.55-1.89 mM which is an indication that the mutagenesis and the site of UAA incorporation did not modify the enzyme affinity to glucose. However, $i_{max}$ values were calculated to be more than 15 times higher for FGM-S247PDAz with 8.88±0.40 µA cm$^{-2}$ vs. 0.55±0.02 µA cm$^{-2}$ for FGM-S247PCA. The site of attachment has also an effect on the $i_{max}$ values. Wiring through the T558TAG site with a proximity to the heme domain resulted in the highest current value, a slightly lower value was that of the S247TAG variant and the lowest value was that of the GDH-S247TAG. This result is another indication that the MCD has an effect on the ET abilities of the protein and are in correlation with the calculated $k_{ET}^{app}$ values. In comparison with our previously reported $i_{max}$ value for non-wired FGM which was 2.0±0.5 µA cm$^{-2}$, the site-specific wiring demonstrates more than four times higher $i_{max}$ value which is a significant improvement. Those high currents allow much higher resolution for glucose biosensing with higher sensitivity, which could be very useful and physiologically relevant for samples with low glucose concentrations such as in sweat, subcutaneous plasma or tears samples. The limit of detection (LOD) was found to be 10 µM glucose for the site-specifically wired enzymes compared to 100 µM for the non-specifically wired enzyme, with a signal to noise ratio that is larger than 3. Since FGM-T558PDAz showed the highest currents in response to glucose, we have presented its current response to the physiologically relevant concentrations in tears and sweat in the inset of FIG. 2(F). FGM-T558PDAz present a resolution of 10 µM glucose and high linearity (R$^2$=0.988) of the current measured in the 0.01 to 0.6 µM of glucose. The broader linear range of FGM-T558PDAz was found to be 0.01-2 mM glucose while FGM-S247PCA showed a linear range of 0.1-2 mM only (both with R$^2$>0.92) (FIGS. 19A-19B). Improving the surface coverage will allow more available reaction sites (in a similar manner as improving enzyme specific activity, this could be achieved by using porous electrodes for example) that can result in a broader dynamic range. To test our wired enzyme response in the presence of interfering molecules, we have used known interfering molecules in tears samples as previously described. The current response of FGM-T558PDAz was tested in ALU solution upon the addition of 0.1 mM glucose increments (FIG. 18G). The current response in the physiologically relevant glucose concentrations in tears (0.1-0.6 mM) was found linear under these conditions as shown in FIG. 18H, no interference was observed under these conditions. Being able to detect glucose in the relevant concentrations without being interfered by the ALU solution makes our system suitable for glucose detection in bodily fluids other than blood.

In conclusion, the inventors have presented the importance of a redox enzyme orientation towards an electrode. Non-specific wiring methods such as EDC-NHS coupling allows the covering of GCE with proteins but without the ability to control its orientation. By using site-specific UAA incorporation, the inventors have created a unique orthogonal "chemical handle" that allows the conjugation of a linker in only one anchoring point on the protein sequence, and by that allowed determination of a specific orientation towards the electrode. The controlled orientation results in ca. 20 times higher catalytic currents in response to glucose, higher ET efficiency that was shown by the ability of the enzyme to transfer electrons in a scan rate as high as 500 mV/sec and a scattered mono-layer pattern on the surface as observed by AFM measurements. Wiring of proteins through different sites result in a significant effect on their ET characteristics and their ability to communicate with an electrode. Using this method allows high flexibility in the UAA incorporation site which makes it a powerful tool for advanced protein engineering for enzyme-based biosensors. When site-specifically orienting a glucose oxidizing enzyme on the surface of an electrode, the inventors could observe a gain in sensitivity (down to a concentration of 10 µM glucose), however this gain in sensitivity comes with a cost, in gaining sensitivity we have lost the dynamic range that allows for higher glucose concentrations sensing. Testing FGM enzyme-electrode in ALU solution demonstrated no interference when using known interfering molecules present in tears. This makes the enzyme more suitable for non-invasive biosensors for bodily fluids other than blood such as sweat, tears and urine.

Example 3

FGM Expression Improvement

FGM expression gene is built from two sub-units, the alpha catalytic subunit, and the gamma subunit which is a helper protein that enables correct folding of the alpha subunit and responsible for the high stability of the whole protein complex. So far, we have been working with an expression plasmid that has both genes under the same promoter (Trc promoter), leading to low expression levels of FGM. In order to improve its expression levels, the inventors have cloned the FGM gene into a pETDuet plasmid, where each of the subunits is expressed from "its own" T7 promoter. The use of pETDuet results in much higher expression levels for FGM (FIG. 20), indicating that using a different promoter for each subunit indeed increases expression efficiency.

Site-Specific Wiring of FGM to an Electrode

The structure of FAD-GDH from Burkholderia cepacia was published recently and enabled the inventors to better understand the structure of the protein and better plan ncAA incorporation sites for site-specific wiring to an electrode. S247 is estimated to be 9.9 Å from the FAD site and T558 is estimated to be 10 Å from the heme site (FIG. 21). Using those variants will allow site-specific 'wiring' to an electrode with high proximity to allow direct electron transfer. To allow the incorporation of ncAA along with heme maturation, the inventors have engineered the pec86 plasmid (cytochrome c maturation plasmid) by fusing into its backbone the orthogonal tRNA and aminoacyl tRNA synthetase DNA sequences from pEVOL-pylOTS plasmid (ncAA incorporation plasmid), creating a new plasmid—pEC86-pylOTS.

Using the new ncAA incorporation and heme maturation plasmid (pec86-pylOTS) the inventors have managed to express the FGM ncAA variants with a mature c-type cytochrome. The incorporation of propargyl-lysine (PrK) was verified using a click reaction to a fluorescent marker (TAMRA-Azide) and the heme maturation was verified using in-gel heme staining. The glucose oxidation activity of the different variants was tested using a standard FAD-GDH activity assay (FIGS. 22A-22C).

The 'click' reaction with TAMRA-Azide has proved that the inventors system successfully expressed FGM with PrK incorporation (FIG. 22A). In-gel heme staining approved that our variants have a matured c-type cytochrome and that our pec89-pylOTS plasmid can do both, ncAA incorporation and heme maturation (FIG. 22B). Using the FAD-GDH activity assay proved that the inventors variants are active and can oxidize glucose (FIG. 22C). The difference in the activity rate between S247PrKFGM and T558PrKFGM is probably due to the difference in protein concentrations. Different ncAA locations have been shown to affect the protein expression efficiency and it correlates with the bends' intensities in the protein gels (FIG. 22A, 22B).

D395PrKFGM was barely active, probably due to an effect of the change on the enzyme active site. The D395 site mutation was planned according to the SWISS-model homology and found to be different from the real protein structure (found in a surface exposed loop in the homology model, while the real protein structure showed that it is located in the middle of an important α-helix).

In the next step the inventors 'clicked' the different variants to a pyrene-azide linker (FIG. 23C) to test its site-specific 'wiring' to a glassy carbon electrode (GCE).

The inventors performed a click reaction on S247PrK FGM and on WT FGM to verify their sitespecific wiring. The inventors expected that we will not be able to wire FGM since it doesn't have an incorporated PrK, while S247PrKFGM will be wired to the electrode. From the results (FIG. 23A) it could be seen that S247PrKFGM was successfully wired to the electrode and allowed high catalytic currents in response to glucose addition while WT FGM showed no bioelectrocatalytic current. As oppose to S247PrKFGM, WT FGM couldn't stay on the electrode surface and was washed away in the measurements' buffer. When comparing wired and entrapped S247PrKFGM (FIG. 23B), it can be seen that the wiring of the protein allows higher catalytic currents and lower onset potential, indicating highly efficient electron transfer (ET) that is gained due to the site-specific wiring. Same tests were performed on T558PrKFGM variant and it has been proved to be wired as well.

To eliminate the possibility that the click reaction reagents have affected the 247PrKFGM structure in a way that will allow higher catalytic response, the inventors have performed the click reaction without the pDAz linker (FIG. 24A). It was found that the clicked enzyme in the presence of pDAz showed higher catalytic current with lower onset potential indicating that the increase in efficiency is due to the site-specific wiring of FGM. The wired enzymes have been tested for electrochemical communication with the electrode in high scan rates (100-500 mV/sec) and showed catalytic currents even in those scan rates, indicating very fast ET rate (FIG. 25). The specificity of S247PrKFGM towards glucose was tested as well by introducing other sugars and measuring the chronoamperometric response (FIG. 24B). It has been shown that the wired enzyme didn't lose its specificity towards glucose.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A recombinant protein, comprising (a) alpha subunit of an FAD-GDH; and (b) a minimal c-type cytochrome peptide, wherein said alpha subunit of an FAD-GDH comprises an amino acid sequence comprising a non-canonical amino acid (ncAA), and wherein said sequence is set forth in SEQ ID NO: 20 or SEQ ID NO: 22.

2. The recombinant protein of claim 1, wherein said ncAA comprises Propargyl-lysine (PrK).

3. The polypeptide of claim 1, wherein said ncAA is covalently bound to a mediator molecule, wherein said mediator molecule is represented by Formula I:

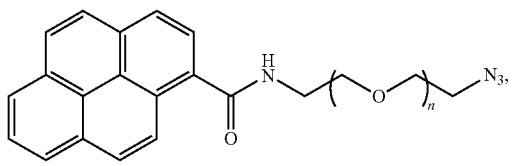

(I)

wherein n is an integer in a range from 1 to 5.

4. The polypeptide of claim 3, wherein n equals 2.

5. A polynucleotide comprising a nucleic acid sequence encoding the polypeptide of claim 1.

6. The polynucleotide of claim 5, comprising a nucleic acid sequence set forth in SEQ ID NO: 15 or SEQ ID NO: 17.

7. An expression vector or a plasmid comprising the polynucleotide of claim 5.

8. The expression vector or plasmid of claim 7, further comprising a nucleic acid sequence encoding a gamma subunit of an FAD-GDH, and optionally wherein each of said polynucleotide encoding the polypeptide of claim 1, and said nucleic acid sequence encoding said gamma subunit of an FAD-GDH are operably linked to a separate regulatory element.

9. The expression vector or plasmid of claim 8, wherein said regulatory element is a T7 promoter.

10. A transgenic or a transfected cell comprising the polynucleotide of claim 5.

11. The transgenic or transfected cell of claim 10, wherein said cell is a prokaryotic cell.

12. An extract obtained or derived from the transgenic or transfected cell of claim 11, comprising a recombinant protein comprising (a) alpha subunit of an FAD-GDH; and (b) a minimal c-type cytochrome peptide, wherein said alpha subunit of an FAD-GDH comprises an amino acid sequence comprising an ncAA, and wherein said sequence is set forth in SEQ ID NO: 20 or SEQ ID NO: 22.

13. A composition comprising the polypeptide of claim 1 and an acceptable carrier.

14. An electrode coupled to the polypeptide of claim 1, wherein said coupled is by non-covalent interactions.

15. A device comprising the electrode of claim 14.

16. A method for determining an analyte in a liquid medium, the analyte being capable to undergo a biocatalytic oxidation or reduction reaction in the presence of an oxidizer or a reducer, respectively, the method comprising:
   (i) providing the device of claim 15;
   (ii) contacting the device with the liquid medium;
   (iii) measuring the electric signal generated between the cathode and the anode, the electric signal being indicative of the presence and/or the concentration of the analyte; and
   (iv) determining the analyte based on the electric signal.

17. The method of claim 16, wherein said analyte comprises glucose.

* * * * *

SEQUENCE LISTING

<160> NUMBER OF SEQ ID NOS: 27

<210> SEQ ID NO 1
<211> LENGTH: 1617
<212> TYPE: DNA
<213> ORGANISM: Artificial
<220> FEATURE:
<223> OTHER INFORMATION: Synthetic

<400> SEQUENCE: 1

| | |
|---|---|
| atggcggata cggatacccca gaaagcggac gtggtcgtgg ttggatccgg cgtggcaggc | 60 |
| gcaatcgtgg ctcatcaact ggcaatggca ggtaaaagcg tgatcctgct ggaagctggt | 120 |
| ccgcgtatgc cgcgttggga aattgttgaa cgtttccgca atcaagtcga taaaaccgac | 180 |
| tttatggcac cgtatccgag cagcgcatgg gcaccgcatc cggaatatgg tccgccgaat | 240 |
| gattacctga tcctgaaagg cgaacacaaa tttaactcac agtacattcg tgcagtgggc | 300 |
| ggcaccacgt ggcattgggc agcctcggca tggcgcttca tcccgaacga ttttaaaatg | 360 |
| aaaaccgtgt atggcgttgg tcgtgactgg ccgattcagt acgatgacat cgaacattat | 420 |
| taccaacgcg cggaagaaga actgggcgtg tggggtccgg cccggaagaa agacctgtat | 480 |
| tcaccgcgta aagaaccgta cccgatgccg ccgctgccgc tgagtttcaa tgaacaaacc | 540 |
| attaaatccg ctctgaacgg ctatgatccg aaatttcacg tggttacgga accggtggcc | 600 |
| cgtaattcgc gcccgtacga cggtcgcccg acctgctgtg caacaataa ctgcatgccg | 660 |
| atttgtccga tcggtgcaat gtataacggc atcgtccatg tggaaaaagc tgaacaggca | 720 |
| ggtgctaaac tgattgatag tgcggtcgtg tacaaactgg aaacgggccc ggacaaacgt | 780 |
| attaccgcag ctgtttataa agataaaacg ggtgcggacc atcgcgtcga aggcaaatac | 840 |
| ttcgtgattg cggccaatgg tatcgaaacc ccgaaaattc tgctgatgag cgcgaaccgt | 900 |
| gattttccga tggtgtggc caacagttcc gatatggttg ccgcaatctg atgaccat | 960 |
| ccgggcaccg gcgtgagctt ttatgcaaac gaaaaactgt ggccgggtcg tggtccgcag | 1020 |
| gaaatgacct ctctgatcgg tttccgtgat ggcccgtttc gcgcgaatga agcagcgaag | 1080 |
| aaaattcatc tgtcaaatat gtcgcgtatc aaccaggaaa cccaaaaaat ctttaaaggc | 1140 |
| ggtaaactga tgaaaccgga agaactggat gcgcagatcc gtgaccgcag tgcccgcttt | 1200 |
| gttcaattcg attgctttca cgaaatcctg ccgcagccgg aaaatcgtat tgtcccgtcc | 1260 |
| aaaaccgcaa cggacgcagt gggtattccg cgtccggaaa ttacgtatgc gatcgatgac | 1320 |
| tacgtcaaac gtggcgcagt gcatacgcgc gaagtttatg ctaccgcggc caaagtgctg | 1380 |
| ggcggcaccg aagtggtctt caacgatgaa tttgcgccga taaccacat caccggtgcc | 1440 |
| acgattatgg gcgcggatgc ccgtgactca gtggttgata aagactgtcg cgccttcgat | 1500 |
| catccgaacc tgtttattag cagcagcagc accatgccga cggttggcac cgttaacgtc | 1560 |
| accctgacga ttgcagctct ggcactgcgt atgtctgata cgctgaaaaa agaagtc | 1617 |

<210> SEQ ID NO 2
<211> LENGTH: 510
<212> TYPE: DNA
<213> ORGANISM: Artificial
<220> FEATURE:
<223> OTHER INFORMATION: Synthetic

<400> SEQUENCE: 2

| | |
|---|---|
| atggctcaca atgacaacac cccgcactcc cgccgtaccg cgatgcggc cgtgaccggt | 60 |
| attacgcgtc gccagtggct gcaaggcgcg ctggccctga ccgcagctgg cctgacgggt | 120 |

```
tccctggccc tgcgcgcact ggctgatgat ccgggcaccg caccgctgga tacctttatg    180
acgctgagcg aagctctgac gggcaaaaaa ggtctgtctc gtgttctggg ccagcgtttt    240
ctgcaagcgc tgcaaaaagg ttcattcaaa accgcggatt cgctgccgca gctggcgggc    300
gccctggcaa gcggttctct gaacccggac caagaagctc tggcgctgaa aatcctggaa    360
gcatggtatc tgggcattgt tgataatgtg gttatcacct acgaagaagc cctgatgttt    420
agtgtcgtgt ccgacacgct ggtcattccg agctattgcc cgaacaaacc gggtttctgg    480
gccgaaaaac cgatcgaacg tcaggcataa                                    510

<210> SEQ ID NO 3
<211> LENGTH: 69
<212> TYPE: DNA
<213> ORGANISM: Artificial
<220> FEATURE:
<223> OTHER INFORMATION: Synthetic

<400> SEQUENCE: 3
attcgtgcag gtgctaccat gccgcatcgt gatcgtggtc cgtgcggtgc atgtcacgct    60
attatccag                                                           69

<210> SEQ ID NO 4
<211> LENGTH: 39
<212> TYPE: DNA
<213> ORGANISM: Artificial
<220> FEATURE:
<223> OTHER INFORMATION: Synthetic

<400> SEQUENCE: 4
gaattcggtt ctggttatgg ctctggtccg ccgggtccg                           39

<210> SEQ ID NO 5
<211> LENGTH: 2191
<212> TYPE: DNA
<213> ORGANISM: Artificial
<220> FEATURE:
<223> OTHER INFORMATION: Synthetic

<400> SEQUENCE: 5
ctcacaatga caacaccccg cactcccgcc gtaccggcga tgcggccgtg accggtatta    60
cgcgtcgcca gtggctgcaa ggcgcgctgg ccctgaccgc agctggcctg acgggttccc    120
tggccctgcg cgcactggct gatgatccgg gcaccgcacc gctggatacc tttatgacgc    180
tgagcgaagc tctgacgggc aaaaaaggtc tgtctcgtgt tctgggccag cgttttctgc    240
aagcgctgca aaaggttca ttcaaaaccg cggattcgct gccgcagctg gcgggcgccc    300
tggcaagcgg ttctctgaac ccggaccaag aagctctggc gctgaaaatc ctggaagcat    360
ggtatctggg cattgttgat aatgtggtta tcacctacga agaagccctg atgtttagtg    420
tcgtgtccga cacgctggtc attccgagct attgcccgaa caaaccgggt ttctgggccg    480
aaaaaccgat cgaacgtcag gcataatggc ggatacggat acccagaaag cggacgtggt    540
cgtggttgga tccggcgtgg caggcgcaat cgtggctcat caactggcaa tggcaggtaa    600
aagcgtgatc ctgctggaag ctggtccgcg tatgccgcgt tgggaaattg ttgaacgttt    660
ccgcaatcaa gtcgataaaa ccgactttat ggcaccgtat ccgagcagcg catgggcacc    720
gcatccggaa tatggtccgc cgaatgatta cctgatcctg aaaggcgaac acaaatttaa    780
ctcacagtac attcgtgcag tgggcggcac cacgtggcat tgggcagcct cggcatggcg    840
```

```
cttcatcccg aacgatttta aaatgaaaac cgtgtatggc gttggtcgtg actggccgat      900
tcagtacgat gacatcgaac attattacca acgcgcggaa gaagaactgg gcgtgtgggg      960
tccgggcccg gaagaagacc tgtattcacc gcgtaaagaa ccgtacccga tgccgccgct     1020
gccgctgagt ttcaatgaac aaaccattaa atccgctctg aacggctatg atccgaaatt     1080
tcacgtggtt acggaaccgg tggcccgtaa ttcgcgcccg tacgacggtc gcccgacctg     1140
ctgtggcaac aataactgca tgccgatttg tccgatcggt gcaatgtata acggcatcgt     1200
ccatgtggaa aaagctgaac aggcaggtgc taaactgatt gatagtgcgg tcgtgtacaa     1260
actggaaacg ggcccggaca aacgtattac cgcagctgtt tataaagata aaacgggtgc     1320
ggaccatcgc gtcgaaggca aatacttcgt gattgcggcc aatggtatcg aaaccccgaa     1380
aattctgctg atgagcgcga accgtgattt tccgaatggt gtggccaaca gttccgatat     1440
ggttggccgc aatctgatgg accatccggg caccggcgtg agcttttatg caaacgaaaa     1500
actgtggccg ggtcgtggtc cgcaggaaat gacctctctg atcggtttcc gtgatggccc     1560
gtttcgcgcg aatgaagcag cgaagaaaat tcatctgtca aatatgtcgc gtatcaacca     1620
ggaaacccaa aaaatcttta aaggcggtaa actgatgaaa ccggaagaac tggatgcgca     1680
gatccgtgac cgcagtgccc gctttgttca attcgattgc tttcacgaaa tcctgccgca     1740
gccggaaaat cgtattgtcc cgtccaaaac cgcaacggac gcagtgggta ttccgcgtcc     1800
ggaaattacg tatgcgatcg atgactacgt caaacgtggc gcagtgcata cgcgcgaagt     1860
ttatgctacc gcggccaaag tgctgggcgg caccgaagtg gtcttcaacg atgaatttgc     1920
gccgaataac cacatcaccg gtgccacgat tatgggcgcg gatgcccgtg actcagtggt     1980
tgataaagac tgtcgcgcct tcgatcatcc gaacctgttt attagcagca gcagcaccat     2040
gccgacggtt ggcaccgtta acgtcaccct gacgattgca gctctggcac tgcgtatgtc     2100
tgatacgctg aaaaagaag tcattcgtgc aggtgctacc atgccgcatc gtgatcgtgg     2160
tccgtgcggt gcatgtcacg ctattatcca g                                    2191

<210> SEQ ID NO 6
<211> LENGTH: 2230
<212> TYPE: DNA
<213> ORGANISM: Artificial
<220> FEATURE:
<223> OTHER INFORMATION: Synthetic

<400> SEQUENCE: 6
ctcacaatga caacaccccg cactcccgcc gtaccggcga tgcggccgtg accggtatta       60
cgcgtcgcca gtggctgcaa ggcgcgctgg ccctgaccgc agctggcctg acgggttccc      120
tggccctgcg cgcactggct gatgatccgg gcaccgcacc gctggatacc tttatgacgc      180
tgagcgaagc tctgacgggc aaaaaaggtc tgtctcgtgt tctgggccag cgttttctgc      240
aagcgctgca aaaggttca ttcaaaaccg cggattcgct gccgcagctg gcgggcgccc       300
tggcaagcgg ttctctgaac ccggaccaag aagctctggc gctgaaaatc ctggaagcat      360
ggtatctggg cattgttgat aatgtggtta tcacctacga agaagccctg atgtttagtg      420
tcgtgtccga cacgctggtc attccgagct attgcccgaa caaaccgggt ttctgggccg      480
aaaaaccgat cgaacgtcag gcataatggc ggatacggat acccagaaag cggacgtggt      540
cgtggttgga tccggcgtgg caggcgcaat cgtggctcat caactggcaa tgcaggtaa       600
aagcgtgatc ctgctggaag ctggtccgcg tatgccgcgt tgggaaattg ttgaacgttt      660
ccgcaatcaa gtcgataaaa ccgactttat ggcaccgtat ccgagcagcg catgggcacc      720
```

| | | | | |
|---|---|---|---|---|
| gcatccggaa | tatggtccgc | cgaatgatta | cctgatcctg | aaaggcgaac acaaatttaa | 780 |
| ctcacagtac | attcgtgcag | tgggcggcac | cacgtgcat | tgggcagcct cggcatggcg | 840 |
| cttcatcccg | aacgatttta | aaatgaaaac | cgtgtatggc | gttggtcgtg actggccgat | 900 |
| tcagtacgat | gacatcgaac | attattacca | acgcgcggaa | gaagaactgg gcgtgtgggg | 960 |
| tccgggcccg | gaagaagacc | tgtattcacc | gcgtaaagaa | ccgtacccga tgccgccgct | 1020 |
| gccgctgagt | ttcaatgaac | aaaccattaa | atccgctctg | aacggctatg atccgaaatt | 1080 |
| tcacgtggtt | acggaaccgg | tggcccgtaa | ttcgcgcccg | tacgacggtc gcccgacctg | 1140 |
| ctgtggcaac | aataactgca | tgccgatttg | tccgatcggt | gcaatgtata acggcatcgt | 1200 |
| ccatgtggaa | aaagctgaac | aggcaggtgc | taaactgatt | gatagtgcgg tcgtgtacaa | 1260 |
| actggaaacg | ggcccggaca | aacgtattac | cgcagctgtt | tataaagata aaacgggtgc | 1320 |
| ggaccatcgc | gtcgaaggca | atacttcgt | gattgcggcc | aatggtatcg aaaccccgaa | 1380 |
| aattctgctg | atgagcgcga | accgtgattt | tccgaatggt | gtggccaaca gttccgatat | 1440 |
| ggttggccgc | aatctgatgg | accatccggg | caccggcgtg | agcttttatg caaacgaaaa | 1500 |
| actgtgccg | gtcgtggtc | cgcaggaaat | gacctctctg | atcggtttcc gtgatggccc | 1560 |
| gtttcgcgcg | aatgaagcag | cgaagaaaat | tcatctgtca | aatatgtcgc gtatcaacca | 1620 |
| ggaaacccaa | aaaatcttta | aaggcggtaa | actgatgaaa | ccggaagaac tggatgcgca | 1680 |
| gatccgtgac | cgcagtgccc | gctttgttca | attcgattgc | tttcacgaaa tcctgccgca | 1740 |
| gccgaaaaat | cgtattgtcc | cgtccaaaac | cgcaacggac | gcagtgggta ttccgcgtcc | 1800 |
| ggaaattacg | tatgcgatcg | atgactacgt | caaacgtggc | gcagtgcata cgcgcgaagt | 1860 |
| ttatgctacc | gcggccaaag | tgctgggcgg | caccgaagtg | gtcttcaacg atgaatttgc | 1920 |
| gccgaataac | cacatcaccg | gtgccacgat | tatgggcgcg | gatgcccgtg actcagtggt | 1980 |
| tgataaagac | tgtcgcgcct | tcgatcatcc | gaacctgttt | attagcagca gcagcaccat | 2040 |
| gccgacggtt | ggcaccgtta | acgtcaccct | gacgattgca | gctctggcac tgcgtatgtc | 2100 |
| tgatacgctg | aaaaaagaag | tcgaattcgg | ttctggttat | ggctctggtc gccgggtcc | 2160 |
| gattcgtgca | ggtgctacca | tgccgcatcg | tgatcgtggt | ccgtgcggtg catgtcacgc | 2220 |
| tattatccag | | | | | 2230 |

<210> SEQ ID NO 7
<211> LENGTH: 2278
<212> TYPE: DNA
<213> ORGANISM: Artificial
<220> FEATURE:
<223> OTHER INFORMATION: Synthetic

<400> SEQUENCE: 7

| | | | | |
|---|---|---|---|---|
| ccatggctca | caatgacaac | accccgcact | cccgccgtac | cggcgatgcg gccgtgaccg | 60 |
| gtattacgcg | tcgccagtgg | ctgcaaggcg | cgctggccct | gaccgcagct ggcctgacgg | 120 |
| gttccctggc | cctgcgcgca | ctggctgatg | atccgggcac | cgcaccgctg gatacccttta | 180 |
| tgacgctgag | cgaagctctg | acgggcaaaa | aaggtctgtc | tcgtgttctg ggccagcgtt | 240 |
| ttctgcaagc | gctgcaaaaa | ggttcattca | aaaccgcgga | ttcgctgccg cagctggcgg | 300 |
| gcgccctggc | aagcggttct | ctgaacccgg | accaagaagc | tctggcgctg aaaatcctgg | 360 |
| aagcatggta | tctgggcatt | gttgataatg | tggttatcac | ctacgaagaa gccctgatgt | 420 |
| ttagtgtcgt | gtccgacacg | ctggtcattc | cgagctattg | cccgaacaaa ccgggtttct | 480 |

```
gggccgaaaa accgatcgaa cgtcaggcat aatggcggat acggataccc agaaagcgga    540
cgtggtcgtg gttggatccg gcgtggcagg cgcaatcgtg gctcatcaac tggcaatggc    600
aggtaaaagc gtgatcctgc tggaagctgg tccgcgtatg ccgcgttggg aaattgttga    660
acgtttccgc aatcaagtcg ataaaaccga ctttatggca ccgtatccga gcagcgcatg    720
ggcaccgcat ccggaatatg gtccgccgaa tgattacctg atcctgaaag cgaacacaa     780 atttaactca cagtacattc gtgcagtggg cggcaccacg tggcattggg cagcctcggc    840
atggcgcttc atcccgaacg attttaaaat gaaaaccgtg tatggcgttg gtcgtgactg    900
gccgattcag tacgatgaca tcgaacatta ttaccaacgc gcggaagaag aactgggcgt    960
gtggggtccg ggcccggaag aagacctgta ttcaccgcgt aaagaaccgt acccgatgcc   1020
gccgctgccg ctgagtttca tgaacaaac cattaaatcc gctctgaacg ctatgatcc     1080 gaaatttcac gtggttacgg aaccggtggc ccgtaattcg cgcccgtacg acggtcgccc   1140
gacctgctgt ggcaacaata actgcatgcc gatttgtccg atcggtgcaa tgtataacgg   1200
catcgtccat gtggaaaaag ctgaacaggc aggtgctaaa ctgattgata gtgcggtcgt   1260
gtacaaactg gaaacggcc cggacaaacg tattaccgca gctgtttata agataaaaac    1320
gggtgcggac catcgcgtcg aaggcaaata cttcgtgatt gcggccaatg gtatcgaaac   1380
cccgaaaatt ctgctgatga gcgcgaaccg tgattttccg aatggtgtgg ccaacagttc   1440
cgatatggtt ggccgcaatc tgatggacca tccgggcacc ggcgtgagct tttatgcaaa   1500
cgaaaaactg tggccgggtc gtggtccgca ggaaatgacc tctctgatcg gtttccgtga   1560
tggcccgttt cgcgcgaatg aagcagcgaa gaaaattcat ctgtcaaata tgtcgcgtat   1620
caaccaggaa acccaaaaaa tctttaaagg cggtaaactg atgaaaccgg aagaactgga   1680
tgcgcagatc cgtgaccgca gtgcccgctt tgttcaattc gattgctttc acgaaatcct   1740
gccgcagccg gaaaatcgta ttgtcccgtc caaaaccgca acggacgcag tgggtattcc   1800
gcgtccggaa attacgtatg cgatcgatga ctacgtcaaa cgtggcgcag tgcatacgcg   1860
cgaagtttat gctaccgcgg ccaaagtgct gggcggcacc gaagtggtct tcaacgatga   1920
atttgcgccg aataaccaca tcaccggtgc acgattatg ggcgcggatg cccgtgactc    1980
agtggttgat aaagactgtc gcgccttcga tcatccgaac ctgtttatta gcagcagcag   2040
caccatgccg acggttggca ccgttaacgt caccctgacg attgcagctc tggcactgcg   2100
tatgtctgat acgctgaaaa agaagtcga attcggttct ggttatggct ctggtccgcc    2160
gggtccgatt cgtgcaggtg ctaccatgcc gcatcgtgat cgtggtccgt gcggtgcatg   2220
tcacgctatt atccagggca gtggttccgg ccatcaccat caccatcact aaaagctt     2278
```

<210> SEQ ID NO 8
<211> LENGTH: 527
<212> TYPE: PRT
<213> ORGANISM: Artificial
<220> FEATURE:
<223> OTHER INFORMATION: Synthetic

<400> SEQUENCE: 8

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45
```

```
Val Glu Arg Phe Arg Asn Gln Val Asp Lys Thr Asp Phe Met Ala Pro
 50                  55                  60
Tyr Pro Ser Ser Ala Trp Ala Pro His Pro Glu Tyr Gly Pro Pro Asn
 65                  70                  75                  80
Asp Tyr Leu Ile Leu Lys Gly Glu His Lys Phe Asn Ser Gln Tyr Ile
                 85                  90                  95
Arg Ala Val Gly Gly Thr Thr Trp His Trp Ala Ala Ser Ala Trp Arg
                100                 105                 110
Phe Ile Pro Asn Asp Phe Lys Met Lys Thr Val Tyr Gly Val Gly Arg
            115                 120                 125
Asp Trp Pro Ile Gln Tyr Asp Asp Ile Glu His Tyr Tyr Gln Arg Ala
130                 135                 140
Glu Glu Glu Leu Gly Val Trp Gly Pro Gly Pro Glu Glu Asp Leu Tyr
145                 150                 155                 160
Ser Pro Arg Lys Glu Pro Tyr Pro Met Pro Pro Leu Pro Leu Ser Phe
                165                 170                 175
Asn Glu Gln Thr Ile Lys Ser Ala Leu Asn Gly Tyr Asp Pro Lys Phe
            180                 185                 190
His Val Val Thr Glu Pro Val Ala Arg Asn Ser Arg Pro Tyr Asp Gly
        195                 200                 205
Arg Pro Thr Cys Cys Gly Asn Asn Asn Cys Met Pro Ile Cys Pro Ile
210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                245                 250                 255
Pro Asp Lys Arg Ile Thr Ala Ala Val Tyr Lys Asp Lys Thr Gly Ala
            260                 265                 270
Asp His Arg Val Glu Gly Lys Tyr Phe Val Ile Ala Ala Asn Gly Ile
        275                 280                 285
Glu Thr Pro Lys Ile Leu Leu Met Ser Ala Asn Arg Asp Phe Pro Asn
290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Asn Glu Lys Leu Trp Pro Gly
                325                 330                 335
Arg Gly Pro Gln Glu Met Thr Ser Leu Ile Gly Phe Arg Asp Gly Pro
            340                 345                 350
Phe Arg Ala Asn Glu Ala Ala Lys Lys Ile His Leu Ser Asn Met Ser
        355                 360                 365
Arg Ile Asn Gln Glu Thr Gln Lys Ile Phe Lys Gly Gly Lys Leu Met
370                 375                 380
Lys Pro Glu Glu Leu Asp Ala Gln Ile Arg Asp Arg Ser Ala Arg Phe
385                 390                 395                 400
Val Gln Phe Asp Cys Phe His Glu Ile Leu Pro Gln Pro Glu Asn Arg
                405                 410                 415
Ile Val Pro Ser Lys Thr Ala Thr Asp Ala Val Gly Ile Pro Arg Pro
            420                 425                 430
Glu Ile Thr Tyr Ala Ile Asp Asp Tyr Val Lys Arg Gly Ala Val His
        435                 440                 445
Thr Arg Glu Val Tyr Ala Thr Ala Lys Val Leu Gly Gly Thr Glu
450                 455                 460
Val Val Phe Asn Asp Glu Phe Ala Pro Asn Asn His Ile Thr Gly Ala
```

```
            465                 470                 475                 480
Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu
            515                 520                 525

<210> SEQ ID NO 9
<211> LENGTH: 562
<212> TYPE: PRT
<213> ORGANISM: Artificial
<220> FEATURE:
<223> OTHER INFORMATION: Synthetic

<400> SEQUENCE: 9

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
```

```
                305                 310                 315                 320
Pro Gly Thr Gly Val Ser Phe Tyr Ala Asn Glu Lys Leu Trp Pro Gly
                    325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
        370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Ile Arg Ala Gly Ala
    530                 535                 540

Thr Met Pro His Arg Asp Arg Gly Pro Cys Gly Ala Cys His Ala Ile
545                 550                 555                 560

Ile Gln

<210> SEQ ID NO 10
<211> LENGTH: 586
<212> TYPE: PRT
<213> ORGANISM: Artificial
<220> FEATURE:
<223> OTHER INFORMATION: Synthetic

<400> SEQUENCE: 10

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110
```

```
Phe Ile Pro Asn Asp Phe Lys Met Lys Thr Val Tyr Gly Val Gly Arg
            115                 120                 125
Asp Trp Pro Ile Gln Tyr Asp Ile Glu His Tyr Tyr Gln Arg Ala
130                 135                 140
Glu Glu Glu Leu Gly Val Trp Gly Pro Gly Glu Glu Asp Leu Tyr
145                 150                 155                 160
Ser Pro Arg Lys Glu Pro Tyr Pro Met Pro Pro Leu Pro Leu Ser Phe
            165                 170                 175
Asn Glu Gln Thr Ile Lys Ser Ala Leu Asn Gly Tyr Asp Pro Lys Phe
            180                 185                 190
His Val Val Thr Glu Pro Val Ala Arg Asn Ser Arg Pro Tyr Asp Gly
            195                 200                 205
Arg Pro Thr Cys Cys Gly Asn Asn Cys Met Pro Ile Cys Pro Ile
210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                245                 250                 255
Pro Asp Lys Arg Ile Thr Ala Ala Val Tyr Lys Asp Lys Thr Gly Ala
            260                 265                 270
Asp His Arg Val Glu Gly Lys Tyr Phe Val Ile Ala Ala Asn Gly Ile
            275                 280                 285
Glu Thr Pro Lys Ile Leu Leu Met Ser Ala Asn Arg Asp Phe Pro Asn
290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Asn Glu Lys Leu Trp Pro Gly
                325                 330                 335
Arg Gly Pro Gln Glu Met Thr Ser Leu Ile Gly Phe Arg Asp Gly Pro
            340                 345                 350
Phe Arg Ala Asn Glu Ala Ala Lys Lys Ile His Leu Ser Asn Met Ser
            355                 360                 365
Arg Ile Asn Gln Glu Thr Gln Lys Ile Phe Lys Gly Gly Lys Leu Met
370                 375                 380
Lys Pro Glu Glu Leu Asp Ala Gln Ile Arg Asp Arg Ser Ala Arg Phe
385                 390                 395                 400
Val Gln Phe Asp Cys Phe His Glu Ile Leu Pro Gln Pro Glu Asn Arg
                405                 410                 415
Ile Val Pro Ser Lys Thr Ala Thr Asp Ala Val Gly Ile Pro Arg Pro
            420                 425                 430
Glu Ile Thr Tyr Ala Ile Asp Asp Tyr Val Lys Arg Gly Ala Val His
            435                 440                 445
Thr Arg Glu Val Tyr Ala Thr Ala Ala Lys Val Leu Gly Gly Thr Glu
450                 455                 460
Val Val Phe Asn Asp Glu Phe Ala Pro Asn Asn His Ile Thr Gly Ala
465                 470                 475                 480
Thr Ile Met Gly Ala Asp Ala Arg Asp Ser Val Val Asp Lys Asp Cys
                485                 490                 495
Arg Ala Phe Asp His Pro Asn Leu Phe Ile Ser Ser Ser Thr Met
            500                 505                 510
Pro Thr Val Gly Thr Val Asn Val Thr Leu Thr Ile Ala Ala Leu Ala
            515                 520                 525
```

```
Leu Arg Met Ser Asp Thr Leu Lys Lys Glu Val Glu Phe Gly Ser Gly
            530                 535                 540

Tyr Gly Ser Gly Pro Pro Gly Pro Ile Arg Ala Gly Ala Thr Met Pro
545                 550                 555                 560

His Arg Asp Arg Gly Pro Cys Gly Ala Cys His Ala Ile Ile Gln Gly
                565                 570                 575

Ser Gly Ser Gly His His His His His His
            580                 585

<210> SEQ ID NO 11
<211> LENGTH: 575
<212> TYPE: PRT
<213> ORGANISM: Artificial
<220> FEATURE:
<223> OTHER INFORMATION: Synthetic

<400> SEQUENCE: 11

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
290                 295                 300
```

```
Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
                435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Glu Phe Gly Ser Gly
530                 535                 540

Tyr Gly Ser Gly Pro Pro Gly Pro Ile Arg Ala Gly Ala Thr Met Pro
545                 550                 555                 560

His Arg Asp Arg Gly Pro Cys Gly Ala Cys His Ala Ile Ile Gln
            565                 570                 575
```

```
<210> SEQ ID NO 12
<211> LENGTH: 586
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (42)..(42)
<223> OTHER INFORMATION: X is R or a non-canonical amino acid.
<220> FEATURE:
<221> NAME/KEY: X
<222> LOCATION: (247)..(247)
<223> OTHER INFORMATION: X is S or a non-canonical amino acid.
<220> FEATURE:
<221> NAME/KEY: X
<222> LOCATION: (395)..(395)
<223> OTHER INFORMATION: X is D or a non-canonical amino acid.
<220> FEATURE:
<221> NAME/KEY: X
<222> LOCATION: (558)..(558)
<223> OTHER INFORMATION: X is T or a non-canonical amino acid.
<220> FEATURE:
<221> NAME/KEY: X
<222> LOCATION: (560)..(560)
<223> OTHER INFORMATION: X is P or a non-canonical amino acid.
```

<400> SEQUENCE: 12

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Xaa Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Xaa Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Xaa Arg Ser Ala Arg Phe
385                 390                 395                 400

Val Gln Phe Asp Cys Phe His Glu Ile Leu Pro Gln Pro Glu Asn Arg
                405                 410                 415
```

```
Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val Glu Phe Gly Ser Gly
    530                 535                 540

Tyr Gly Ser Gly Pro Pro Gly Pro Ile Arg Ala Gly Ala Xaa Met Xaa
545                 550                 555                 560

His Arg Asp Arg Gly Pro Cys Gly Ala Cys His Ala Ile Ile Gln Gly
                565                 570                 575

Ser Gly Ser Gly His His His His His
            580                 585

<210> SEQ ID NO 13
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (42)..(42)
<223> OTHER INFORMATION: X is R or a non-canonical amino acid
<220> FEATURE:
<221> NAME/KEY: X
<222> LOCATION: (247)..(247)
<223> OTHER INFORMATION: X is S or a non-canonical amino acid
<220> FEATURE:
<221> NAME/KEY: X
<222> LOCATION: (395)..(395)
<223> OTHER INFORMATION: X is D or a non-canonical amino acid
<220> FEATURE:
<221> NAME/KEY: X
<222> LOCATION: (558)..(558)
<223> OTHER INFORMATION: X is T or a non-canonical amino acid
<220> FEATURE:
<221> NAME/KEY: X
<222> LOCATION: (560)..(560)
<223> OTHER INFORMATION: X is P or a non-canonical amino acid

<400> SEQUENCE: 13

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Xaa Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80
```

-continued

```
Asp Tyr Leu Ile Leu Lys Gly Glu His Lys Phe Asn Ser Gln Tyr Ile
             85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
            130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
            165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
            210                 215                 220

Gly Ala Met Tyr Asn Gly Ile Val His Val Glu Lys Ala Glu Gln Ala
225                 230                 235                 240

Gly Ala Lys Leu Ile Asp Xaa Ala Val Val Tyr Lys Leu Glu Thr Gly
            245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Xaa Arg Ser Ala Arg Phe
385                 390                 395                 400

Val Gln Phe Asp Cys Phe His Glu Ile Leu Pro Gln Pro Glu Asn Arg
            405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
            450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495

Arg Ala Phe Asp His Pro Asn Leu Phe Ile Ser Ser Ser Ser Thr Met
```

```
                500                 505                 510
Pro Thr Val Gly Thr Val Asn Val Thr Leu Thr Ile Ala Ala Leu Ala
            515                 520                 525

Leu Arg Met Ser Asp Thr Leu Lys Lys Glu Val Glu Phe Gly Ser Gly
        530                 535                 540

Tyr Gly Ser Gly Pro Pro Gly Pro Ile Arg Ala Gly Ala Xaa Met Xaa
545                 550                 555                 560

His Arg Asp Arg Gly Pro Cys Gly Ala Cys His Ala Ile Ile Gln
                565                 570                 575

<210> SEQ ID NO 14
<211> LENGTH: 1727
<212> TYPE: DNA
<213> ORGANISM: Artificial
<220> FEATURE:
<223> OTHER INFORMATION: Synthetic

<400> SEQUENCE: 14
tggcggatac ggatacccag aaagcggacg tggtcgtggt tggatccggc gtggcaggcg      60
caatcgtggc tcatcaactg caatggcag gtaaaagcgt gatcctgctg aagctggtc     120 cgtagatgcc gcgttgggaa attgttgaac gtttccgcaa tcaagtcgat aaaaccgact     180
ttatggcacc gtatccgagc agcgcatggg caccgcatcc ggaatatggt ccgccgaatg     240
attacctgat cctgaaaggc gaacacaaat taactcaca gtacattcgt gcagtgggcg     300
gcaccacgtg gcattgggca gcctcggcat ggcgcttcat cccgaacgat tttaaaatga     360
aaaccgtgta tggcgttggt cgtgactggc cgattcagta cgatgacatc gaacattatt     420
accaacgcgc ggaagaagaa ctgggcgtgt ggggtccggg cccggaagaa gacctgtatt     480
caccgcgtaa agaaccgtac ccgatgccgc gctgccgct gagtttcaat gaacaaacca     540
ttaaatccgc tctgaacggc tatgatccga aatttcacgt ggttacggaa ccggtggccc     600
gtaattcgcg cccgtacgac ggtcgcccga cctgctgtgg caacaataac tgcatgccga     660
tttgtccgat cggtgcaatg tataacggca tcgtccatgt ggaaaaagct gaacaggcag     720
gtgctaaact gattgatagt gcggtcgtgt acaaactgga acgggcccg acaaacgta     780 ttaccgcagc tgtttataaa gataaaacgg gtgcggacca tcgcgtcgaa ggcaaatact     840
tcgtgattgc ggccaatggt atcgaaaccc gaaaattct gctgatgagc gcgaaccgtg     900
attttccgaa tggtgtggcc aacagttccg atatggttgg ccgcaatctg atggaccatc     960
cgggcaccgg cgtgagcttt tatgcaaacg aaaaactgtg gccgggtcgt ggtccgcagg    1020
aaatgacctc tctgatcggt ttccgtgatg gcccgtttcg cgcgaatgaa gcagcgaaga    1080
aaattcatct gtcaaatatg tcgcgtatca accaggaaac ccaaaaaatc tttaaaggcg    1140
gtaaactgat gaaaccggaa gaactggatg cgcagatccg tgaccgcagt gcccgctttg    1200
ttcaattcga ttgcttttcac gaaatcctgc cgcagccgga aaatcgtatt gtcccgtcca    1260
aaaccgcaac ggacgcagtg gtattccgc gtccggaaat tacgtatgcg atcgatgact    1320
acgtcaaacg tggcgcagtg catacgcgcg aagtttatgc taccgcggcc aaagtgctgg    1380
gcggcaccga agtggtcttc aacgatgaat ttgcgccgaa taccacatc accggtgcca    1440 cgattatggg cgcggatgcc cgtgactcag tggttgataa agactgtcgc gccttcgatc    1500
atccgaacct gtttattagc agcagcagca ccatgccgac ggttggcacc gttaacgtca    1560
ccctgacgat tgcagctctg gcactgcgta tgtctgatac gctgaaaaaa gaagtcgaat    1620
tcggttctgg ttatggctct ggtccgccgg gtccgattcg tgcaggtgct accatgccgc    1680
```

-continued atcgtgatcg tggtccgtgc ggtgcatgtc acgctattat ccagtaa       1727

<210> SEQ ID NO 15
<211> LENGTH: 1728
<212> TYPE: DNA
<213> ORGANISM: Artificial
<220> FEATURE:
<223> OTHER INFORMATION: Synthetic

<400> SEQUENCE: 15
atggcggata cggatcccca gaaagcggac gtggtcgtgg ttggatccgg cgtggcaggc        60
gcaatcgtgg ctcatcaact ggcaatggca ggtaaaagcg tgatcctgct ggaagctggt      120
ccgcgtatgc cgcgttggga aattgttgaa cgtttccgca atcaagtcga taaaaccgac      180
tttatggcac cgtatccgag cagcgcatgg gcaccgcatc cggaatatgg tccgccgaat      240
gattacctga tcctgaaagg cgaacacaaa tttaactcac agtacattcg tgcagtgggc      300
ggcaccacgt ggcattgggc agcctcggca tggcgcttca tcccgaacga ttttaaaatg      360
aaaaccgtgt atggcgttgg tcgtgactgg ccgattcagt acgatgacat cgaacattat      420
taccaacgcg cggaagaaga actgggcgtg tggggtccgg gcccggaaga agacctgtat      480
tcaccgcgta agaaccgta cccgatgccg ccgctgccgc tgagtttcaa tgaacaaacc      540
attaaatccg ctctgaacgg ctatgatccg aaatttcacg tggttacgga accggtggcc      600
cgtaattcgc gcccgtacga cggtcgcccg acctgctgtg gcaacaataa ctgcatgccg      660
atttgtccga tcggtgcaat gtataacggc atcgtccatg tggaaaaagc tgaacaggca      720
ggtgctaaac tgattgatta ggcggtcgtg tacaaactgg aaacgggccc ggacaaacgt      780
attaccgcag ctgtttataa agataaaacg ggtgcggacc atcgcgtcga aggcaaatac      840
ttcgtgattg cggccaatgg tatcgaaacc ccgaaaattc tgctgatgag cgcgaaccgt      900
gattttccga atggtgtggc caacagttcc gatatggttg ccgcaatctt gatggaccat      960
ccgggcaccg gcgtgagctt ttatgcaaac gaaaaactgt ggccgggtcg tggtccgcag     1020
gaaatgacct ctctgatcgg tttccgtgat ggcccgtttc gcgcgaatga agcagcgaag     1080
aaaattcatc tgtcaaatat gtcgcgtatc aaccaggaaa cccaaaaaat ctttaaaggc     1140
ggtaaactga tgaaaccgga agaactggat gcgcagatcc gtgaccgcag tgcccgcttt     1200
gttcaattcg attgctttca cgaaatcctg ccgcagccgg aaaatcgtat tgtcccgtcc     1260
aaaaccgcaa cggacgcagt gggtattccg cgtccggaaa ttacgtatgc gatcgatgac     1320
tacgtcaaac gtggcgcagt gcatacgcgc gaagtttatg ctaccgcggc caaagtgctg     1380
ggcggcaccg aagtggtctt caacgatgaa tttgcgccga ataaccacat caccggtgcc     1440
acgattatgg gcgcggatgc ccgtgactca gtggttgata agactgtcg cgccttcgat     1500
catccgaacc tgtttattag cagcagcagc accatgccga cggttggcac cgttaacgtc     1560
accctgacga ttgcagctct ggcactgcgt atgtctgata cgctgaaaaa agaagtcgaa     1620
ttcggttctg gttatggctc tggtccgccg ggtccgattc gtgcaggtgc taccatgccg     1680
catcgtgatc gtggtccgtg cggtgcatgt cacgctatta tccagtaa                 1728

<210> SEQ ID NO 16
<211> LENGTH: 1729
<212> TYPE: DNA
<213> ORGANISM: Artificial
<220> FEATURE:
<223> OTHER INFORMATION: Synthetic

<400> SEQUENCE: 16

```
atggcggata cggataccca gaaagcggac gtggtcgtgg ttggatccgg cgtggcaggc      60
gcaatcgtgg ctcatcaact ggcaatggca ggtaaaagcg tgatcctgct ggaagctggt     120
ccgcgtatgc cgcgttggga aattgttgaa cgtttccgca atcaagtcga taaaaccgac     180
tttatggcac cgtatccgag cagcgcatgg gcaccgcatc cggaatatgg tccgccgaat     240
gattacctga tcctgaaagg cgaacacaaa tttaactcac agtacattcg tgcagtgggc     300
ggcaccacgt ggcattgggc agcctcggca tggcgcttca tcccgaacga tttaaaatg     360
aaaaccgtgt atggcgttgg tcgtgactgg ccgattcagt acgatgacat cgaacattat     420
taccaacgcg cggaagaaga actgggcgtg tggggtccgg gcccggaaga agacctgtat     480
tcaccgcgta agaaccgta cccgatgccg ccgctgccgc tgagtttcaa tgaacaaacc     540
attaaatccg ctctgaacgg ctatgatccg aaatttcacg tggttacgga accggtggcc     600
cgtaattcgc gcccgtacga cggtcgcccg acctgctgtg caacaataa ctgcatgccg     660
atttgtccga tcggtgcaat gtataacggc atcgtccatg tggaaaaagc tgaacaggca     720
ggtgctaaac tgattgatag tgcggtcgtg tacaaactgg aaacgggccc ggacaaacgt     780
attaccgcag ctgtttataa agataaaacg ggtgcggacc atcgcgtcga aggcaaatac     840
ttcgtgattg cggccaatgg tatcgaaacc ccgaaaattc tgctgatgag cgcgaaccgt     900
gattttccga tggtgtggc caacagttcc gatatggttg ccgcaatct gatgaccat     960
ccgggcaccg gcgtgagctt ttatgcaaac gaaaaactgt ggccgggtcg tggtccgcag    1020
gaaatgacct ctctgatcgg tttccgtgat ggcccgtttc gcgcgaatga agcagcgaag    1080
aaaattcatc tgtcaaatat gtcgcgtatc aaccaggaaa cccaaaaaat ctttaaaggc    1140
ggtaaactga tgaaaccgga agaactggat gcgcagatcc gttagcgcag tgcccgcttt    1200
gttcaattcg attgctttca cgaaatcctg ccgcagccgg aaaatcgtat tgtcccgtcc    1260
aaaaccgcaa cggacgcagt gggtattccg cgtccggaaa ttacgtatgc gatcgatgac    1320
tacgtcaaac gtggcgcagt gcatacgcgc gaagtttatg ctaccgcggc caaagtgctg    1380
ggcggcaccg aagtggtctt caacgatgaa tttgcgccga taaccacat caccggtgcc    1440
acgattatgg gcgcggatgc ccgtgactca gtggttgata aagactgtcg cgccttcgat    1500
catccgaacc tgtttattag cagcagcagc accatgccga cggttggcac cgttaacgtc    1560
accctgacga ttgcagctct ggcactgcgt atgtctgata cgctgaaaaa agaagtcgaa    1620
ttcggttctg gttatggctc tggtccgccg ggtccgattc gtgcaggtgc taccatgccg    1680
catcgtgatc gtggtccgtg cggtgcatgt cacgctatta tccaggtaa                1729
```

<210> SEQ ID NO 17
<211> LENGTH: 1728
<212> TYPE: DNA
<213> ORGANISM: Artificial
<220> FEATURE:
<223> OTHER INFORMATION: Synthetic

<400> SEQUENCE: 17

```
atggcggata cggataccca gaaagcggac gtggtcgtgg ttggatccgg cgtggcaggc      60
gcaatcgtgg ctcatcaact ggcaatggca ggtaaaagcg tgatcctgct ggaagctggt     120
ccgcgtatgc cgcgttggga aattgttgaa cgtttccgca atcaagtcga taaaaccgac     180
tttatggcac cgtatccgag cagcgcatgg gcaccgcatc cggaatatgg tccgccgaat     240
gattacctga tcctgaaagg cgaacacaaa tttaactcac agtacattcg tgcagtgggc     300
```

```
ggcaccacgt ggcattgggc agcctcggca tggcgcttca tcccgaacga ttttaaaatg      360
aaaaccgtgt atggcgttgg tcgtgactgg ccgattcagt acgatgacat cgaacattat      420
taccaacgcg cggaagaaga actgggcgtg tggggtccgg ccccggaaga agacctgtat      480
tcaccgcgta aagaaccgta cccgatgccg ccgctgccgc tgagtttcaa tgaacaaacc      540
attaaatccg ctctgaacgg ctatgatccg aaatttcacg tggttacgga accggtggcc      600
cgtaattcgc gcccgtacga cggtcgcccg acctgctgtg caacaataa ctgcatgccg       660 atttgtccga tcggtgcaat gtataacggc atcgtccatg tggaaaaagc tgaacaggca      720
ggtgctaaac tgattgatag tgcggtcgtg tacaaactgg aaacgggccc ggacaaacgt      780
attaccgcag ctgtttataa agataaaacg ggtgcggacc atcgcgtcga aggcaaatac      840
ttcgtgattg cggccaatgg tatcgaaacc ccgaaaattc tgctgatgag cgcgaaccgt      900
gattttccga atggtgtggc caacagttcc gatatggttg ccgcaatct gatggaccat       960 ccgggcaccg gcgtgagctt ttatgcaaac gaaaaactgt ggccgggtcg tggtccgcag     1020
gaaatgacct ctctgatcgg tttccgtgat ggcccgtttc gcgcgaatga agcagcgaag     1080
aaaattcatc tgtcaaatat gtcgcgtatc aaccaggaaa cccaaaaaat ctttaaaggc     1140
ggtaaactga tgaaaccgga agaactggat gcgcagatcc gtgaccgcag tgcccgcttt     1200
gttcaattcg attgctttca cgaaatcctg ccgcagccgg aaaatcgtat tgtcccgtcc     1260
aaaaccgcaa cggacgcagt gggtattccg cgtccggaaa ttacgtatgc gatcgatgac     1320
tacgtcaaac gtggcgcagt gcatacgcgc gaagtttatg ctaccgcggc caaagtgctg     1380
ggcggcaccg aagtggtctt caacgatgaa tttgcgccga ataaccacat caccggtgcc     1440
acgattatgg gcgcggatgc ccgtgactca gtggttgata agactgtcg cgccttcgat       1500 catccgaacc tgtttattag cagcagcagc accatgccga cggttggcac cgttaacgtc     1560
accctgacga ttgcagctct ggcactgcgt atgtctgata cgctgaaaaa agaagtcgaa     1620
ttcggttctg gttatggctc tggtccgccg ggtccgattc gtgcaggtgc ttagatgccg     1680
catcgtgatc gtggtccgtg cggtgcatgt cacgctatta tccagtaa                  1728
```

<210> SEQ ID NO 18
<211> LENGTH: 1728
<212> TYPE: DNA
<213> ORGANISM: Artificial
<220> FEATURE:
<223> OTHER INFORMATION: Synthetic

<400> SEQUENCE: 18

```
atggcggata cggataccca gaaagcggac gtggtcgtgg ttggatccgg cgtggcaggc       60
gcaatcgtgg ctcatcaact ggcaatggca ggtaaaagcg tgatcctgct ggaagctggt      120
ccgcgtatgc gcgttggga aattgttgaa cgtttccgca atcaagtcga taaaaccgac       180
tttatggcac cgtatccgag cagcgcatgg gcaccgcatc cggaatatgg tccgccgaat      240
gattacctga tcctgaaagg cgaacacaaa tttaactcac agtacattcg tgcagtgggc      300
ggcaccacgt ggcattgggc agcctcggca tggcgcttca tcccgaacga ttttaaaatg      360
aaaaccgtgt atggcgttgg tcgtgactgg ccgattcagt acgatgacat cgaacattat      420
taccaacgcg cggaagaaga actgggcgtg tggggtccgg ccccggaaga agacctgtat      480
tcaccgcgta aagaaccgta cccgatgccg ccgctgccgc tgagtttcaa tgaacaaacc      540
attaaatccg ctctgaacgg ctatgatccg aaatttcacg tggttacgga accggtggcc      600
```

```
cgtaattcgc gcccgtacga cggtcgcccg acctgctgtg gcaacaataa ctgcatgccg    660
atttgtccga tcggtgcaat gtataacggc atcgtccatg tggaaaaagc tgaacaggca    720
ggtgctaaac tgattgatag tgcggtcgtg tacaaactgg aaacgggccc ggacaaacgt    780
attaccgcag ctgtttataa agataaaacg ggtgcggacc atcgcgtcga aggcaaatac    840
ttcgtgattg cggccaatgg tatcgaaacc ccgaaaattc tgctgatgag cgcgaaccgt    900
gattttccga atggtgtggc caacagttcc gatatggttg ccgcaatct  gatgaccat    960 ccgggcaccg gcgtgagctt ttatgcaaac gaaaaactgt ggccgggtcg tggtccgcag   1020
gaaatgacct ctctgatcgg tttccgtgat ggcccgtttc gcgcgaatga agcagcgaag   1080
aaaattcatc tgtcaaatat gtcgcgtatc aaccaggaaa cccaaaaaat ctttaaaggc   1140
ggtaaactga tgaaaccgga agaactggat gcgcagatcc gtgaccgcag tgcccgcttt   1200
gttcaattcg attgctttca cgaaatcctg ccgcagccgg aaaatcgtat tgtcccgtcc   1260
aaaaccgcaa cggacgcagt gggtattccg cgtccggaaa ttacgtatgc gatcgatgac   1320
tacgtcaaac gtggcgcagt gcatacgcgc gaagtttatg ctaccgcggc caaagtgctg   1380
ggcggcaccg aagtggtctt caacgatgaa tttgcgccga ataaccacat caccggtgcc   1440
acgattatgg gcgcggatgc ccgtgactca gtggttgata aagactgtcg cgccttcgat   1500
catccgaacc tgtttattag cagcagcagc accatgccga cggttggcac cgttaacgtc   1560
accctgacga ttgcagctct ggcactgcgt atgtctgata cgctgaaaaa agaagtcgaa   1620
ttcggttctg gttatggctc tggtccgccg ggtccgattc gtgcaggtgc taccatgtag   1680
catcgtgatc gtggtccgtg cggtgcatgt cacgctatta tccagtaa              1728
```

<210> SEQ ID NO 19  
<211> LENGTH: 575  
<212> TYPE: PRT  
<213> ORGANISM: Artificial  
<220> FEATURE:  
<223> OTHER INFORMATION: Synthetic  
<220> FEATURE:  
<221> NAME/KEY: X  
<222> LOCATION: (42)..(42)  
<223> OTHER INFORMATION: X is a non-canonical amino acid

<400> SEQUENCE: 19

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Xaa Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140
```

```
Glu Glu Glu Leu Gly Val Trp Gly Pro Gly Glu Asp Leu Tyr
145                 150                 155                 160

Ser Pro Arg Lys Glu Pro Tyr Pro Met Pro Leu Pro Leu Ser Phe
            165                 170                 175

Asn Glu Gln Thr Ile Lys Ser Ala Leu Asn Gly Tyr Asp Pro Lys Phe
        180                 185                 190

His Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
    275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
    355                 360                 365

Arg Ile Asn Gln Glu Thr Gln Lys Ile Phe Lys Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Tyr Val Lys Arg Gly Ala Val His
        435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Glu Phe Gly Ser Gly
        530                 535                 540

Tyr Gly Ser Gly Pro Gly Pro Ile Arg Ala Gly Ala Thr Met Pro
545                 550                 555                 560

His Arg Asp Arg Gly Pro Cys Gly Ala Cys His Ala Ile Ile Gln
```

-continued

```
                  565                 570                 575

<210> SEQ ID NO 20
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (247)..(247)
<223> OTHER INFORMATION: X is a non-canonical amino acid

<400> SEQUENCE: 20

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
                35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
                115                 120                 125

Asp Trp Pro Ile Gln Tyr Asp Asp Ile Glu His Tyr Tyr Gln Arg Ala
                130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
                210                 215                 220

Gly Ala Met Tyr Asn Gly Ile Val His Val Glu Lys Ala Glu Gln Ala
225                 230                 235                 240

Gly Ala Lys Leu Ile Asp Xaa Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
                275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335
```

-continued

```
Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
        370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Glu Phe Gly Ser Gly
    530                 535                 540

Tyr Gly Ser Gly Pro Pro Gly Pro Ile Arg Ala Gly Ala Thr Met Pro
545                 550                 555                 560

His Arg Asp Arg Gly Pro Cys Gly Ala Cys His Ala Ile Ile Gln
                565                 570                 575
```

<210> SEQ ID NO 21
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (395)..(395)
<223> OTHER INFORMATION: X is a non-canonical amino acid

<400> SEQUENCE: 21

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110
```

```
Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
        130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Cys Met Pro Ile Cys Pro Ile
            210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Xaa Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
            435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
                515                 520                 525
```

```
Leu Arg Met Ser Asp Thr Leu Lys Lys Glu Val Glu Phe Gly Ser Gly
            530                 535                 540

Tyr Gly Ser Gly Pro Pro Gly Pro Ile Arg Ala Gly Ala Thr Met Pro
545                 550                 555                 560

His Arg Asp Arg Gly Pro Cys Gly Ala Cys His Ala Ile Ile Gln
                565                 570                 575

<210> SEQ ID NO 22
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (558)..(558)
<223> OTHER INFORMATION: X is a non-canonical amino acid

<400> SEQUENCE: 22

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
115                 120                 125

Asp Trp Pro Ile Gln Tyr Asp Asp Ile Glu His Tyr Tyr Gln Arg Ala
            130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
            245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
290                 295                 300
```

-continued

```
Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
        340                 345                 350

Phe Arg Ala Asn Glu Ala Ala Lys Lys Ile His Leu Ser Asn Met Ser
    355                 360                 365

Arg Ile Asn Gln Glu Thr Gln Lys Ile Phe Lys Gly Gly Lys Leu Met
370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
            405                 410                 415

Ile Val Pro Ser Lys Thr Ala Thr Asp Ala Val Gly Ile Pro Arg Pro
        420                 425                 430

Glu Ile Thr Tyr Ala Ile Asp Asp Tyr Val Lys Arg Gly Ala Val His
    435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495

Arg Ala Phe Asp His Pro Asn Leu Phe Ile Ser Ser Ser Thr Met
        500                 505                 510

Pro Thr Val Gly Thr Val Asn Val Thr Leu Thr Ile Ala Ala Leu Ala
    515                 520                 525

Leu Arg Met Ser Asp Thr Leu Lys Lys Glu Val Glu Phe Gly Ser Gly
530                 535                 540

Tyr Gly Ser Gly Pro Pro Gly Pro Ile Arg Ala Gly Ala Xaa Met Pro
545                 550                 555                 560

His Arg Asp Arg Gly Pro Cys Gly Ala Cys His Ala Ile Ile Gln
            565                 570                 575
```

```
<210> SEQ ID NO 23
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (560)..(560)
<223> OTHER INFORMATION: X is a non-canonical amino acid

<400> SEQUENCE: 23
```

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
```

```
                65                  70                  75                  80
Asp Tyr Leu Ile Leu Lys Gly Glu His Lys Phe Asn Ser Gln Tyr Ile
                    85                  90                  95
Arg Ala Val Gly Gly Thr Thr Trp His Trp Ala Ala Ser Ala Trp Arg
                    100                 105                 110
Phe Ile Pro Asn Asp Phe Lys Met Lys Thr Val Tyr Gly Val Gly Arg
                    115                 120                 125
Asp Trp Pro Ile Gln Tyr Asp Asp Ile Glu His Tyr Tyr Gln Arg Ala
                    130                 135                 140
Glu Glu Glu Leu Gly Val Trp Gly Pro Gly Glu Glu Asp Leu Tyr
145                 150                 155                 160
Ser Pro Arg Lys Glu Pro Tyr Pro Met Pro Pro Leu Pro Leu Ser Phe
                    165                 170                 175
Asn Glu Gln Thr Ile Lys Ser Ala Leu Asn Gly Tyr Asp Pro Lys Phe
                    180                 185                 190
His Val Val Thr Glu Pro Val Ala Arg Asn Ser Arg Pro Tyr Asp Gly
                    195                 200                 205
Arg Pro Thr Cys Cys Gly Asn Asn Asn Cys Met Pro Ile Cys Pro Ile
210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                    245                 250                 255
Pro Asp Lys Arg Ile Thr Ala Ala Val Tyr Lys Asp Lys Thr Gly Ala
                    260                 265                 270
Asp His Arg Val Glu Gly Lys Tyr Phe Val Ile Ala Ala Asn Gly Ile
                    275                 280                 285
Glu Thr Pro Lys Ile Leu Leu Met Ser Ala Asn Arg Asp Phe Pro Asn
                    290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Asn Glu Lys Leu Trp Pro Gly
                    325                 330                 335
Arg Gly Pro Gln Glu Met Thr Ser Leu Ile Gly Phe Arg Asp Gly Pro
                    340                 345                 350
Phe Arg Ala Asn Glu Ala Ala Lys Lys Ile His Leu Ser Asn Met Ser
                    355                 360                 365
Arg Ile Asn Gln Glu Thr Gln Lys Ile Phe Lys Gly Gly Lys Leu Met
                    370                 375                 380
Lys Pro Glu Glu Leu Asp Ala Gln Ile Arg Asp Arg Ser Ala Arg Phe
385                 390                 395                 400
Val Gln Phe Asp Cys Phe His Glu Ile Leu Pro Gln Pro Glu Asn Arg
                    405                 410                 415
Ile Val Pro Ser Lys Thr Ala Thr Asp Ala Val Gly Ile Pro Arg Pro
                    420                 425                 430
Glu Ile Thr Tyr Ala Ile Asp Asp Tyr Val Lys Arg Gly Ala Val His
                    435                 440                 445
Thr Arg Glu Val Tyr Ala Thr Ala Ala Lys Val Leu Gly Gly Thr Glu
                    450                 455                 460
Val Val Phe Asn Asp Glu Phe Ala Pro Asn Asn His Ile Thr Gly Ala
465                 470                 475                 480
Thr Ile Met Gly Ala Asp Ala Arg Asp Ser Val Val Asp Lys Asp Cys
                    485                 490                 495
```

```
Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Glu Phe Gly Ser Gly
    530                 535                 540

Tyr Gly Ser Gly Pro Pro Gly Pro Ile Arg Ala Gly Ala Thr Met Xaa
545             550                 555                 560

His Arg Asp Arg Gly Pro Cys Gly Ala Cys His Ala Ile Ile Gln
                565                 570                 575

<210> SEQ ID NO 24
<211> LENGTH: 18
<212> TYPE: DNA
<213> ORGANISM: Artificial
<220> FEATURE:
<223> OTHER INFORMATION: Synthetic

<400> SEQUENCE: 24
catcaccatc accatcac                                              18

<210> SEQ ID NO 25
<211> LENGTH: 15
<212> TYPE: DNA
<213> ORGANISM: Artificial
<220> FEATURE:
<223> OTHER INFORMATION: Synthetic

<400> SEQUENCE: 25
ggcagtggtt ccggc                                                 15

<210> SEQ ID NO 26
<211> LENGTH: 2278
<212> TYPE: DNA
<213> ORGANISM: Artificial
<220> FEATURE:
<223> OTHER INFORMATION: Synthetic

<400> SEQUENCE: 26
ccatggctca caatgacaac accccgcact cccgccgtac cggcgatgcg gccgtgaccg    60
gtattacgcg tcgccagtgg ctgcaaggcg cgctggccct gaccgcagct ggcctgacgg   120
gttccctggc cctgcgcgca ctggctgatg atccgggcac cgcaccgctg gatacctta   180 tgacgctgag cgaagctctg acgggcaaaa aaggtctgtc tcgtgttctg ggccagcgtt   240
ttctgcaagc gctgcaaaaa ggttcattca aaaccgcgga ttcgctgccg cagctggcgg   300
gcgccctggc aagcggttct ctgaacccgg accaagaagc tctggcgctg aaaatcctgg   360
aagcatggta tctgggcatt gttgataatg tggttatcac ctacgaagaa gccctgatgt   420
ttagtgtcgt gtccgacacg ctggtcattc cgagctattg cccgaacaaa ccgggtttct   480
gggccgaaaa accgatcgaa cgtcaggcat aatggcggat acggataccc agaaagcgga   540
cgtggtcgtg gttggatccg gcgtggcagg cgcaatcgtg gctcatcaac tggcaatggc   600
aggtaaaagc gtgatcctgc tggaagctgg tccgcgtatg ccgcgttggg aaattgttga   660
acgtttccgc aatcaagtcg ataaaaccga ctttatggca ccgtatccga gcagcgcatg   720
ggcaccgcat ccggaatatg gtccgccgaa tgattacctg atcctgaaag cgaacacaa   780 atttaactca cagtacattc gtgcagtggg cggcaccacg tggcattggg cagcctcggc   840
atggcgcttc atcccgaacg attttaaaat gaaaaccgtg tatggcgttg gtcgtgactg   900
```

```
gccgattcag tacgatgaca tcgaacatta ttaccaacgc gcggaagaag aactgggcgt    960
gtggggtccg ggcccggaag aagacctgta ttcaccgcgt aaagaaccgt acccgatgcc   1020
gccgctgccg ctgagtttca tgaacaaac cattaaatcc gctctgaacg ctatgatcc    1080 gaaatttcac gtggttacgg aaccggtggc ccgtaattcg cgcccgtacg acggtcgccc   1140
gacctgctgt ggcaacaata actgcatgcc gatttgtccg atcggtgcaa tgtataacgg   1200
catcgtccat gtggaaaaag ctgaacaggc aggtgctaaa ctgattgata gtgcggtcgt   1260
gtacaaactg gaaacgggcc cggacaaacg tattaccgca gctgtttata agataaaac    1320 gggtgcggac catcgcgtcg aaggcaaata cttcgtgatt gcggccaatg gtatcgaaac   1380
cccgaaaatt ctgctgatga gcgcgaaccg tgattttccg aatggtgtgg ccaacagttc   1440
cgatatggtt ggccgcaatc tgatggacca tccgggcacc ggcgtgagct tttatgcaaa   1500
cgaaaaactg tggccgggtc gtggtccgca ggaaatgacc tctctgatcg gtttccgtga   1560
tggcccgttt cgcgcgaatg aagcagcgaa gaaaattcat ctgtcaaata tgtcgcgtat   1620
caaccaggaa acccaaaaaa tctttaaagg cggtaaactg atgaaaccgg aagaactgga   1680
tgcgcagatc cgtgaccgca gtgcccgctt tgttcaattc gattgctttc acgaaatcct   1740
gccgcagccg gaaatcgta ttgtcccgtc caaaaccgca acggacgcag tgggtattcc    1800
gcgtccggaa attacgtatg cgatcgatga ctacgtcaaa cgtggcgcag tgcatacgcg   1860
cgaagtttat gctaccgcgg ccaaagtgct gggcggcacc gaagtggtct tcaacgatga   1920
atttgcgccg aataaccaca tcaccggtgc cacgattatg ggcgcggatg cccgtgactc   1980
agtggttgat aaagactgtc gcgccttcga tcatccgaac ctgtttatta gcagcagcag   2040
caccatgccg acggttggca ccgttaacgt caccctgacg attgcagctc tggcactgcg   2100
tatgtctgat acgctgaaaa aagaagtcga attcggttct ggttatggct ctggtccgcc   2160
gggtccgatt cgtgcaggtg ctaccatgcc gcatcgtgat cgtggtccgt gcggtgcatg   2220
tcacgctatt atccagggca gtggttccgg ccatcaccat caccatcact aaaagctt    2278
```

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Gly Ser Gly Tyr Gly Ser Gly
1               5